United States Patent
Marshall et al.

(10) Patent No.: US 11,993,633 B2
(45) Date of Patent: *May 28, 2024

(54) CONFORMATIONALLY STABILIZED RSV PRE-FUSION F PROTEINS

(71) Applicants: CALDER BIOSCIENCES INC., New York, NY (US); THE UNITED STATES OF AMERICA, AS REPRESENTED BY THE SECRETARY, DEPARTMENT OF HEALTH AND HUMAN SERVICES, Bethesda, MD (US)

(72) Inventors: Christopher Patrick Marshall, New York, NY (US); Jason Scott McLellan, Norwich, VT (US); Peter Joseph Alff, New York, NY (US); Claudio Bertuccioli, New York, NY (US); Roberto Mariani, San Diego, CA (US)

( * ) Notice: Subject to any disclaimer, the term of this patent is extended or adjusted under 35 U.S.C. 154(b) by 81 days.

This patent is subject to a terminal disclaimer.

(21) Appl. No.: 17/332,901

(22) Filed: May 27, 2021

(65) Prior Publication Data

US 2022/0119454 A1 Apr. 21, 2022

Related U.S. Application Data

(63) Continuation of application No. 16/155,857, filed on Oct. 9, 2018, now abandoned, which is a continuation of application No. 14/340,519, filed on Jul. 24, 2014, now Pat. No. 10,125,172.

(60) Provisional application No. 61/858,533, filed on Jul. 25, 2013.

(51) Int. Cl.
| | | |
|---|---|---|
| C07K 14/005 | (2006.01) | |
| A61K 39/12 | (2006.01) | |
| A61K 39/155 | (2006.01) | |
| A61K 39/00 | (2006.01) | |

(52) U.S. Cl.
CPC ............ C07K 14/005 (2013.01); A61K 39/12 (2013.01); A61K 39/155 (2013.01); A61K 2039/525 (2013.01); C12N 2760/18534 (2013.01)

(58) Field of Classification Search
None
See application file for complete search history.

(56) References Cited

U.S. PATENT DOCUMENTS

| | | | |
|---|---|---|---|
| 7,037,894 B2 | 5/2006 | Marshall et al. | |
| 7,445,912 B2 | 11/2008 | Marshall et al. | |
| 8,563,002 B2 | 10/2013 | Baudoux et al. | |
| 9,393,297 B2 | 7/2016 | Marshall et al. | |
| 9,738,689 B2 * | 8/2017 | Kwong | C07K 14/005 |
| 9,950,058 B2 | 4/2018 | Che et al. | |
| 10,125,172 B2 * | 11/2018 | Marshall | A61K 39/155 |
| 10,155,023 B2 | 12/2018 | Marshall | |
| 11,129,887 B2 | 9/2021 | Marshall et al. | |
| 11,261,239 B2 | 3/2022 | Swanson et al. | |
| 11,267,848 B2 | 3/2022 | Marshall et al. | |
| 11,629,181 B2 | 4/2023 | Swanson et al. | |
| 11,655,284 B2 | 5/2023 | Swanson et al. | |
| 2005/0054572 A1 | 3/2005 | Marshall et al. | |
| 2007/0184518 A1 | 8/2007 | Marshall et al. | |
| 2011/0123556 A1 | 5/2011 | Phogat et al. | |
| 2012/0083008 A1 | 4/2012 | Marshall | |
| 2013/0236905 A1 | 9/2013 | Marshall et al. | |
| 2013/0317205 A1 | 11/2013 | Marshall et al. | |
| 2015/0030622 A1 | 1/2015 | Marshall et al. | |
| 2015/0056233 A1 | 2/2015 | Marshall et al. | |
| 2016/0046675 A1 | 2/2016 | Kwong et al. | |
| 2017/0182151 A1 | 6/2017 | Che et al. | |
| 2017/0298101 A1 | 10/2017 | Kwong et al. | |

FOREIGN PATENT DOCUMENTS

| | | |
|---|---|---|
| WO | 2001029247 A1 | 4/2001 |
| WO | 2011008974 A1 | 1/2011 |
| WO | 2012158613 A1 | 11/2012 |
| WO | 2014160463 A1 | 10/2014 |
| WO | 2015013551 A1 | 1/2015 |
| WO | 2015020913 A1 | 2/2015 |
| WO | 2017174568 A1 | 10/2017 |
| WO | 2019178521 A1 | 9/2019 |

OTHER PUBLICATIONS

International Search Report for PCT/US2014/048086.
International Search Report for PCT/US2018/45463.
Anonymous "Dityrosine Locked Prefusion F Protein: A Path To A Protective RSV Vaccine." SBIR Source, Jun. 1, 2014.

(Continued)

*Primary Examiner* — Shanon A. Foley
*Assistant Examiner* — Myron G Hill
(74) *Attorney, Agent, or Firm* — Grimes & Yvon LLP

(57) ABSTRACT

In some embodiments, the present invention provides respiratory syncytial virus (RSV) F proteins, polypeptides and protein complexes that comprise one or more cross-links to stabilize the protein, polypeptide or protein complex in its pre-fusion conformation. In some embodiments the present invention provides RSV F proteins, polypeptides and protein complexes comprising one or more mutations to facilitate such cross-linking. In some embodiments the present invention provides compositions comprising such proteins, polypeptides or protein complexes, including vaccine compositions, and methods of making and using the same.

16 Claims, 31 Drawing Sheets

Specification includes a Sequence Listing.

(56) References Cited

OTHER PUBLICATIONS

Costello "Targeting RSV with Vaccines and Small Molecule Drugs." Infectious Disorders Drug Targets, vol. 12, pp. 110-128 (Apr. 2012).
Krarup "A highly stable prefusion Rsv F vaccine derived from structural analysis of the fusion mechanism." Nat. Commun. vol. 6: p. 8143 (Sep. 2015).
Magro "Neutralizing antibodies against the preactive form of respiratory syncytial virus fusion protein offer unique possibilities for clinical intervention." Proceedings of the National Academy of Sciences, vol. 109, No. 8, pp. 3089-3094, Feb. 21, 2012 (Feb. 21, 2012).
McLellan. "Structure of RSV Fusion Glycoprotein Trimer Bound to a Prefusion-Specific Neutralizing Antibody" Science. vol. 340, pp. 1113-1117. Apr. 25, 2013 (Apr. 25, 2013).
McLellan "Structure-Based Design of a Fusion Glycoprotein Vaccine for Respiratory Syncytial Virus." Science, vol. 342, No. 6158, pp. 592-598, Oct. 31, 2013 (Oct. 31, 2013).
McLellan "Structure and Function of RSV Surface Glycoproteins." Curr Top Microbiol Immunol. 201; 372: 83-104.
Murphy, "An update on approaches to the development of respiratory synctial virus (RSV) and parainfluenza virus type 3 (PIV3) vaccines", Virus Research, 1994, vol. 32, pp. 13-26.
Weisshaar, "Blocking Respiratory Syncytial Virus Entry: A Story with Twists," DNA and Cell Biology, 2015, Vo. 34 pp. 505-510.
Dey et al., "Characterization of Human Immunodeficiency Virus Type 1 Monomeric and Trimeric gp120 Glycoproteins Stabilized in the CD4-Bound State: Antigenicity, Biophysics, and Immunogenicity," Journal of Virology, (2007), vol. 81, No. 11, pp. 5579-5593.

\* cited by examiner

>RSV_F_WT subtype A soluble

MELLILKANAITTILTAVTFCFASGQNITEEFYQSTCSAVSKGYLSALRTGWYTSVITIELSNIKENKCNGTDAKVK
LIKQELDKYKNAVTELQLLMQSTPATNNRARRELPRFMNYTLNNAKKTNVTLSKKRKRRFLGFLLGVGSAIASGVAV
SKVLHLEGEVNKIKSALLSTNKAVVSLSNGVSVLTSKVLDLKNYIDKQLLPIVNKQSCSISNIETVIEFQQKNNRLL
EITREFSVNAGVTTPVSTYMLTNSELLSLINDMPITNDQKKLMSNNVQIVRQQSYSIMSIIKEEVLAYVVQLPLYGV
IDTPCWKLHTSPLCTTNTKEGSNICLTRTDRGWYCDNAGSVSFFPQAETCKVQSNRVFCDTMNSLTLPSEVNLCNVD
IFNPKYDCKIMTSKTDVSSSVITSLGAIVSCYGKTKCTASNKNRGIIKTFSNGCDYVSNKGVDTVSVGNTLYYVNKQ
EGKSLYVKGEPIINFYDPLVFPSDEFDASISQVNEKINQSLAFIRKSDELLSAIGGYIPEAPRDGQAYVRKDGEWVL
LSTFLGGLVPRGSHHHHHHSAWSHPQFEK (SEQ ID NO:1)

Fig. 1A

>WT_RSV-F_full_length_subtype(A) (Accession# AHL84194)

MELLILKANAITTILTAVTFCFASGQNITEEFYQSTCSAVSKGYLSALRTGWYTSVITIELSNIKENKCNGTDAKVK
LIKQELDKYKNAVTELQLLMQSTPATNNRARRELPRFMNYTLNNAKKTNVTLSKKRKRRFLGFLLGVGSAIASGVAV
SKVLHLEGEVNKIKSALLSTNKAVVSLSNGVSVLTSKVLDLKNYIDKQLLPIVNKQSCSISNIETVIEFQQKNNRLL
EITREFSVNAGVTTPVSTYMLTNSELLSLINDMPITNDQKKLMSNNVQIVRQQSYSIMSIIKEEVLAYVVQLPLYGV
IDTPCWKLHTSPLCTTNTKEGSNICLTRTDRGWYCDNAGSVSFFPQAETCKVQSNRVFCDTMNSLTLPSEVNLCNVD
IFNPKYDCKIMTSKTDVSSSVITSLGAIVSCYGKTKCTASNKNRGIIKTFSNGCDYVSNKGVDTVSVGNTLYYVNKQ
EGKSLYVKGEPIINFYDPLVFPSDEFDASISQVNEKINQSLAFIRKSDELLHNVNTGKSTTNIMITTIIIVIIVLL
SLIAIGLLLYCKAKNTPVTLSKDQLSGINNIAFSK (SEQ ID NO:2)

Fig. 1B

>WT_RSV-F_soluble_subtype(B)

MELLIHRSSAIFLTLAINALYLTSSQNITEEFYQSTCSAVSRGYFSALRTGWYTSVITIELSNITETKCN
GTDTKVKLIKQELDKYKNAVTELQLLMQNTPAANNRARREAPQHMNYTINTTKNLNVSISKKRKRRFLGF
LLGVGSAIASGIAVSKVLHLEGEVNKIKNALLSTNKAVVSLSNGVSVLTSKVLDLKNYINNQLLPIVNQQ
SCRIFNIETVIEFQQKNSRLLEITREFSVNAGVTTPLSTYMLTNSELLSLINDMPITNDQKKLMSSNVQI
VRQQSYSIMSIIKEEVLAYVVQLPIYGVIDTPCWKLHTSPLCTTNIKEGSNICLTRTDRGWYCDNAGSVS
FFPQADTCKVQSNRVFCDTMNSLTLPSEVSLCNTDIFNSKYDCKIMTSKTDISSSVITSLGAIVSCYGKT
KCTASNKNRGIIKTFSNGCDYVSNKGVDTVSVGNTLYYVNKLEGKNLYVKGEPIINYYDPLVFPSDEFDA
SISQVNEKINQSLAFIRKSDELLSAIGGYIPEAPRDGQAYVRKDGEWVLLSTFLGGLVPRGSHHHHHHSA
WSHPQFEK (SEQ ID NO:3)

Fig. 2A

>WT_RSV_F_Subtype(B) full-length (Accession# AHJ60043.1)

MELLIHRSSAIFLTLAINALYLTSSQNITEEFYQSTCSAVSRGYFSALRTGWYTSVITIELSNITETKCN
GTDTKVKLIKQELDKYKNAVTELQLLMQNTPAANNRARREAPQHMNYTINTTKNLNVSISKKRKRRFLGF
LLGVGSAIASGIAVSKVLHLEGEVNKIKNALLSTNKAVVSLSNGVSVLTSKVLDLKNYINNQLLPIVNQQ
SCRIFNIETVIEFQQKNSRLLEITREFSVNAGVTTPLSTYMLTNSELLSLINDMPITNDQKKLMSSNVQI
VRQQSYSIMSIIKEEVLAYVVQLPIYGVIDTPCWKLHTSPLCTTNIKEGSNICLTRTDRGWYCDNAGSVS
FFPQADTCKVQSNRVFCDTMNSLTLPSEVSLCNTDIFNSKYDCKIMTSKTDISSSVITSLGAIVSCYGKT
KCTASNKNRGIIKTFSNGCDYVSNKGVDTVSVGNTLYYVNKLEGKNLYVKGEPIINYYDPLVFPSDEFDA
SISQVNEKINQSLAFIRKSDELLHNVTGKSTTNIMITTIIIVIIVVLLSLIAIGLLLYCKAKNTPVTLS
KDQLSGINNIAFSK (SEQ ID NO:4)

Fig. 2B

```
>DS-Cav1 soluble
MELLILKANAITTILTAVTFCFASGQNITEEFYQSTCSAVSKGYLSALRTGWYTSVITIELSNIKENKCNGTDAKVK
LIKQELDKYKNAVTELQLLMQSTPATNNRARRELPRFMNYTLNNAKKTNVTLSKKRKRRFLGFLLGVGSAIASGVAV
CKVLHLEGEVNKIKSALLSTNKAVVSLSNGVSVLTFKVLDLKNYIDKQLLPILNKQSCSISNIETVIEFQQKNNRLL
EITREFSVNAGVTTPVSTYMLTNSELLSLINDMPITNDQKKLMSNNVQIVRQQSYSIMCIIKEEVLAYVVQLPLYGV
IDTPCWKLHTSPLCTTNTKEGSNICLTRTDRGWYCDNAGSVSFFPQAETCKVQSNRVFCDTMNSLTLPSEVNLCNVD
IFNPKYDCKIMTSKTDVSSSVITSLGAIVSCYGKTKCTASNKNRGIIKTFSNGCDYVSNKGVDTVSVGNTLYYVNKQ
EGKSLYVKGEPIINFYDPLVFPSDEFDASISQVNEKINQSLAFIRKSDELLSAIGGYIPEAPRDGQAYVRKDGEWVL
LSTFLGGLVPRGSHHHHHHSAWSHPQFEK (SEQ ID NO:5)
```

Fig. 3A

```
>DS_Cav1_full_length
MELLILKANAITTILTAVTFCFASGQNITEEFYQSTCSAVSKGYLSALRTGWYTSVITIELSNIKENKCNGTDAKVK
LIKQELDKYKNAVTELQLLMQSTPATNNRARRELPRFMNYTLNNAKKTNVTLSKKRKRRFLGFLLGVGSAIASGVAV
CKVLHLEGEVNKIKSALLSTNKAVVSLSNGVSVLTFKVLDLKNYIDKQLLPILNKQSCSISNIETVIEFQQKNNRLL
EITREFSVNAGVTTPVSTYMLTNSELLSLINDMPITNDQKKLMSNNVQIVRQQSYSIMCIIKEEVLAYVVQLPLYGV
IDTPCWKLHTSPLCTTNTKEGSNICLTRTDRGWYCDNAGSVSFFPQAETCKVQSNRVFCDTMNSLTLPSEVNLCNVD
IFNPKYDCKIMTSKTDVSSSVITSLGAIVSCYGKTKCTASNKNRGIIKTFSNGCDYVSNKGVDTVSVGNTLYYVNKQ
EGKSLYVKGEPIINFYDPLVFPSDEFDASISQVNEKINQSLAFIRKSDELLHNVTGKSTTNIMITTIIIVIIVVLL
SLIAIGLLLYCKAKNTPVTLSKDQLSGINNIAFSK (SEQ ID NO:6)
```

Fig. 3B

\>Cav1_soluble

MELLILKANAITTILTAVTFCFASGQNITEEFYQSTCSAVSKGYLSALRTGWYTSVITIELSNIKENKCNGTDAKVK
LIKQELDKYKNAVTELQLLMQSTPATNNRARRELPRFMNYTLNNAKKTNVTLSKKRKRRFLGFLLGVGSAIASGVAV
SKVLHLEGEVNKIKSALLSTNKAVVSLSNGVSVLTFKVLDLKNYIDKQLLPILNKQSCSISNIETVIEFQQKNNRLL
EITREFSVNAGVTTPVSTYMLTNSELLSLINDMPITNDQKKLMSNNVQIVRQQSYSIMSIIKEEVLAYVVQLPLYGV
IDTPCWKLHTSPLCTTNTKEGSNICLTRTDRGWYCDNAGSVSFFPQAETCKVQSNRVFCDTMNSLTLPSEVNLCNVD
IFNPKYDCKIMTSKTDVSSSVITSLGAIVSCYGKTKCTASNKNRGIIKTFSNGCDYVSNKGVDTVSVGNTLYYVNKQ
EGKSLYVKGEPIINFYDPLVFPSDEFDASISQVNEKINQSLAFIRKSDELLSAIGGYIPEAPRDGQAYVRKDGEWVL
LSTFLGGLVPRGSHHHHHHSAWSHPQFEK (SEQ ID NO:7)

Fig. 4A

\>Cav1_full_length

MELLILKANAITTILTAVTFCFASGQNITEEFYQSTCSAVSKGYLSALRTGWYTSVITIELSNIKENKCNGTDAKVK
LIKQELDKYKNAVTELQLLMQSTPATNNRARRELPRFMNYTLNNAKKTNVTLSKKRKRRFLGFLLGVGSAIASGVAV
SKVLHLEGEVNKIKSALLSTNKAVVSLSNGVSVLTFKVLDLKNYIDKQLLPILNKQSCSISNIETVIEFQQKNNRLL
EITREFSVNAGVTTPVSTYMLTNSELLSLINDMPITNDQKKLMSNNVQIVRQQSYSIMSIIKEEVLAYVVQLPLYGV
IDTPCWKLHTSPLCTTNTKEGSNICLTRTDRGWYCDNAGSVSFFPQAETCKVQSNRVFCDTMNSLTLPSEVNLCNVD
IFNPKYDCKIMTSKTDVSSSVITSLGAIVSCYGKTKCTASNKNRGIIKTFSNGCDYVSNKGVDTVSVGNTLYYVNKQ
EGKSLYVKGEPIINFYDPLVFPSDEFDASISQVNEKINQSLAFIRKSDELLHNVNTGKSTTNIMITTIIIVIIVVLL
SLIAIGLLLYCKAKNTPVTLSKDQLSGINNIAFSK (SEQ ID NO:8)

Fig. 4B

\>DS_soluble
MELLILKANAITTILTAVTFCFASGQNITEEFYQSTCSAVSKGYLSALRTGWYTSVITIELSNIKENKCNGTDAKVK
LIKQELDKYKNAVTELQLLMQSTPATNNRARRELPRFMNYTLNNAKKTNVTLSKKRKRRFLGFLLGVGSAIASGVAV
CKVLHLEGEVNKIKSALLSTNKAVVSLSNGVSVLTSKVLDLKNYIDKQLLPIVNKQSCSISNIETVIEFQQKNNRLL
EITREFSVNAGVTTPVSTYMLTNSELLSLINDMPITNDQKKLMSNNVQIVRQQSYSIMCIIKEEVLAYVVQLPLYGV
IDTPCWKLHTSPLCTTNTKEGSNICLTRTDRGWYCDNAGSVSFFPQAETCKVQSNRVFCDTMNSLTLPSEVNLCNVD
IFNPKYDCKIMTSKTDVSSSVITSLGAIVSCYGKTKCTASNKNRGIIKTFSNGCDYVSNKGVDTVSVGNTLYYVNKQ
EGKSLYVKGEPIINFYDPLVFPSDEFDASISQVNEKINQSLAFIRKSDELLSAIGGYIPEAPRDGQAYVRKDGEWVL
LSTFLGGLVPRGSHHHHHHSAWSHPQFEK (SEQ ID NO:9)

Fig. 5A

\>DS_full_length
MELLILKANAITTILTAVTFCFASGQNITEEFYQSTCSAVSKGYLSALRTGWYTSVITIELSNIKENKCNGTDAKVK
LIKQELDKYKNAVTELQLLMQSTPATNNRARRELPRFMNYTLNNAKKTNVTLSKKRKRRFLGFLLGVGSAIASGVAV
CKVLHLEGEVNKIKSALLSTNKAVVSLSNGVSVLTSKVLDLKNYIDKQLLPIVNKQSCSISNIETVIEFQQKNNRLL
EITREFSVNAGVTTPVSTYMLTNSELLSLINDMPITNDQKKLMSNNVQIVRQQSYSIMCIIKEEVLAYVVQLPLYGV
IDTPCWKLHTSPLCTTNTKEGSNICLTRTDRGWYCDNAGSVSFFPQAETCKVQSNRVFCDTMNSLTLPSEVNLCNVD
IFNPKYDCKIMTSKTDVSSSVITSLGAIVSCYGKTKCTASNKNRGIIKTFSNGCDYVSNKGVDTVSVGNTLYYVNKQ
EGKSLYVKGEPIINFYDPLVFPSDEFDASISQVNEKINQSLAFIRKSDELLHNVNTGKSTTNIMITTIIIVIIVVLL
SLIAIGLLLYCKAKNTPVTLSKDQLSGINNIAFSK (SEQ ID NO:10)

Fig. 5B

```
CLUSTAL 2.1 multiple sequence alignment

RSV_F_subtype_B_     MELLIHRSSAIFLTLAINALYLTSSQNITEEFYQSTCSAVSRGYFSALRTGWYTSVITIE 60
RSV_F_WT             MELLILKANAITTILTAVTFCFASGQNITEEFYQSTCSAVSKGYLSALRTGWYTSVITIE 60
                     *****  :: **    *:   ::   ::*.***********:**:***************

RSV_F_subtype_B_     LSNITETKCNGTDTKVKLIKQELDKYKNAVTELQLLMQNTPAANNRARREAPQHMNYTIN 120
RSV_F_WT             LSNIKENKCNGTDAKVKLIKQELDKYKNAVTELQLLMQSTPATNNRARRELPRFMNYTLN 120
                     ****.*.******:****************************.***:******* *:.****:*

RSV_F_subtype_B_     TTKNLNVSISKKRKRRFLGFLLGVGSALASGIAVSKVLHLEGEVNKIKNALLSTNKAVVS 180
RSV_F_WT             NAKKTNVTLSKKRKRRFLGFLLGVGSAIASGVAVSKVLHLEGEVNKIKSALLSTNKAVVS 180
                     .:*:  **::*****************:***:******************.*********

RSV_F_subtype_B_     LSNGVSVLTSKVLDLKNYINNQLLPIVNQQSCRIFNIETVIEFQQKNSRLLEITREFSVN 240
RSV_F_WT             LSNGVSVLTSKVLDLKNYIDKQLLPIVNKQSCSISNIETVIEFQQKNNRLLEITREFSVN 240
                     *******************::******:*** * ************.*************

RSV_F_subtype_B_     AGVTTPLSTYMLTNSELLSLINDMPITNDQKKLMSSNVQIVRQQSYSIMSIIKEEVLAYV 300
RSV_F_WT             AGVTTPVSTYMLTNSELLSLINDMPITNDQKKLMSNNVQIVRQQSYSIMSIIKEEVLAYV 300
                     ******:****************************.************************

RSV_F_subtype_B_     VQLPIYGVIDTPCWKLHTSPLCTTNIKEGSNICLTRTDRGWYCDNAGSVSFFPQADTCKV 360
RSV_F_WT             VQLPLYGVIDTPCWKLHTSPLCTTNTKEGSNICLTRTDRGWYCDNAGSVSFFPQAETCKV 360
                     ****:******************** *****************************:****

RSV_F_subtype_B_     QSNRVFCDTMNSLTLPSEVSLCNTDIFNSKYDCKIMTSKTDISSSVITSLGAIVSCYGKT 420
RSV_F_WT             QSNRVFCDTMNSLTLPSEVNLCNVDIFNPKYDCKIMTSKTDVSSSVITSLGAIVSCYGKT 420
                     *******************.***.****.***********:****************

RSV_F_subtype_B_     KCTASNKNRGIIKTFSNGCDYVSNKGVDTVSVGNTLYYVNKLEGKNLYVKGEPIINYYDP 480
RSV_F_WT             KCTASNKNRGIIKTFSNGCDYVSNKGVDTVSVGNTLYYVNKQEGKSLYVKGEPIINFYDP 480
                     *****************************************  *** .**********:***

RSV_F_subtype_B_     LVFPSDEFDASISQVNEKINQSLAFIRKSDELLHNVN-TGKSTTNIMITTIIIVIIVVLL 539
RSV_F_WT             LVFPSDEFDASISQVNEKINQSLAFIRKSDELLSAIGGYIPEAPRDGQAYVRKDGEWVLL 540
                     *********************************  :.    .:..   : :    ***

RSV_F_subtype_B_     SLIAIGLLLYCKAKNTPVTLSKDQLSGINNIAFSK 574
RSV_F_WT             STFLGGLVPRG--------SHHHHHHSAWSHPQFEK 568
                     * :  *:*:              : :.: *. .: *.*

Score: 80.99% identical
```

Fig. 6

```
CLUSTAL 2.1 multiple sequence alignment

RSV_F_subtypeA      MELLILKANAITTILTAVTFCFASGQNITEEFYQSTCSAVSKGYLSALRTGWYTSVITIE 60
RSV_F_subtypeB      MELLIHRSSAIFLTLAINALYLTSSQNITEEFYQSTCSAVSRGYFSALRTGWYTSVITIE 60
DS_Cav1             MELLILKANAITTILTAVTFCFASGQNITEEFYQSTCSAVSKGYLSALRTGWYTSVITIE 60
                    ***** :.** *: :: ::*.**********************:***************

RSV_F_subtypeA      LSNIKENKCNGTDAKVKLIKQELDKYKNAVTELQLLMQSTPATNNRARRELPRFMNYTLN 120
RSV_F_subtypeB      LSNITETKCNGTDTKVKLIKQELDKYKNAVTELQLLMQNTPAANNRARREAPQHMNYTIN 120
DS_Cav1             LSNIKENKCNGTDAKVKLIKQELDKYKNAVTELQLLMQSTPATNNRARRELPRFMNYTLN 120
                    ****.*.******:*******************.***:****:*******:.****:*

RSV_F_subtypeA      NAKKTNVTLSKKRKRRFLGFLLGVGSAIASGVAVCKVLHLEGEVNKIKSALLSTNKAVVS 180
RSV_F_subtypeB      TTKNLNVSISKKRKRRFLGFLLGVGSAIASGIAVSKVLHLEGEVNKIKNALLSTNKAVVS 180
DS_Cav1             NAKKTNVTLSKKRKRRFLGFLLGVGSAIASGVAVCKVLHLEGEVNKIKSALLSTNKAVVS 180
                    .:*: **::**********************:**.*************.**********

RSV_F_subtypeA      LSNGVSVLTFKVLDLKNYIDKQLLPILNKQSCSISNIETVIEFQQKNNRLLEITREFSVN 240
RSV_F_subtypeB      LSNGVSVLTSKVLDLKNYINNQLLPIVNQQSCRIFNIETVIEFQQKNSRLLEITREFSVN 240
DS_Cav1             LSNGVSVLTFKVLDLKNYIDKQLLPILNKQSCSISNIETVIEFQQKNNRLLEITREFSVN 240
                    ********* *********::*****:*:*** *.***********.*************

RSV_F_subtypeA      AGVTTPVSTYMLTNSELLSLINDMPITNDQKKLMSNNVQIVRQQSYSIMCIIKEEVLAYV 300
RSV_F_subtypeB      AGVTTPLSTYMLTNSELLSLINDMPITNDQKKLMSSNVQIVRQQSYSIMSIIKEEVLAYV 300
DS_Cav1             AGVTTPVSTYMLTNSELLSLINDMPITNDQKKLMSNNVQIVRQQSYSIMCIIKEEVLAYV 300
                    ******:****************************.*************.**********

RSV_F_subtypeA      VQLPLYGVIDTPCWKLHTSPLCTTNTKEGSNICLTRTDRGWYCDNAGSVSFFPQAETCKV 360
RSV_F_subtypeB      VQLPIYGVIDTPCWKLHTSPLCTTNIKEGSNICLTRTDRGWYCDNAGSVSFFPQADTCKV 360
DS_Cav1             VQLPLYGVIDTPCWKLHTSPLCTTNTKEGSNICLTRTDRGWYCDNAGSVSFFPQAETCKV 360
                    ****:*******************.***********************:****

RSV_F_subtypeA      QSNRVFCDTMNSLTLPSEVNLCNVDIFNPKYDCKIMTSKTDVSSSVITSLGAIVSCYGKT 420
RSV_F_subtypeB      QSNRVFCDTMNSLTLPSEVSLCNTDIFNSKYDCKIMTSKTDISSSVITSLGAIVSCYGKT 420
DS_Cav1             QSNRVFCDTMNSLTLPSEVNLCNVDIFNPKYDCKIMTSKTDVSSSVITSLGAIVSCYGKT 420
                    *******************.***.****.***********:*******************

RSV_F_subtypeA      KCTASNKNRGIIKTFSNGCDYVSNKGVDTVSVGNTLYYVNKQEGKSLYVKGEPIINFYDP 480
RSV_F_subtypeB      KCTASNKNRGIIKTFSNGCDYVSNKGVDTVSVGNTLYYVNKLEGKNLYVKGEPIINYYDP 480
DS_Cav1             KCTASNKNRGIIKTFSNGCDYVSNKGVDTVSVGNTLYYVNKQEGKSLYVKGEPIINFYDP 480
                    *****************************************.***.*********:****

RSV_F_subtypeA      LVFPSDEFDASISQVNEKINQSLAFIRKSDELLSAIGGYIPEAPRDGQAYVRKDGEWVLL 540
RSV_F_subtypeB      LVFPSDEFDASISQVNEKINQSLAFIRKSDELLHNVN-TGKSTTNIMITTIIIVIIVVLL 539
DS_Cav1             LVFPSDEFDASISQVNEKINQSLAFIRKSDELLSAIGGYIPEAPRDGQAYVRKDGEWVLL 540
                    *********************************  :.    .:..   : :    ***

RSV_F_subtypeA      STFLGGLVPRG-------SHHHHHHSAWSHPQFEK 568
RSV_F_subtypeB      SLIAIGLLLYCKAKNTPVTLSKDQLSGINNIAFSK 574
DS_Cav1             STFLGGLVPRG-------SHHHHHHSAWSHPQFEK 568
                    * : **:          : :.: *. .:  *.*
```

Fig. 7

>RSV_F_A147Y

MELLILKANAITTILTAVTFCFASGQNITEEFYQSTCSAVSKGYLSALRTGWYTSVITIELSNIKENKCNGTDAKVK
LIKQELDKYKNAVTELQLLMQSTPATNNRARRELPRFMNYTLNNAKKTNVTLSKKRKRRFLGFLLGVGSYIASGVAV
SKVLHLEGEVNKIKSALLSTNKAVVSLSNGVSVLTSKVLDLKNYIDKQLLPIVNKQSCSISNIETVIEFQQKNNRLL
EITREFSVNAGVTTPVSTYMLTNSELLSLINDMPITNDQKKLMSNNVQIVRQQSYSIMSIIKEEVLAYVVQLPLYGV
IDTPCWKLHTSPLCTTNTKEGSNICLTRTDRGWYCDNAGSVSFFPQAETCKVQSNRVFCDTMNSLTLPSEVNLCNVD
IFNPKYDCKIMTSKTDVSSSVITSLGAIVSCYGKTKCTASNKNRGIIKTFSNGCDYVSNKGVDTVSVGNTLYYVNKQ
EGKSLYVKGEPIINFYDPLVFPSDEFDASISQVNEKINQSLAFIRKSDELLSAIGGYIPEAPRDGQAYVRKDGEWVL
LSTFLGGLVPRGSHHHHHHSAWSHPQFEK (SEQ ID NO:11)

Fig. 8

>RSV_F_V220Y

MELLILKANAITTILTAVTFCFASGQNITEEFYQSTCSAVSKGYLSALRTGWYTSVITIELSNIKENKCNGTDAKVK
LIKQELDKYKNAVTELQLLMQSTPATNNRARRELPRFMNYTLNNAKKTNVTLSKKRKRRFLGFLLGVGSAIASGVAV
SKVLHLEGEVNKIKSALLSTNKAVVSLSNGVSVLTSKVLDLKNYIDKQLLPIVNKQSCSISNIETYIEFQQKNNRLL
EITREFSVNAGVTTPVSTYMLTNSELLSLINDMPITNDQKKLMSNNVQIVRQQSYSIMSIIKEEVLAYVVQLPLYGV
IDTPCWKLHTSPLCTTNTKEGSNICLTRTDRGWYCDNAGSVSFFPQAETCKVQSNRVFCDTMNSLTLPSEVNLCNVD
IFNPKYDCKIMTSKTDVSSSVITSLGAIVSCYGKTKCTASNKNRGIIKTFSNGCDYVSNKGVDTVSVGNTLYYVNKQ
EGKSLYVKGEPIINFYDPLVFPSDEFDASISQVNEKINQSLAFIRKSDELLSAIGGYIPEAPRDGQAYVRKDGEWVL
LSTFLGGLVPRGSHHHHHHSAWSHPQFEK (SEQ ID NO:12)

Fig. 9

>RSV_F_E222Y

MELLILKANAITTILTAVTFCFASGQNITEEFYQSTCSAVSKGYLSALRTGWYTSVITIELSNIKENKCNGTDAKVK
LIKQELDKYKNAVTELQLLMQSTPATNNRARRELPRFMNYTLNNAKKTNVTLSKKRKRRFLGFLLGVGSAIASGVAV
SKVLHLEGEVNKIKSALLSTNKAVVSLSNGVSVLTSKVLDLKNYIDKQLLPIVNKQSCSISNIETVIYFQQKNNRLL
EITREFSVNAGVTTPVSTYMLTNSELLSLINDMPITNDQKKLMSNNVQIVRQQSYSIMSIIKEEVLAYVVQLPLYGV
IDTPCWKLHTSPLCTTNTKEGSNICLTRTDRGWYCDNAGSVSFFPQAETCKVQSNRVFCDTMNSLTLPSEVNLCNVD
IFNPKYDCKIMTSKTDVSSSVITSLGAIVSCYGKTKCTASNKNRGIIKTFSNGCDYVSNKGVDTVSVGNTLYYVNKQ
EGKSLYVKGEPIINFYDPLVFPSDEFDASISQVNEKINQSLAFIRKSDELLSAIGGYIPEAPRDGQAYVRKDGEWVL
LSTFLGGLVPRGSHHHHHHSAWSHPQFEK (SEQ ID NO:13)

Fig. 10

>RSV_F_F223Y

MELLILKANAITTILTAVTFCFASGQNITEEFYQSTCSAVSKGYLSALRTGWYTSVITIELSNIKENKCNGTDAKVK
LIKQELDKYKNAVTELQLLMQSTPATNNRARRELPRFMNYTLNNAKKTNVTLSKKRKRRFLGFLLGVGSAIASGVAV
SKVLHLEGEVNKIKSALLSTNKAVVSLSNGVSVLTSKVLDLKNYIDKQLLPIVNKQSCSISNIETVIEYQQKNNRLL
EITREFSVNAGVTTPVSTYMLTNSELLSLINDMPITNDQKKLMSNNVQIVRQQSYSIMSIIKEEVLAYVVQLPLYGV
IDTPCWKLHTSPLCTTNTKEGSNICLTRTDRGWYCDNAGSVSFFPQAETCKVQSNRVFCDTMNSLTLPSEVNLCNVD
IFNPKYDCKIMTSKTDVSSSVITSLGAIVSCYGKTKCTASNKNRGIIKTFSNGCDYVSNKGVDTVSVGNTLYYVNKQ
EGKSLYVKGEPIINFYDPLVFPSDEFDASISQVNEKINQSLAFIRKSDELLSAIGGYIPEAPRDGQAYVRKDGEWVL
LSTFLGGLVPRGSHHHHHHSAWSHPQFEK (SEQ ID NO:14)

Fig. 11

>RSV_F_K226Y

MELLILKANAITTILTAVTFCFASGQNITEEFYQSTCSAVSKGYLSALRTGWYTSVITIELSNIKENKCNGTDAKVK
LIKQELDKYKNAVTELQLLMQSTPATNNRARRELPRFMNYTLNNAKKTNVTLSKKRKRRFLGFLLGVGSAIASGVAV
SKVLHLEGEVNKIKSALLSTNKAVVSLSNGVSVLTSKVLDLKNYIDKQLLPIVNKQSCSISNIETVIEFQQYNNRLL
EITREFSVNAGVTTPVSTYMLTNSELLSLINDMPITNDQKKLMSNNVQIVRQQSYSIMSIIKEEVLAYVVQLPLYGV
IDTPCWKLHTSPLCTTNTKEGSNICLTRTDRGWYCDNAGSVSFFPQAETCKVQSNRVFCDTMNSLTLPSEVNLCNVD
IFNPKYDCKIMTSKTDVSSSVITSLGAIVSCYGKTKCTASNKNRGIIKTFSNGCDYVSNKGVDTVSVGNTLYYVNKQ
EGKSLYVKGEPIINFYDPLVFPSDEFDASISQVNEKINQSLAFIRKSDELLSAIGGYIPEAPRDGQAYVRKDGEWVL
LSTFLGGLVPRGSHHHHHHSAWSHPQFEK (SEQ ID NO:15)

Fig. 12

>RSV_F_V469Y

MELLILKANAITTILTAVTFCFASGQNITEEFYQSTCSAVSKGYLSALRTGWYTSVITIELSNIKENKCNGTDAKVK
LIKQELDKYKNAVTELQLLMQSTPATNNRARRELPRFMNYTLNNAKKTNVTLSKKRKRRFLGFLLGVGSAIASGVAV
SKVLHLEGEVNKIKSALLSTNKAVVSLSNGVSVLTSKVLDLKNYIDKQLLPIVNKQSCSISNIETVIEFQQKNNRLL
EITREFSVNAGVTTPVSTYMLTNSELLSLINDMPITNDQKKLMSNNVQIVRQQSYSIMSIIKEEVLAYVVQLPLYGV
IDTPCWKLHTSPLCTTNTKEGSNICLTRTDRGWYCDNAGSVSFFPQAETCKVQSNRVFCDTMNSLTLPSEVNLCNVD
IFNPKYDCKIMTSKTDVSSSVITSLGAIVSCYGKTKCTASNKNRGIIKTFSNGCDYVSNKGVDTVSVGNTLYYVNKQ
EGKSLYYKGEPIINFYDPLVFPSDEFDASISQVNEKINQSLAFIRKSDELLSAIGGYIPEAPRDGQAYVRKDGEWVL
LSTFLGGLVPRGSHHHHHHSAWSHPQFEK (SEQ ID NO:16)

Fig. 13

>RSV_F_K77Y_E222Y

MELLILKANAITTILTAVTFCFASGQNITEEFYQSTCSAVSKGYLSALRTGWYTSVITIELSNIKENKCNGTDAKVY
LIKQELDKYKNAVTELQLLMQSTPATNNRARRELPRFMNYTLNNAKKTNVTLSKKRKRRFLGFLLGVGSAIASGVAV
SKVLHLEGEVNKIKSALLSTNKAVVSLSNGVSVLTSKVLDLKNYIDKQLLPIVNKQSCSISNIETVIYFQQKNNRLL
EITREFSVNAGVTTPVSTYMLTNSELLSLINDMPITNDQKKLMSNNVQIVRQQSYSIMSIIKEEVLAYVVQLPLYGV
IDTPCWKLHTSPLCTTNTKEGSNICLTRTDRGWYCDNAGSVSFFPQAETCKVQSNRVFCDTMNSLTLPSEVNLCNVD
IFNPKYDCKIMTSKTDVSSSVITSLGAIVSCYGKTKCTASNKNRGIIKTFSNGCDYVSNKGVDTVSVGNTLYYVNKQ
EGKSLYVKGEPIINFYDPLVFPSDEFDASISQVNEKINQSLAFIRKSDELLSAIGGYIPEAPRDGQAYVRKDGEWVL
LSTFLGGLVPRGSHHHHHHSAWSHPQFEK (SEQ ID NO:17)

Fig. 14

>RSV_F_N88Y_S255Y

MELLILKANAITTILTAVTFCFASGQNITEEFYQSTCSAVSKGYLSALRTGWYTSVITIELSNIKENKCNGTDAKVK
LIKQELDKYKYAVTELQLLMQSTPATNNRARRELPRFMNYTLNNAKKTNVTLSKKRKRRFLGFLLGVGSAIASGVAV
SKVLHLEGEVNKIKSALLSTNKAVVSLSNGVSVLTSKVLDLKNYIDKQLLPIVNKQSCSISNIETVIEFQQKNNRLL
EITREFSVNAGVTTPVSTYMLTNYELLSLINDMPITNDQKKLMSNNVQIVRQQSYSIMSIIKEEVLAYVVQLPLYGV
IDTPCWKLHTSPLCTTNTKEGSNICLTRTDRGWYCDNAGSVSFFPQAETCKVQSNRVFCDTMNSLTLPSEVNLCNVD
IFNPKYDCKIMTSKTDVSSSVITSLGAIVSCYGKTKCTASNKNRGIIKTFSNGCDYVSNKGVDTVSVGNTLYYVNKQ
EGKSLYVKGEPIINFYDPLVFPSDEFDASISQVNEKINQSLAFIRKSDELLSAIGGYIPEAPRDGQAYVRKDGEWVL
LSTFLGGLVPRGSHHHHHHSAWSHPQFEK (SEQ ID NO:18)

Fig. 15

>RSV_F_M97Y_H159Y

MELLILKANAITTILTAVTFCFASGQNITEEFYQSTCSAVSKGYLSALRTGWYTSVITIELSNIKENKCNGTDAKVK
LIKQELDKYKNAVTELQLLYQSTPATNNRARRELPRFMNYTLNNAKKTNVTLSKKRKRRFLGFLLGVGSAIASGVAV
SKVLYLEGEVNKIKSALLSTNKAVVSLSNGVSVLTSKVLDLKNYIDKQLLPIVNKQSCSISNIETVIEFQQKNNRLL
EITREFSVNAGVTTPVSTYMLTNSELLSLINDMPITNDQKKLMSNNVQIVRQQSYSIMSIIKEEVLAYVVQLPLYGV
IDTPCWKLHTSPLCTTNTKEGSNICLTRTDRGWYCDNAGSVSFFPQAETCKVQSNRVFCDTMNSLTLPSEVNLCNVD
IFNPKYDCKIMTSKTDVSSSVITSLGAIVSCYGKTKCTASNKNRGIIKTFSNGCDYVSNKGVDTVSVGNTLYYVNKQ
EGKSLYVKGEPIINFYDPLVFPSDEFDASISQVNEKINQSLAFIRKSDELLSAIGGYIPEAPRDGQAYVRKDGEWVL
LSTFLGGLVPRGSHHHHHHSAWSHPQFEK (SEQ ID NO:19)

Fig. 16

>RSV_F_V185Y_K427Y

MELLILKANAITTILTAVTFCFASGQNITEEFYQSTCSAVSKGYLSALRTGWYTSVITIELSNIKENKCNGTDAKVK
LIKQELDKYKNAVTELQLLMQSTPATNNRARRELPRFMNYTLNNAKKTNVTLSKKRKRRFLGFLLGVGSAIASGVAV
SKVLHLEGEVNKIKSALLSTNKAVVSLSNGYSVLTSKVLDLKNYIDKQLLPIVNKQSCSISNIETVIEFQQKNNRLL
EITREFSVNAGVTTPVSTYMLTNSELLSLINDMPITNDQKKLMSNNVQIVRQQSYSIMSIIKEEVLAYVVQLPLYGV
IDTPCWKLHTSPLCTTNTKEGSNICLTRTDRGWYCDNAGSVSFFPQAETCKVQSNRVFCDTMNSLTLPSEVNLCNVD
IFNPKYDCKIMTSKTDVSSSVITSLGAIVSCYGKTKCTASNYNRGIIKTFSNGCDYVSNKGVDTVSVGNTLYYVNKQ
EGKSLYVKGEPIINFYDPLVFPSDEFDASISQVNEKINQSLAFIRKSDELLSAIGGYIPEAPRDGQAYVRKDGEWVL
LSTFLGGLVPRGSHHHHHHSAWSHPQFEK (SEQ ID NO:20)

Fig. 17

>RSV_F_V187Y_K427Y

MELLILKANAITTILTAVTFCFASGQNITEEFYQSTCSAVSKGYLSALRTGWYTSVITIELSNIKENKCNGTDAKVK
LIKQELDKYKNAVTELQLLMQSTPATNNRARRELPRFMNYTLNNAKKTNVTLSKKRKRRFLGFLLGVGSAIASGVAV
SKVLHLEGEVNKIKSALLSTNKAVVSLSNGVSYLTSKVLDLKNYIDKQLLPIVNKQSCSISNIETVIEFQQKNNRLL
EITREFSVNAGVTTPVSTYMLTNSELLSLINDMPITNDQKKLMSNNVQIVRQQSYSIMSIIKEEVLAYVVQLPLYGV
IDTPCWKLHTSPLCTTNTKEGSNICLTRTDRGWYCDNAGSVSFFPQAETCKVQSNRVFCDTMNSLTLPSEVNLCNVD
IFNPKYDCKIMTSKTDVSSSVITSLGAIVSCYGKTKCTASNYNRGIIKTFSNGCDYVSNKGVDTVSVGNTLYYVNKQ
EGKSLYVKGEPIINFYDPLVFPSDEFDASISQVNEKINQSLAFIRKSDELLSAIGGYIPEAPRDGQAYVRKDGEWVL
LSTFLGGLVPRGSHHHHHHSAWSHPQFEK (SEQ ID NO:21)

Fig. 18

>RSV_F N183Y_K427Y

MELLILKANAITTILTAVTFCFASGQNITEEFYQSTCSAVSKGYLSALRTGWYTSVITIELSNIKENKCNGTDAKVK
LIKQELDKYKNAVTELQLLMQSTPATNNRARRELPRFMNYTLNNAKKTNVTLSKKRKRRFLGFLLGVGSAIASGVAV
SKVLHLEGEVNKIKSALLSTNKAVVSLSYGVSVLTSKVLDLKNYIDKQLLPIVNKQSCSISNIETVIEFQQKNNRLL
EITREFSVNAGVTTPVSTYMLTNSELLSLINDMPITNDQKKLMSNNVQIVRQQSYSIMSIIKEEVLAYVVQLPLYGV
IDTPCWKLHTSPLCTTNTKEGSNICLTRTDRGWYCDNAGSVSFFPQAETCKVQSNRVFCDTMNSLTLPSEVNLCNVD
IFNPKYDCKIMTSKTDVSSSVITSLGAIVSCYGKTKCTASNYNRGIIKTFSNGCDYVSNKGVDTVSVGNTLYYVNKQ
EGKSLYVKGEPIINFYDPLVFPSDEFDASISQVNEKINQSLAFIRKSDELLSAIGGYIPEAPRDGQAYVRKDGEWVL
LSTFLGGLVPRGSHHHHHHSAWSHPQFEK (SEQ ID NO:22)

Fig. 19

CLUSTAL 2.1 multiple sequence alignment

```
RSV_F_WT           MELLILKANAITTILTAVTFCFASGQNITEEFYQSTCSAVSKGYLSALRTGWYTSVITIE 60
RSV_F_A147Y        MELLILKANAITTILTAVTFCFASGQNITEEFYQSTCSAVSKGYLSALRTGWYTSVITIE 60
RSV_F_V220Y        MELLILKANAITTILTAVTFCFASGQNITEEFYQSTCSAVSKGYLSALRTGWYTSVITIE 60
RSV_F_E222Y        MELLILKANAITTILTAVTFCFASGQNITEEFYQSTCSAVSKGYLSALRTGWYTSVITIE 60
RSV_F_F223Y        MELLILKANAITTILTAVTFCFASGQNITEEFYQSTCSAVSKGYLSALRTGWYTSVITIE 60
RSV_F_K226Y        MELLILKANAITTILTAVTFCFASGQNITEEFYQSTCSAVSKGYLSALRTGWYTSVITIE 60
RSV_F_V469Y        MELLILKANAITTILTAVTFCFASGQNITEEFYQSTCSAVSKGYLSALRTGWYTSVITIE 60
RSV_F_K77Y_E222Y   MELLILKANAITTILTAVTFCFASGQNITEEFYQSTCSAVSKGYLSALRTGWYTSVITIE 60
RSV_F_N88Y_S255Y   MELLILKANAITTILTAVTFCFASGQNITEEFYQSTCSAVSKGYLSALRTGWYTSVITIE 60
RSV_F_M97Y_H159Y   MELLILKANAITTILTAVTFCFASGQNITEEFYQSTCSAVSKGYLSALRTGWYTSVITIE 60
RSV_F_V185Y_K427Y  MELLILKANAITTILTAVTFCFASGQNITEEFYQSTCSAVSKGYLSALRTGWYTSVITIE 60
RSV_F_V187Y_K427Y  MELLILKANAITTILTAVTFCFASGQNITEEFYQSTCSAVSKGYLSALRTGWYTSVITIE 60
                   ************************************************************

RSV_F_WT           LSNIKENKCNGTDAKVKLIKQELDKYKNAVTELQLLMQSTPATNNRARRELPRFMNYTLN 120
RSV_F_A147Y        LSNIKENKCNGTDAKVKLIKQELDKYKNAVTELQLLMQSTPATNNRARRELPRFMNYTLN 120
RSV_F_V220Y        LSNIKENKCNGTDAKVKLIKQELDKYKNAVTELQLLMQSTPATNNRARRELPRFMNYTLN 120
RSV_F_E222Y        LSNIKENKCNGTDAKVKLIKQELDKYKNAVTELQLLMQSTPATNNRARRELPRFMNYTLN 120
RSV_F_F223Y        LSNIKENKCNGTDAKVKLIKQELDKYKNAVTELQLLMQSTPATNNRARRELPRFMNYTLN 120
RSV_F_K226Y        LSNIKENKCNGTDAKVKLIKQELDKYKNAVTELQLLMQSTPATNNRARRELPRFMNYTLN 120
RSV_F_V469Y        LSNIKENKCNGTDAKVKLIKQELDKYKNAVTELQLLMQSTPATNNRARRELPRFMNYTLN 120
RSV_F_K77Y_E222Y   LSNIKENKCNGTDAKVYLIKQELDKYKNAVTELQLLMQSTPATNNRARRELPRFMNYTLN 120
RSV_F_N88Y_S255Y   LSNIKENKCNGTDAKVKLIKQELDKYYAVTELQLLMQSTPATNNRARRELPRFMNYTLN 120
RSV_F_M97Y_H159Y   LSNIKENKCNGTDAKVKLIKQELDKYKNAVTELQLYQSTPATNNRARRELPRFMNYTLN 120
RSV_F_V185Y_K427Y  LSNIKENKCNGTDAKVKLIKQELDKYKNAVTELQLLMQSTPATNNRARRELPRFMNYTLN 120
RSV_F_V187Y_K427Y  LSNIKENKCNGTDAKVKLIKQELDKYKNAVTELQLLMQSTPATNNRARRELPRFMNYTLN 120
                   **************** ********* ******* ************************

RSV_F_WT           NAKKTNVTLSKKRKRRFLGFLLGVGSAIASGVAVSKVLHLEGEVNKIKSALLSTNKAVVS 180
RSV_F_A147Y        NAKKTNVTLSKKRKRRFLGFLLGVGSYIASGVAVSKVLHLEGEVNKIKSALLSTNKAVVS 180
RSV_F_V220Y        NAKKTNVTLSKKRKRRFLGFLLGVGSAIASGVAVSKVLHLEGEVNKIKSALLSTNKAVVS 180
RSV_F_E222Y        NAKKTNVTLSKKRKRRFLGFLLGVGSAIASGVAVSKVLHLEGEVNKIKSALLSTNKAVVS 180
RSV_F_F223Y        NAKKTNVTLSKKRKRRFLGFLLGVGSAIASGVAVSKVLHLEGEVNKIKSALLSTNKAVVS 180
RSV_F_K226Y        NAKKTNVTLSKKRKRRFLGFLLGVGSAIASGVAVSKVLHLEGEVNKIKSALLSTNKAVVS 180
RSV_F_V469Y        NAKKTNVTLSKKRKRRFLGFLLGVGSAIASGVAVSKVLHLEGEVNKIKSALLSTNKAVVS 180
RSV_F_K77Y_E222Y   NAKKTNVTLSKKRKRRFLGFLLGVGSAIASGVAVSKVLHLEGEVNKIKSALLSTNKAVVS 180
RSV_F_N88Y_S255Y   NAKKTNVTLSKKRKRRFLGFLLGVGSAIASGVAVSKVLHLEGEVNKIKSALLSTNKAVVS 180
RSV_F_M97Y_H159Y   NAKKTNVTLSKKRKRRFLGFLLGVGSAIASGVAVSKVYLEGEVNKIKSALLSTNKAVVS 180
RSV_F_V185Y_K427Y  NAKKTNVTLSKKRKRRFLGFLLGVGSAIASGVAVSKVLHLEGEVNKIKSALLSTNKAVVS 180
RSV_F_V187Y_K427Y  NAKKTNVTLSKKRKRRFLGFLLGVGSAIASGVAVSKVLHLEGEVNKIKSALLSTNKAVVS 180
                   ************************* *********** .********************

RSV_F_WT           LSNGVSVLTSKVLDLKNYIDKQLLPIVNKQSCSISNIETVIEFQQKNNRLLEITREFSVN 240
RSV_F_A147Y        LSNGVSVLTSKVLDLKNYIDKQLLPIVNKQSCSISNIETVIEFQQKNNRLLEITREFSVN 240
RSV_F_V220Y        LSNGVSVLTSKVLDLKNYIDKQLLPIVNKQSCSISNIETYIEFQQKNNRLLEITREFSVN 240
RSV_F_E222Y        LSNGVSVLTSKVLDLKNYIDKQLLPIVNKQSCSISNIETVIYFQQKNNRLLEITREFSVN 240
RSV_F_F223Y        LSNGVSVLTSKVLDLKNYIDKQLLPIVNKQSCSISNIETVIEYQQKNNRLLEITREFSVN 240
RSV_F_K226Y        LSNGVSVLTSKVLDLKNYIDKQLLPIVNKQSCSISNIETVIEFQQYNNRLLEITREFSVN 240
RSV_F_V469Y        LSNGVSVLTSKVLDLKNYIDKQLLPIVNKQSCSISNIETVIEFQQKNNRLLEITREFSVN 240
RSV_F_K77Y_E222Y   LSNGVSVLTSKVLDLKNYIDKQLLPIVNKQSCSISNIETVIYFQQKNNRLLEITREFSVN 240
RSV_F_N88Y_S255Y   LSNGVSVLTSKVLDLKNYIDKQLLPIVNKQSCSISNIETVIEFQQKNNRLLEITREFSVN 240
RSV_F_M97Y_H159Y   LSNGVSVLTSKVLDLKNYIDKQLLPIVNKQSCSISNIETVIEFQQKNNRLLEITREFSVN 240
RSV_F_V185Y_K427Y  LSNGYSVLTSKVLDLKNYIDKQLLPIVNKQSCSISNIETVIEFQQKNNRLLEITREFSVN 240
RSV_F_V187Y_K427Y  LSNGVSYLTSKVLDLKNYIDKQLLPIVNKQSCSISNIETVIEFQQKNNRLLEITREFSVN 240
                   **** ********************************** *.** **************
```

Fig. 20A

```
RSV_F_WT          AGVTTPVSTYMLTNSELLSLINDMPITNDQKKLMSNNVQIVRQQSYSIMSIIKEEVLAYV 300
RSV_F_A147Y       AGVTTPVSTYMLTNSELLSLINDMPITNDQKKLMSNNVQIVRQQSYSIMSIIKEEVLAYV 300
RSV_F_V220Y       AGVTTPVSTYMLTNSELLSLINDMPITNDQKKLMSNNVQIVRQQSYSIMSIIKEEVLAYV 300
RSV_F_E222Y       AGVTTPVSTYMLTNSELLSLINDMPITNDQKKLMSNNVQIVRQQSYSIMSIIKEEVLAYV 300
RSV_F_F223Y       AGVTTPVSTYMLTNSELLSLINDMPITNDQKKLMSNNVQIVRQQSYSIMSIIKEEVLAYV 300
RSV_F_K226Y       AGVTTPVSTYMLTNSELLSLINDMPITNDQKKLMSNNVQIVRQQSYSIMSIIKEEVLAYV 300
RSV_F_V469Y       AGVTTPVSTYMLTNSELLSLINDMPITNDQKKLMSNNVQIVRQQSYSIMSIIKEEVLAYV 300
RSV_F_K77Y_E222Y  AGVTTPVSTYMLTNSELLSLINDMPITNDQKKLMSNNVQIVRQQSYSIMSIIKEEVLAYV 300
RSV_F_N88Y_S255Y  AGVTTPVSTYMLTNYELLSLINDMPITNDQKKLMSNNVQIVRQQSYSIMSIIKEEVLAYV 300
RSV_F_M97Y_H159Y  AGVTTPVSTYMLTNSELLSLINDMPITNDQKKLMSNNVQIVRQQSYSIMSIIKEEVLAYV 300
RSV_F_V185Y_K427Y AGVTTPVSTYMLTNSELLSLINDMPITNDQKKLMSNNVQIVRQQSYSIMSIIKEEVLAYV 300
RSV_F_V187Y_K427Y AGVTTPVSTYMLTNSELLSLINDMPITNDQKKLMSNNVQIVRQQSYSIMSIIKEEVLAYV 300
                  ************** *********************************************

RSV_F_WT          VQLPLYGVIDTPCWKLHTSPLCTTNTKEGSNICLTRTDRGWYCDNAGSVSFFPQAETCKV 360
RSV_F_A147Y       VQLPLYGVIDTPCWKLHTSPLCTTNTKEGSNICLTRTDRGWYCDNAGSVSFFPQAETCKV 360
RSV_F_V220Y       VQLPLYGVIDTPCWKLHTSPLCTTNTKEGSNICLTRTDRGWYCDNAGSVSFFPQAETCKV 360
RSV_F_E222Y       VQLPLYGVIDTPCWKLHTSPLCTTNTKEGSNICLTRTDRGWYCDNAGSVSFFPQAETCKV 360
RSV_F_F223Y       VQLPLYGVIDTPCWKLHTSPLCTTNTKEGSNICLTRTDRGWYCDNAGSVSFFPQAETCKV 360
RSV_F_K226Y       VQLPLYGVIDTPCWKLHTSPLCTTNTKEGSNICLTRTDRGWYCDNAGSVSFFPQAETCKV 360
RSV_F_V469Y       VQLPLYGVIDTPCWKLHTSPLCTTNTKEGSNICLTRTDRGWYCDNAGSVSFFPQAETCKV 360
RSV_F_K77Y_E222Y  VQLPLYGVIDTPCWKLHTSPLCTTNTKEGSNICLTRTDRGWYCDNAGSVSFFPQAETCKV 360
RSV_F_N88Y_S255Y  VQLPLYGVIDTPCWKLHTSPLCTTNTKEGSNICLTRTDRGWYCDNAGSVSFFPQAETCKV 360
RSV_F_M97Y_H159Y  VQLPLYGVIDTPCWKLHTSPLCTTNTKEGSNICLTRTDRGWYCDNAGSVSFFPQAETCKV 360
RSV_F_V185Y_K427Y VQLPLYGVIDTPCWKLHTSPLCTTNTKEGSNICLTRTDRGWYCDNAGSVSFFPQAETCKV 360
RSV_F_V187Y_K427Y VQLPLYGVIDTPCWKLHTSPLCTTNTKEGSNICLTRTDRGWYCDNAGSVSFFPQAETCKV 360
                  ************************************************************

RSV_F_WT          QSNRVFCDTMNSLTLPSEVNLCNVDIFNPKYDCKIMTSKTDVSSSVITSLGAIVSCYGKT 420
RSV_F_A147Y       QSNRVFCDTMNSLTLPSEVNLCNVDIFNPKYDCKIMTSKTDVSSSVITSLGAIVSCYGKT 420
RSV_F_V220Y       QSNRVFCDTMNSLTLPSEVNLCNVDIFNPKYDCKIMTSKTDVSSSVITSLGAIVSCYGKT 420
RSV_F_E222Y       QSNRVFCDTMNSLTLPSEVNLCNVDIFNPKYDCKIMTSKTDVSSSVITSLGAIVSCYGKT 420
RSV_F_F223Y       QSNRVFCDTMNSLTLPSEVNLCNVDIFNPKYDCKIMTSKTDVSSSVITSLGAIVSCYGKT 420
RSV_F_K226Y       QSNRVFCDTMNSLTLPSEVNLCNVDIFNPKYDCKIMTSKTDVSSSVITSLGAIVSCYGKT 420
RSV_F_V469Y       QSNRVFCDTMNSLTLPSEVNLCNVDIFNPKYDCKIMTSKTDVSSSVITSLGAIVSCYGKT 420
RSV_F_K77Y_E222Y  QSNRVFCDTMNSLTLPSEVNLCNVDIFNPKYDCKIMTSKTDVSSSVITSLGAIVSCYGKT 420
RSV_F_N88Y_S255Y  QSNRVFCDTMNSLTLPSEVNLCNVDIFNPKYDCKIMTSKTDVSSSVITSLGAIVSCYGKT 420
RSV_F_M97Y_H159Y  QSNRVFCDTMNSLTLPSEVNLCNVDIFNPKYDCKIMTSKTDVSSSVITSLGAIVSCYGKT 420
RSV_F_V185Y_K427Y QSNRVFCDTMNSLTLPSEVNLCNVDIFNPKYDCKIMTSKTDVSSSVITSLGAIVSCYGKT 420
RSV_F_V187Y_K427Y QSNRVFCDTMNSLTLPSEVNLCNVDIFNPKYDCKIMTSKTDVSSSVITSLGAIVSCYGKT 420
                  ************************************************************

RSV_F_WT          KCTASNKNRGIIKTFSNGCDYVSNKGVDTVSVGNTLYYVNKQEGKSLYVKGEPIINFYDP 480
RSV_F_A147Y       KCTASNKNRGIIKTFSNGCDYVSNKGVDTVSVGNTLYYVNKQEGKSLYVKGEPIINFYDP 480
RSV_F_V220Y       KCTASNKNRGIIKTFSNGCDYVSNKGVDTVSVGNTLYYVNKQEGKSLYVKGEPIINFYDP 480
RSV_F_E222Y       KCTASNKNRGIIKTFSNGCDYVSNKGVDTVSVGNTLYYVNKQEGKSLYVKGEPIINFYDP 480
RSV_F_F223Y       KCTASNKNRGIIKTFSNGCDYVSNKGVDTVSVGNTLYYVNKQEGKSLYVKGEPIINFYDP 480
RSV_F_K226Y       KCTASNKNRGIIKTFSNGCDYVSNKGVDTVSVGNTLYYVNKQEGKSLYVKGEPIINFYDP 480
RSV_F_V469Y       KCTASNKNRGIIKTFSNGCDYVSNKGVDTVSVGNTLYYVNKQEGKSLYVKGEPIINFYDP 480
RSV_F_K77Y_E222Y  KCTASNKNRGIIKTFSNGCDYVSNKGVDTVSVGNTLYYVNKQEGKSLYVKGEPIINFYDP 480
RSV_F_N88Y_S255Y  KCTASNKNRGIIKTFSNGCDYVSNKGVDTVSVGNTLYYVNKQEGKSLYVKGEPIINFYDP 480
RSV_F_M97Y_H159Y  KCTASNKNRGIIKTFSNGCDYVSNKGVDTVSVGNTLYYVNKQEGKSLYVKGEPIINFYDP 480
RSV_F_V185Y_K427Y KCTASNYNRGIIKTFSNGCDYVSNKGVDTVSVGNTLYYVNKQEGKSLYVKGEPIINFYDP 480
RSV_F_V187Y_K427Y KCTASNYNRGIIKTFSNGCDYVSNKGVDTVSVGNTLYYVNKQEGKSLYVKGEPIINFYDP 480
                  ***** ****************************************** **********
```

Fig. 20B

```
RSV_F_WT            LVFPSDEFDASISQVNEKINQSLAFIRKSDELLSAIGGYIPEAPRDGQAYVRKDGEWVLL 540
RSV_F_A147Y         LVFPSDEFDASISQVNEKINQSLAFIRKSDELLSAIGGYIPEAPRDGQAYVRKDGEWVLL 540
RSV_F_V220Y         LVFPSDEFDASISQVNEKINQSLAFIRKSDELLSAIGGYIPEAPRDGQAYVRKDGEWVLL 540
RSV_F_E222Y         LVFPSDEFDASISQVNEKINQSLAFIRKSDELLSAIGGYIPEAPRDGQAYVRKDGEWVLL 540
RSV_F_F223Y         LVFPSDEFDASISQVNEKINQSLAFIRKSDELLSAIGGYIPEAPRDGQAYVRKDGEWVLL 540
RSV_F_K226Y         LVFPSDEFDASISQVNEKINQSLAFIRKSDELLSAIGGYIPEAPRDGQAYVRKDGEWVLL 540
RSV_F_V469Y         LVFPSDEFDASISQVNEKINQSLAFIRKSDELLSAIGGYIPEAPRDGQAYVRKDGEWVLL 540
RSV_F_K77Y_E222Y    LVFPSDEFDASISQVNEKINQSLAFIRKSDELLSAIGGYIPEAPRDGQAYVRKDGEWVLL 540
RSV_F_N88Y_S255Y    LVFPSDEFDASISQVNEKINQSLAFIRKSDELLSAIGGYIPEAPRDGQAYVRKDGEWVLL 540
RSV_F_M97Y_H159Y    LVFPSDEFDASISQVNEKINQSLAFIRKSDELLSAIGGYIPEAPRDGQAYVRKDGEWVLL 540
RSV_F_V185Y_K427Y   LVFPSDEFDASISQVNEKINQSLAFIRKSDELLSAIGGYIPEAPRDGQAYVRKDGEWVLL 540
RSV_F_V187Y_K427Y   LVFPSDEFDASISQVNEKINQSLAFIRKSDELLSAIGGYIPEAPRDGQAYVRKDGEWVLL 540
                    ************************************************************

RSV_F_WT            STFLGGLVPRGSHHHHHHSAWSHPQFEK 568
RSV_F_A147Y         STFLGGLVPRGSHHHHHHSAWSHPQFEK 568
RSV_F_V220Y         STFLGGLVPRGSHHHHHHSAWSHPQFEK 568
RSV_F_E222Y         STFLGGLVPRGSHHHHHHSAWSHPQFEK 568
RSV_F_F223Y         STFLGGLVPRGSHHHHHHSAWSHPQFEK 568
RSV_F_K226Y         STFLGGLVPRGSHHHHHHSAWSHPQFEK 568
RSV_F_V469Y         STFLGGLVPRGSHHHHHHSAWSHPQFEK 568
RSV_F_K77Y_E222Y    STFLGGLVPRGSHHHHHHSAWSHPQFEK 568
RSV_F_N88Y_S255Y    STFLGGLVPRGSHHHHHHSAWSHPQFEK 568
RSV_F_M97Y_H159Y    STFLGGLVPRGSHHHHHHSAWSHPQFEK 568
RSV_F_V185Y_K427Y   STFLGGLVPRGSHHHHHHSAWSHPQFEK 568
RSV_F_V187Y_K427Y   STFLGGLVPRGSHHHHHHSAWSHPQFEK 568
                    ***************************
```

Fig. 20C

>DS-Cav1_A147Y

MELLILKANAITTILTAVTFCFASGQNITEEFYQSTCSAVSKGYLSALRTGWYTSVITIELSNIKENKCNGTDAKVK
LIKQELDKYKNAVTELQLLMQSTPATNNRARRELPRFMNYTLNNAKKTNVTLSKKRKRRFLGFLLGVGSYIASGVAV
CKVLHLEGEVNKIKSALLSTNKAVVSLSNGVSVLTFKVLDLKNYIDKQLLPILNKQSCSISNIETVIEFQQKNNRLL
EITREFSVNAGVTTPVSTYMLTNSELLSLINDMPITNDQKKLMSNNVQIVRQQSYSIMCIIKEEVLAYVVQLPLYGV
IDTPCWKLHTSPLCTTNTKEGSNICLTRTDRGWYCDNAGSVSFFPQAETCKVQSNRVFCDTMNSLTLPSEVNLCNVD
IFNPKYDCKIMTSKTDVSSSVITSLGAIVSCYGKTKCTASNKNRGIIKTFSNGCDYVSNKGVDTVSVGNTLYYVNKQ
EGKSLYVKGEPIINFYDPLVFPSDEFDASISQVNEKINQSLAFIRKSDELLSAIGGYIPEAPRDQAYVRKDGEWVL
LSTFLGGLVPRGSHHHHHHSAWSHPQFEK (SEQ ID NO:23)

Fig. 21

>DS-Cav1_V220Y

MELLILKANAITTILTAVTFCFASGQNITEEFYQSTCSAVSKGYLSALRTGWYTSVITIELSNIKENKCNGTDAKVK
LIKQELDKYKNAVTELQLLMQSTPATNNRARRELPRFMNYTLNNAKKTNVTLSKKRKRRFLGFLLGVGSAIASGVAV
CKVLHLEGEVNKIKSALLSTNKAVVSLSNGVSVLTFKVLDLKNYIDKQLLPILNKQSCSISNIETYIEFQQKNNRLL
EITREFSVNAGVTTPVSTYMLTNSELLSLINDMPITNDQKKLMSNNVQIVRQQSYSIMCIIKEEVLAYVVQLPLYGV
IDTPCWKLHTSPLCTTNTKEGSNICLTRTDRGWYCDNAGSVSFFPQAETCKVQSNRVFCDTMNSLTLPSEVNLCNVD
IFNPKYDCKIMTSKTDVSSSVITSLGAIVSCYGKTKCTASNKNRGIIKTFSNGCDYVSNKGVDTVSVGNTLYYVNKQ
EGKSLYVKGEPIINFYDPLVFPSDEFDASISQVNEKINQSLAFIRKSDELLSAIGGYIPEAPRDQAYVRKDGEWVL
LSTFLGGLVPRGSHHHHHHSAWSHPQFEK (SEQ ID NO:24)

Fig. 22

>DS-Cav1_E222Y

MELLILKANAITTILTAVTFCFASGQNITEEFYQSTCSAVSKGYLSALRTGWYTSVITIELSNIKENKCNGTDAKVK
LIKQELDKYKNAVTELQLLMQSTPATNNRARRELPRFMNYTLNNAKKTNVTLSKKRKRRFLGFLLGVGSAIASGVAV
CKVLHLEGEVNKIKSALLSTNKAVVSLSNGVSVLTFKVLDLKNYIDKQLLPILNKQSCSISNIETVIYFQQKNNRLL
EITREFSVNAGVTTPVSTYMLTNSELLSLINDMPITNDQKKLMSNNVQIVRQQSYSIMCIIKEEVLAYVVQLPLYGV
IDTPCWKLHTSPLCTTNTKEGSNICLTRTDRGWYCDNAGSVSFFPQAETCKVQSNRVFCDTMNSLTLPSEVNLCNVD
IFNPKYDCKIMTSKTDVSSSVITSLGAIVSCYGKTKCTASNKNRGIIKTFSNGCDYVSNKGVDTVSVGNTLYYVNKQ
EGKSLYVKGEPIINFYDPLVFPSDEFDASISQVNEKINQSLAFIRKSDELLSAIGGYIPEAPRDQAYVRKDGEWVL
LSTFLGGLVPRGSHHHHHHSAWSHPQFEK (SEQ ID NO:25)

Fig. 23

>DS-Cav1_F223Y

MELLILKANAITTILTAVTFCFASGQNITEEFYQSTCSAVSKGYLSALRTGWYTSVITIELSNIKENKCNGTDAKVK
LIKQELDKYKNAVTELQLLMQSTPATNNRARRELPRFMNYTLNNAKKTNVTLSKKRKRRFLGFLLGVGSAIASGVAV
CKVLHLEGEVNKIKSALLSTNKAVVSLSNGVSVLTFKVLDLKNYIDKQLLPILNKQSCSISNIETVIEYQQKNNRLL
EITREFSVNAGVTTPVSTYMLTNSELLSLINDMPITNDQKKLMSNNVQIVRQQSYSIMCIIKEEVLAYVVQLPLYGV
IDTPCWKLHTSPLCTTNTKEGSNICLTRTDRGWYCDNAGSVSFFPQAETCKVQSNRVFCDTMNSLTLPSEVNLCNVD
IFNPKYDCKIMTSKTDVSSSVITSLGAIVSCYGKTKCTASNKNRGIIKTFSNGCDYVSNKGVDTVSVGNTLYYVNKQ
EGKSLYVKGEPIINFYDPLVFPSDEFDASISQVNEKINQSLAFIRKSDELLSAIGGYIPEAPRDGQAYVRKDGEWVL
LSTFLGGLVPRGSHHHHHHSAWSHPQFEK (SEQ ID NO:26)

Fig. 24

>DS-Cav1_K226Y

MELLILKANAITTILTAVTFCFASGQNITEEFYQSTCSAVSKGYLSALRTGWYTSVITIELSNIKENKCNGTDAKVK
LIKQELDKYKNAVTELQLLMQSTPATNNRARRELPRFMNYTLNNAKKTNVTLSKKRKRRFLGFLLGVGSAIASGVAV
CKVLHLEGEVNKIKSALLSTNKAVVSLSNGVSVLTFKVLDLKNYIDKQLLPILNKQSCSISNIETVIEFQQYNNRLL
EITREFSVNAGVTTPVSTYMLTNSELLSLINDMPITNDQKKLMSNNVQIVRQQSYSIMCIIKEEVLAYVVQLPLYGV
IDTPCWKLHTSPLCTTNTKEGSNICLTRTDRGWYCDNAGSVSFFPQAETCKVQSNRVFCDTMNSLTLPSEVNLCNVD
IFNPKYDCKIMTSKTDVSSSVITSLGAIVSCYGKTKCTASNKNRGIIKTFSNGCDYVSNKGVDTVSVGNTLYYVNKQ
EGKSLYVKGEPIINFYDPLVFPSDEFDASISQVNEKINQSLAFIRKSDELLSAIGGYIPEAPRDGQAYVRKDGEWVL
LSTFLGGLVPRGSHHHHHHSAWSHPQFEK (SEQ ID NO:27)

Fig. 25

>DS-Cav1_V469Y

MELLILKANAITTILTAVTFCFASGQNITEEFYQSTCSAVSKGYLSALRTGWYTSVITIELSNIKENKCNGTDAKVK
LIKQELDKYKNAVTELQLLMQSTPATNNRARRELPRFMNYTLNNAKKTNVTLSKKRKRRFLGFLLGVGSAIASGVAV
CKVLHLEGEVNKIKSALLSTNKAVVSLSNGVSVLTFKVLDLKNYIDKQLLPILNKQSCSISNIETVIEFQQKNNRLL
EITREFSVNAGVTTPVSTYMLTNSELLSLINDMPITNDQKKLMSNNVQIVRQQSYSIMCIIKEEVLAYVVQLPLYGV
IDTPCWKLHTSPLCTTNTKEGSNICLTRTDRGWYCDNAGSVSFFPQAETCKVQSNRVFCDTMNSLTLPSEVNLCNVD
IFNPKYDCKIMTSKTDVSSSVITSLGAIVSCYGKTKCTASNKNRGIIKTFSNGCDYVSNKGVDTVSVGNTLYYVNKQ
EGKSLYYKGEPIINFYDPLVFPSDEFDASISQVNEKINQSLAFIRKSDELLSAIGGYIPEAPRDGQAYVRKDGEWVL
LSTFLGGLVPRGSHHHHHHSAWSHPQFEK (SEQ ID NO:28)

Fig. 26

>RSV_F_E222Y_V469Y

MELLILKANAITTILTAVTFCFASGQNITEEFYQSTCSAVSKGYLSALRTGWYTSVITIELSNIKENKCNGTDAKVK
LIKQELDKYKNAVTELQLLMQSTPATNNRARRELPRFMNYTLNNAKKTNVTLSKKRKRRFLGFLLGVGSAIASGVAV
SKVLHLEGEVNKIKSALLSTNKAVVSLSNGVSVLTSKVLDLKNYIDKQLLPIVNKQSCSISNIETVIYFQQKNNRLL
EITREFSVNAGVTTPVSTYMLTNSELLSLINDMPITNDQKKLMSNNVQIVRQQSYSIMSIIKEEVLAYVVQLPLYGV
IDTPCWKLHTSPLCTTNTKEGSNICLTRTDRGWYCDNAGSVSFFPQAETCKVQSNRVFCDTMNSLTLPSEVNLCNVD
IFNPKYDCKIMTSKTDVSSSVITSLGAIVSCYGKTKCTASNKNRGIIKTFSNGCDYVSNKGVDTVSVGNTLYYVNKQ
EGKSLYYKGEPIINFYDPLVFPSDEFDASISQVNEKINQSLAFIRKSDELLSAIGGYIPEAPRDGQAYVRKDGEWVL
LSTFLGGLVPRGSHHHHHHSAWSHPQFEK (SEQ ID NO:29)

Fig. 27

>RSV_F_K226Y_V469Y

MELLILKANAITTILTAVTFCFASGQNITEEFYQSTCSAVSKGYLSALRTGWYTSVITIELSNIKENKCNGTDAKVK
LIKQELDKYKNAVTELQLLMQSTPATNNRARRELPRFMNYTLNNAKKTNVTLSKKRKRRFLGFLLGVGSAIASGVAV
SKVLHLEGEVNKIKSALLSTNKAVVSLSNGVSVLTSKVLDLKNYIDKQLLPIVNKQSCSISNIETVIEFQQYNNRLL
EITREFSVNAGVTTPVSTYMLTNSELLSLINDMPITNDQKKLMSNNVQIVRQQSYSIMSIIKEEVLAYVVQLPLYGV
IDTPCWKLHTSPLCTTNTKEGSNICLTRTDRGWYCDNAGSVSFFPQAETCKVQSNRVFCDTMNSLTLPSEVNLCNVD
IFNPKYDCKIMTSKTDVSSSVITSLGAIVSCYGKTKCTASNKNRGIIKTFSNGCDYVSNKGVDTVSVGNTLYYVNKQ
EGKSLYYKGEPIINFYDPLVFPSDEFDASISQVNEKINQSLAFIRKSDELLSAIGGYIPEAPRDGQAYVRKDGEWVL
LSTFLGGLVPRGSHHHHHHSAWSHPQFEK  (SEQ ID NO:30)

Fig. 28

>DS-Cav1_E222Y_V469Y

MELLILKANAITTILTAVTFCFASGQNITEEFYQSTCSAVSKGYLSALRTGWYTSVITIELSNIKENKCNGTDAKVK
LIKQELDKYKNAVTELQLLMQSTPATNNRARRELPRFMNYTLNNAKKTNVTLSKKRKRRFLGFLLGVGSAIASGVAV
CKVLHLEGEVNKIKSALLSTNKAVVSLSNGVSVLTFKVLDLKNYIDKQLLPILNKQSCSISNIETVIyFQQKNNRLL
EITREFSVNAGVTTPVSTYMLTNSELLSLINDMPITNDQKKLMSNNVQIVRQQSYSIMCIIKEEVLAYVVQLPLYGV
IDTPCWKLHTSPLCTTNTKEGSNICLTRTDRGWYCDNAGSVSFFPQAETCKVQSNRVFCDTMNSLTLPSEVNLCNVD
IFNPKYDCKIMTSKTDVSSSVITSLGAIVSCYGKTKCTASNKNRGIIKTFSNGCDYVSNKGVDTVSVGNTLYYVNKQ
EGKSLYyKGEPIINFYDPLVFPSDEFDASISQVNEKINQSLAFIRKSDELLSAIGGYIPEAPRDGQAYVRKDGEWVL
LSTFLGGLVPRGSHHHHHHSAWSHPQFEK (SEQ ID NO:31)

Fig. 29

>DS-Cav1_K226Y_V469Y

MELLILKANAITTILTAVTFCFASGQNITEEFYQSTCSAVSKGYLSALRTGWYTSVITIELSNIKENKCNGTDAKVK
LIKQELDKYKNAVTELQLLMQSTPATNNRARRELPRFMNYTLNNAKKTNVTLSKKRKRRFLGFLLGVGSAIASGVAV
CKVLHLEGEVNKIKSALLSTNKAVVSLSNGVSVLTFKVLDLKNYIDKQLLPILNKQSCSISNIETVIEFQQYNNRLL
EITREFSVNAGVTTPVSTYMLTNSELLSLINDMPITNDQKKLMSNNVQIVRQQSYSIMCIIKEEVLAYVVQLPLYGV
IDTPCWKLHTSPLCTTNTKEGSNICLTRTDRGWYCDNAGSVSFFPQAETCKVQSNRVFCDTMNSLTLPSEVNLCNVD
IFNPKYDCKIMTSKTDVSSSVITSLGAIVSCYGKTKCTASNKNRGIIKTFSNGCDYVSNKGVDTVSVGNTLYYVNKQ
EGKSLYYKGEPIINFYDPLVFPSDEFDASISQVNEKINQSLAFIRKSDELLSAIGGYIPEAPRDGQAYVRKDGEWVL
LSTFLGGLVPRGSHHHHHHSAWSHPQFEK (SEQ ID NO:32)

Fig. 30

>RSV_F_WT subtype A soluble

A

V185Y/K427Y

Inter-protomer

B

198Y/E222Y

Intra-protomer

```
RSF_F_WT_Subtype_A    ATGGAGTTGCTAATCCTCAAAGCAAATGCAATTACCACAATCCTCACTGCAGTCACATTT 60
RSF_F_WT_Subtype_B    ATGGAGTTGCTGATCCACAGGTCAAGTGCAATCTTCCTAACTCTTGCTATTAATGCATTG 60
                      ***********.****:**.. ***.******.:.*..**..**..**..::.:.****

RSF_F_WT_Subtype_A    TGTTTTGCTTCTGGTCAAAACATCACTGAAGAATTTTATCAATCAACATGCAGTGCAGTT 120
RSF_F_WT_Subtype_B    TACCTCACCTCAAGTCAGAACATAACTGAGGAGTTTTACCAATCGACATGTAGTGCAGTT 120
                      *. . *..*.**:.****.*****.*****.**.*****.*****.*****.********

RSF_F_WT_Subtype_A    AGCAAAGGCTATCTTAGTGCTCTGAGAACTGGTTGGTATACCAGTGTTATAACTATAGAA 180
RSF_F_WT_Subtype_B    AGCAGAGGTTATTTTAGTGCTTTAAGAACAGGTTGGTATACCAGTGTCATAACAATAGAA 180
                      ****.***.***.********.*.*****.*****************.*****:******

RSF_F_WT_Subtype_A    TTAAGTAATATCAAGAAAAATAAGTGTAATGGAACAGATGCTAAGGTAAAATTGATAAAA 240
RSF_F_WT_Subtype_B    TTAAGTAATATAACAGAAACCAAATGCAATGGAACTGACACTAAAGTAAAACTTATAAAA 240
                      ***********.*...***..**.**.********:**..****.******.*.******

RSF_F_WT_Subtype_A    CAAGAATTAGATAAATATAAAAATGCTGTAACAGAATTGCAGTTGCTCATGCAAAGCACA 300
RSF_F_WT_Subtype_B    CAAGAATTAGATAAGTATAAGAATGCAGTAACAGAATTACAGCTACTTATGCAAAACACG 300
                      **************.*****.*****.***********.***.*.**.*******.***.

RSF_F_WT_Subtype_A    CCAGCAACAAACAATCGAGCCAGAAGAGAACTACCAAGGTTTATGAATTATACACTCAAC 360
RSF_F_WT_Subtype_B    CCAGCTGCCAACAACCGGGCCAGAAGAGAAGCACCACAGCACATGAACTACACAATCAAT 360
                      *****:..*.*****.**.***********. ****..*.:.*****.**.***.****

RSF_F_WT_Subtype_A    AATGCCAAAAAACCAATGTAACATTAAGCAAGAAAAGGAAAAGAAGATTTCTTGGTTTT 420
RSF_F_WT_Subtype_B    ACCACTAAAAAACCTAAATGTATCAATAAGCAAGAAGAGGAAACGAAGATTTCTGGGCTTC 420
                      *.. .* *****.,. ******:**:***********.********.**********.**.**

RSF_F_WT_Subtype_A    TTGTTAGGTGTTGGATCTGCAATCGCCAGTGGCGTTGCTGTATCTAAGGTCCTGCACCTA 480
RSF_F_WT_Subtype_B    TTGTTAGGTGTAGGATCTGCAATAGCAAGTGGTATAGCTGTATCCAAAGTTCTACACCTT 480
                      ***********:***********.**.*****..*:********..**.**.**.*****:

RSF_F_WT_Subtype_A    GAAGGGGAAGTGAACAAGATCAAAAGTGCTCTACTATCCACAAACAAGGCTGTAGTCAGC 540
RSF_F_WT_Subtype_B    GAAGGAGAAGTGAACAAAATCAAAAATGCTTTGTTGTCTACAAACAAAGCTGTAGTCAGT 540
                      *****.***********.*******.****.*..*.**.*******.***********

RSF_F_WT_Subtype_A    TTATCAAATGGAGTCAGTGTCTTAACCAGCAAAGTGTTAGACCTCAAAAACTATATAGAT 600
RSF_F_WT_Subtype_B    CTATCAAATGGGGTCAGTGTTTTAACCAGCAAAGTGTTAGATCTCAAGAATTACATAAAT 600
                      .********.*.******.************************.*****.**.**.***.**

RSF_F_WT_Subtype_A    AAACAATTGTTACCTATTGTGAACAAGCAAAGCTGCAGCATATCAAATATAGAAACTGTG 660
RSF_F_WT_Subtype_B    AACCAATTATTACCCATAGTAAATCAACAGAGCTGTCGCATCTTCAACATTGAAACAGTT 660
                      **.*****.*****.**:**.**.*.**.*****.*****..***.**.**:*****:**

RSF_F_WT_Subtype_A    ATAGAGTTCCAACAAAAGAACAACAGACTACTAGAGATTACCAGGGAATTTAGTGTTAAT 720
RSF_F_WT_Subtype_B    ATAGAATTCCAACGAAGAATAGCAGATTGTTGGAAATCACCAGAGAATTTAGTGTCAAT 720
                      *****.*******.****.****.*******.*.****.**...*****.*********.***

RSF_F_WT_Subtype_A    GCAGGTGTAACTACACCTGTAAGCACTTACATGTTAACTAATAGTGAATTATTGTCATTA 760
RSF_F_WT_Subtype_B    GCAGGTGTAACAACACCTTTAAGCACTTACATGTTAACAAACAGTGAGTTACTATCATTG 780
                      ***********:******.*******************:**.*****.***.*.*****.

RSF_F_WT_Subtype_A    ATCAATGATATGCCTATAACAAATGATCAGAAAAAGTTAATGTCCAACAATGTTCAAATA 840
RSF_F_WT_Subtype_B    ATCAATGATATGCCTATAACAAATGATCAGAAAAAATTAATGTCAAGCAATGTTCAGATA 840
                      ***********************************.*******.*..********.***

RSF_F_WT_Subtype_A    GTTAGACAGCAAAGTTACTCTATCATGTCCATAATAAAAGAGGAAGTCTTAGCATATGTA 900
RSF_F_WT_Subtype_B    GTAAGGCAACAAAGTTATTCTATCATGTCTATAATAAAGGAAGAAGTCCTTGCATATGTT 900
                      **:**.**.********.***********.*******.**.*******.**.********:
```

Fig. 36A

```
RSF_F_WT_Subtype_A    GTACAATTACCACTATATGGTGTTATAGATACACCCTGTTGGAAACTACACACATCCCCT 960
RSF_F_WT_Subtype_B    GTACAGCTACCTATCTATGGTGTAATAGATACACCTTGCTGGAAATTACACACATCACCT 960
                      *****  ****  * *********  *************  ******  **********  ***

RSF_F_WT_Subtype_A    CTATGTACAACCAACACAAAGAAGGGTCCAACATCTGTTTAACAAGAACTGACAGAGGA 1020
RSF_F_WT_Subtype_B    CTATGCACCACCAACATCAAAGAAGGATCAAATATTTGTTTAACAAGGACTGATAGAGGA 1020
                      ***** **  ******   ******** *** ** ** ** ************  *****  ******

RSF_F_WT_Subtype_A    TGGTACTGTGACAATGCAGGATCAGTATCTTTCTTCCCACAAGCTGAAACATGTAAAGTT 1080
RSF_F_WT_Subtype_B    TGGTATTGTGATAATGCAGGATCAGTATCCTTCTTCCCACAGGCTGACACTTGCAAAGTA 1080
                      ***** ***** ***************** *********** ***** ** ** *****

RSF_F_WT_Subtype_A    CAATCAAATCGAGTATTTTGTGACACAATGAACAGTTTAACATTACCAAGTGAAGTAAAT 1140
RSF_F_WT_Subtype_B    CAGTCCAATCGAGTATTTTGTGACACTATGAACAGTTTGACATTACCAAGTGAAGTCAGC 1140
                      ** ** ******************** ********** ****************** *

RSF_F_WT_Subtype_A    CTCTGCAATGTTGACATATTCAACCCCAAATATGATTGTAAAATTATGACTTCAAAAACA 1200
RSF_F_WT_Subtype_B    CTTTGTAACACTGACATATTCAATTCCAAGTATGACTGCAAAATTATGACATCAAAAACA 1200
                      ** ** **    *********** ****  ***** **  *********** ********

RSF_F_WT_Subtype_A    GATGTAAGCAGCTCCGTTATCACATCTCTAGGAGCCATTGTGTCATGCTATGGCAAAACT 1260
RSF_F_WT_Subtype_B    GACATAAGCAGCTCAGTAATTACTTCTCTTGGAGCTATAGTGTCATGTTATGGTAAAACT 1260
                      **  ********** ** ** ** ***** ***** ** ******* ***** ******

RSF_F_WT_Subtype_A    AAATGTACAGCATCCAATAAAAATCGTGGAATCATAAAGACATTTTCTAACGGGTGCGAT 1320
RSF_F_WT_Subtype_B    AAATGCACTGCATCCAATAAAAATCGTGGGATTATAAAGACATTTTCTAATGGTTGTGAC 1320
                      ***** ** ******************** ** ***************** ** ** **

RSF_F_WT_Subtype_A    TATGTATCAAATAAAGGGGTGGACACTGTGTCTGTAGGTAACACATTATATTATGTAAAT 1380
RSF_F_WT_Subtype_B    TATGTGTCAAACAAAGGAGTAGATACTGTGTCAGTGGGCAACACTTTATACTATGTAAAC 1380
                      ***** ***** *****  ** ** ********  ** ** ***** ***** *******

RSF_F_WT_Subtype_A    AAGCAAGAAGGTAAAAGTCTCTATGTAAAAGGTGAACCAATAATAAATTTCTATGACCCA 1440
RSF_F_WT_Subtype_B    AAGCTGGAAGGCAAGAACCTTTATGTAAAAGGGGAACCTATAATAAATTACTATGATCCT 1440
                      ****  ***** **  **  * ***********  ***** ******** ****** **

RSF_F_WT_Subtype_A    TTAGTATTCCCCTCTGATGAATTTGATGCATCAATATCTCAAGTCAACGAGAAGATTAAC 1500
RSF_F_WT_Subtype_B    CTAGTGTTTCCTTCTGATGAGTTTGATGCATCAATATCTCAAGTCAATGAAAAAATCAAT 1500
                      ****  ** **  ** ******* ***********************  ** ** ** **

RSF_F_WT_Subtype_A    CAGAGCCTAGCATTTATTCGTAAATCCGATGAATTATTACATAATGTAAATGCCGGTAAA 1560
RSF_F_WT_Subtype_B    CAAAGTTTAGCTTTTATTCGTAAATCTGATGAATTACTACATAATGTAAATACTGGCAAA 1560
                      ** **  **** ************** ********  *************** * ** ***

RSF_F_WT_Subtype_A    TCCACCACAAATATCATGATAACTACTATAATTATAGTGATTATAGTAATATTGTTATCA 1620
RSF_F_WT_Subtype_B    TCTACTACAAATATTATGATAACTACAATTATTATAGTAATCATTGTAGTATTGTTATCA 1620
                      ** ** ********  **********  *   ****** **  **    *****     *  **********

RSF_F_WT_Subtype_A    TTAATTGCTGTTGGACTGCTCTTATACTGTAAGGCCAGAAGCACACCAGTCACACTAAGC 1680
RSF_F_WT_Subtype_B    TTAATAGCTATTGGTTTACTGTTGTATTGCAAAGCCAAAAACACACCAGTTACACTAAGC 1680
                      ***** *** ****   * ***   **  ** ***** **  ** ********* *********

RSF_F_WT_Subtype_A    AAAGATCAACTGAGTGGTATAAATAATATTGCATTTAGTAACTAA 1725
RSF_F_WT_Subtype_B    AAAGACCAACTAAGTGGAATCAATAATATTGCATTCAGCAAATAG 1725
                      ***** *****  ***** ** ************* ** ** **
```

Sequence identity: 81.57%

Fig. 36 B

>RSV_F_subytpeA_nt_human_codon_opti

```
ATGGAGCTGCTCATCCTGAAGGCCAACGCCATCACCACCATCCTCACCGCCGTGACCTTCTGCTTCGCCAGCGGCCAGAATATCACCGAGGAGT
CTTACCAGAGCACCTGCAGCGCCGTGAGCAAGGGCTACCTGAGCGCCCTGAGAACCGGCTGGTACACCAGCGTGATCACCATCGAGCTGAGCAA
CATCAAGAAGAACAAGTGCAACGGCACCGACGCCAAGGTGAAGCTCATCAAGCAGGAGCTGGACAAGTACAAGAACGCCGTGACCGAGCTGCAG
CTGCTCATGCAGAGCACCCAGGCCACCAACAACAGGGCCAGAAGGGAGCTGCCCCGGTTCATGAACTACACCCTGAACAACGCCAAGAAAACCA
ACGTGACCCTGAGCAAGAAGCGGAAGCGGAGATTCCTGGGCTTCCTGCTGGGCGTGGGCAGCGCCATCGCCAGCGGAGTGGCCGTGTCCAAGGT
GCTGCACCTGGAGGGCGAGGTGAACAAGATCAAGAGCGCCCTGCTGAGCACCAACAAGGCCGTGGTGAGCCTGAGCAACGGCGTGAGCGTGCTC
ACCAGCAAGGTGCTGGATCTGAAGAACTACATCGACAAGCAGCTGCTGCCCATCGTGAACAAGCAGAGCTGCAGCATCAGCAACATCGAGACCG
TGATCGAGTTCCAGCAGAAGAACAACCGGCTGCTGGAGATCACCAGGGAGTTCAGCGTGAACGCCGGCGTGACCACCCCCGTGAGCACCTACAT
GCTCACCAACAGCGAGCTGCTGAGCCTCATCAACGACATGCCCATCACCAACGACCAGAAGAAGCTCATGAGCAACAACGTGCAGATCGTGCGG
CAGCAGAGCTACTCCATCATGAGCATCATCAAGGAGGAGGTGCTGGCCTACGTGGTGCAGCTGCCCCTGTACGGCGTGATCGATACCCCTTGCT
GGAAGCTGCACACCAGCCCCCTGTGCACCACCAACACCAAGGAGGGCAGCAACATCTGCCTCACCAGGACCGATAGAGGCTGGTACTGCGACAA
CGCCGGCAGCGTGTCATTCTTTCCACAGGCCGAGACCTGCAAGGTGCAGAGCAACCGGGTGTTCTGCGACACCATGAACAGCCTCACCCTGCCC
AGCGAAGTGAACCTGTGCAACGTGGACATCTTCAACCCCAAGTACGACTGCAAGATCATGACCAGCAAGACCGACGTGAGCAGCAGCGTGATTA
CCAGCCTGGGCGCCATCGTGAGCTGCTACGGCAAGACCAAGTGCACCGCCAGCAACAAGAACCGGGGGATCATCAAGACCTTCAGCAACGGCTG
CGACTACGTGAGCAACAAGGGCGTGGATACCGTGAGCGTGGGCAACACCCTGTACTACGTGAATAAGCAGGAGGGCAAGAGCCTGTACGTGAAG
GGCGAGCCCATCATCAACTTCTACGACCCCCTGGTGTTCCCTAGCGACGAGTTCGATGCCAGCATCAGCCAGGTGAACGAGAAGATCAACCAGA
GCCTGGCCTTCATCAGGAAGAGCGACGAGCTGCTGCACAATGTGAATGCCGGCAAGAGCACCACCAATATCATGATCACCACAATCATCATCGT
GATCATTGTGATCCTGCTGTCCCTCATCGCCGTGGGCCTGCTGCTGTACTGCAAGGCCAGAAGCACCCCTGTGACCCTGTCCAAGGATCAGCTG
AGCGGCATCAACAATATCGCCTTCTCCAACTGA
```

Fig. 37

>RSV_F_subytpeA_nt_CHO_codon_opti

```
ATGGAACTGCTGATCCTGAAGGCCAACGCCATCACCACCATCCTGACCGCCGTGACCTTCTGCTTCGCCTCCGGCCAGAACATCACCGAGGAAT
CTTACCAGTCTACCTGCTCCGCCGTGTCCAAGGGCTACCTGTCTGCTCTGAGAACCGGCTGGTACACCTCCGTGATCACCATCGAGCTGTCCAA
CATCAAGAAAAACAAGTGCAACGGCACCGACGCCAAAGTGAAGCTGATCAAGCAGGAACTGGACAAGTACAAGAATGCCGTGACCGAACTGCAG
CTGCTGATGCAGTCTACCCAGGCCACCAACAACCGGGCCAGACGCGAGCTGCCCAGATTCATGAACTACACCCTGAACAACGCCAAAAAGACCA
ACGTGACCCTGTCCAAGAAGCGGAAGCGGCGGTTCCTGGGCTTTCTGCTGGGAGTGGGCTCCGCTATCGCTTCTGGCGTGGCCGTGTCTAAGGT
GCTGCACCTGGAAGGCGAAGTGAACAAGATCAAGTCCGCCCTGCTGAGCACCAACAAGGCCGTGGTGTCCCTGAGCAACGGCGTGTCCGTGCTG
ACCTCCAAGGTGCTGGATCTGAAGAACTACATCGACAAGCAGCTGCTGCCCATCGTGAACAAGCAGTCCTGCTCCATCTCCAACATCGAGACAG
TGATCGAGTTCCAGCAGAAGAACAACCGGCTGCTGGAAATCACCCGCGAGTTCTCCGTGAATGCCGGCGTGACCACCCCCGTGTCCACCTACAT
GCTGACCAACTCCGAGCTGCTGTCTCTGATCAACGACATGCCCATCACCAACGACCAGAAAAAGCTGATGTCCAACAACGTGCAGATCGTGCGG
CAGCAGTCCTACAGCATCATGTCCATCATCAAAGAAGAGGTGCTGGCCTACGTGGTGCAGCTGCCTCTGTACGGCGTGATCGACACCCCCTGCT
GGAAGCTGCACACCAGCCCTCTGTGCACCACCAACACCAAAGAGGGCAGCAACATCTGCCTGACCCGGACCGACAGAGGCTGGTACTGTGACAA
CGCTGGCTCCGTCTCATTCTTTCCACAAGCCGAGACATGCAAGGTGCAGTCCAACCGGGTGTTCTGCGACACCATGAACTCCCTGACCCTGCCC
TCTGAAGTGAACCTGTGCAACGTGGACATCTTCAACCCTAAGTACGACTGCAAGATCATGACCAGCAAGACCGACGTGTCCAGCTCTGTGATCA
CCTCCCTGGGCGCCATCGTGTCCTGCTACGGCAAGACCAAGTGCACGCCTCCAACAAGAACCGGGGCATCATCAAGACCTTCTCCAACGGCTG
CGACTATGTGTCTAACAAGGGCGTGGACACCGTGTCTGTGGGCAACACCCTGTACTACGTGAACAAACAGGAAGGCAAGTCCCTGTACGTGAAG
GGCGAGCCTATCATCAACTTCTACGACCCCCTGGTGTTCCCCAGCGACGAGTTCGACGCCTCCATCAGCCAAGTGAACGAGAAGATCAACCAGT
CCCTGGCCTTCATCCGGAAGTCCGATGAGCTGCTGCACAATGTGAACGCCGGCAAGTCCACCACCAATATCATGATCACCACAATCATCATCGT
GATTATCGTGATCCTGCTGAGCCTGATCGCCGTGGGCCTGCTGCTGTACTGCAAGGCCAGATCCACCCCTGTGACACTGAGCAAGGACCAGCTG
TCCGGCATCAACAATATCGCCTTCAGCAACTGA
```

Fig. 38

>RSV_F_subytpeA_nt_SF9_codon_opti
ATGGAACTGCTGATCCTGAAGGCTAACGCTATCACCACCATCCTGACCGCTGTGACCTTCTGCTTCGCTTCCGGCCAGAACATCACCGAGGAAT
TCTACCAGTCTACCTGCTCCGCTGTGTCCAAGGGTTACCTGTCCGCTCTGCGTACCGGCTGGTACACCTCCGTGATCACCATCGAGCTGTCCAA
CATCAAGAAGAACAAGTGCAACGGCACCGACGCTAAAGTGAAGCTGATCAAGCAAGAGCTGGACAAGTACAAGAACGCTGTCACCGAACTGCAG
CTGCTGATGCAGTCCACCCCAGGCTACCAACAACCGTGCTCGTCGCGAGCTGCCCCGTTTCATGAACTACACCCTGAACAACGCCAAGAAGACCA
ACGTCACCCTGTCCAAGAAGCGCAAGCGCCGTTTCCTGGGGTTTCCTGCTGGGTGTCGGTTCCGCTATCGCCTCCGGTGTCGCTGTCTCTAAGGT
GCTGCACCTCGAGGGCGAAGTGAACAAGATCAAGTCCGCCCTGCTGTCCACCAACAAGGCTGTGGTGTCCCTGTCTAACGGTGTCTCCGTGCTG
ACCTCCAAGGTCCTGGACCTGAAGAACTACATCGACAAGCAACTGCTGCCCATCGTGAACAAGCAGTCCTGCTCCATCTCCAACATCGAGACTG
TGATCGAGTTCCAGCAAAAGAACAACCGCCTGCTCGAGATCACCCGCGAGTTCTCCGTGAACGCTGGTGTCACCACCCCCGTGTCCACCTACAT
GCTGACCAACTCCGAGCTGCTGTCCCTGATCAACGACATGCCCATCACCAACGACCAAAAGAAGCTGATGTCCAACAACGTGCAGATCGTGCGT
CAGCAGTCCTACTCTATCATGAGCATCATCAAGGAAGAGGTGCTGGCTTACGTGGTGCAGCTGCCCCTGTACGGTGTCATCGACACCCCCTGCT
GGAAGCTGCACACCTCCCACTGTGCACCACCAACACCAAGGAAGGTTCCAACATCTGCCTGACCCGTACCGACCGTGGCTGGTACTGCGACAA
CGCTGGTTCCGTTTCATTCTTCCCAACAAGCCGAGACTTGCAAGGTGCAGTCCAACCGTGTGTTCTGCGACACCATGAACTCCCTGACCCTGCCC
TCCGAAGTCAACCTGTGCAACGTGGACATCTTCAACCCTAAGTACGACTGCAAGATCATGACCAGCAAGACCGACGTGTCCTCCTCTGTCATCA
CCTCCCTGGGTGCTATCGTGTCCTGCTACGGCAAGACCAAGTGCACCGCTTCCAACAAGAACCGCGGTATCATCAAGACCTTCTCCAACGGTTG
CGACTACGTCAGCAACAAGGGCGTGGACACCGTGTCCGTGGGCAACACCCTGTACTACGTCAACAAGCAAGAGGGCAAGTCCCTGTACGTGAAG
GGCGAGCCCATCATCAACTTCTACGACCCCCTGGTGTTCCCATCCGACGAGTTCGACGCTTCCATCTCCCAAGTGAACGAGAAGATCAACCAGT
CCCTGGCTTTCATCCGCAAGTCCGACGAGCTGCTCCACAACGTCAACGCTGGCAAGTCCACCACTAACATCATGATCACTACCATCATCATCGT
GATCATCGTCATCCTGCTGAGCCTGATCGCTGTGGGCCTGCTGCTGTACTGCAAGGCTCGTTCCACCCCTGTGACTCTGTCCAAGGACCAGCTG
TCCGGTATCAACAACATCGCCTTCAGCAACTAA

Fig. 39

>RSV_F_subytpeA_nt_Mouse_codon_opti
ATGGAACTGCTGATCCTGAAGGCCAACGCCATCACCACCATCCTGACCGCCGTGACCTTCTGCTTCGCCAGCGGCCAGAACATCACCGAGGAAT
TCTACCAGAGCACCCTGTAGCGCCGTGTCCAAGGGCTACCTGAGCGCCCTGAGAACCGGCTGGTACACCAGCGTGATCACCATCGAGCTGAGCAA
CATCAAGAAAAACAAGTGCAACGGCACCGACGCCAAAGTGAAGCTGATCAAGCAGGAACTGGACAAGTACAAGAACGCCGTGACAGAACTGCAG
CTGCTGATGCAGAGCACCCAGGCCACCAACAACAGAGCCAGACGCGAGCTGCCCAGATTCATGAACTACACCCTGAACAACGCCAAAAAGACCA
ACGTGACCCTGAGCAAGAAGAGGAAGCGCAGATTCCTGGGCTTCCTGCTGGGCGTGGGCAGCGCTATTGCTTCTGGCGTGGCCGTGTCTAAGGT
GCTGCACCTGGAAGGCGAAGTGAACAAGATCAAGTCCGCCCTGCTGAGCACCAACAAGGCCGTGGTGTCTCTGAGCAACGGCGTGTCCGTGCTG
ACCAGCAAGGTGCTGGATCTGAAGAACTACATCGACAAAAGCTGCTGCCCATCGTGAACAAGCAGAGCTGCAGCATCAGCAACATCGAGACAG
TGATCGAGTTCCAGCAGAAGAACAACCGGCTGCTGGAAATCACCCGCGAGTTCAGCGTGAACGCTGGCGTGACCACCCCCGTGTCCACCTACAT
GCTGACCAACAGCGAGCTGCTGAGCCTGATCAACGACATGCCCATCACCAACGACCAGAAAAAGCTGATGAGCAACAACGTGCAGATCGTGCGG
CAGCAGAGCTACTCCATCATGAGCATCATCAAGGAAGAGGTGCTGGCCTACGTGGTGCAGCTGCCTCTGTACGGCGTGATCGACACCCCCTGCT
GGAAGCTGCACACCAGCCCTCTGTGCACCACCAACACCAAGAGGGCTCCAACATCTGCCTGACCAGAACCGACAGAGGCTGGTACTGCGACAA
CGCCGGCTCCGTCATTCTTTCCACAAGCCGAGACATGCAAGGTGCAGAGCAACAGAGTGTTCTGCGACACCATGAACAGCCTGACCCTGCCC
TCTGAAGTGAACCTGTGCAACGTGGACATCTTCAACCCTAAGTACGACTGCAAGATCATGACCTCCAAGACCGACGTGTCCAGCTCCGTGATCA
CAAGCCTGGGCGCCATCGTGTCCTGCTACGGCAAGACCAAGTGCACCGCCAGCAACAAGAACAGGGGAATCATCAAGACCTTCAGCAACGGCTG
CGACTACGTGTCCAACAAGGGGGTGGACACCGTGTCTGTGGGCAACACCCTGTACTACGTGAACAAACAGGAAGGCAAGAGCCTGTACGTGAAG
GGCGAGCCCATCATCAACTTCTACGACCCCCTGGTGTTCCCAGCGACGAGTTCGACGCCAGCATCTCCCAAGTGAACGAGAAGATCAACCAGA
GCCTGGCCTTCATCAGAAAGTCCGATGAGCTGCTGCACAATGTGAACGCCGGCAAGAGCACCACAAACATCATGATCACCACTATCATCATCGT
GATCATTGTGATCCTGCTGTCCCTGATCGCCGTGGGCCTGCTGCTGTACTGCAAGGCCAGATCCACCCCTGTGACCCTGTCCAAGGACCAGCTG
AGCGGCATCAACAATATCGCCTTCTCCAACTGA

Fig. 40

>RSV-F_subtypeB_HUMAN_codonOPTI

ATGGAACTGCTGATCCACAGAAGCAGCGCCATCTTCCTGACCCTGGCCATCAACGCCCTGTACCTGACCAGCAGCCAGAACATCACCGAGGAAT
TCTACCAGAGCACCTGTAGCGCCGTGTCCCGGGGCTACTTTAGCGCCCTGAGAACCGGCTGGTACACCAGCGTGATCACCATCGAGCTGAGCAA
TATCACCGAGACAAAGTGCAACGGCACCGACACCAAAGTGAAGCTGATCAAGCAGGAACTGGACAAGTACAAGAACGCCGTGACCGAACTGCAG
CTGCTGATGCAGAATACCCCTGCCGCCAACAACCGGGCCAGAAGAGAAGCCCCCCAGCACATGAACTACACCATCAACACCACCAAGAACCTGA
ACGTGTCCATCAGCAAGAAGCGGAAGCGGCGGTTCCTGGGCTTTCTGCTGGGAGTGGGAAGCGCCATTGCCAGCGGAATCGCCGTGTCTAAGGT
GCTGCACCTGGAAGGCGAAGTGAACAAGATCAAGAATGCCCTGCTGAGCACCAACAAGGCCGTGGTGTCCCTGAGCAACGGCGTGTCCGTGCTG
ACCTCCAAGGTGCTGGATCTGAAGAACTACATCAACAACCAGCTGCTGCCCATCGTGAACCAGCAGAGCTGCCGGATCTTCAACATCGAGACAG
TGATCGAGTTCCAGCAGAAGAACAGCAGGCTGCTGGAAATCACCCGCGAGTTCAGCGTGAACGCTGGCGTGACCACACCCCTGAGCACCTACAT
GCTGACCAACAGCGAGCTGCTGTCCCTGATCAATGACATGCCCATCACCAACGACCAGAAAAAGCTGATGAGCAGCAACGTGCAGATCGTGCGG
CAGCAGTCCTACAGCATCATGAGCATCATCAAAGAAGAGGTGCTGGCCTACGTGGTGCAGCTGCCTATCTACGGCGTGATCGACACCCCCTGCT
GGAAGCTGCACACCAGCCCTCTGTGCACCACCAACATCAAAGAGGGCAGCAACATCTGCCTGACCAGAACCGACCGGGGCTGGTACTGCGATAA
TGCCGGCTCCGTCTCATTCTTTCCACAAGCCGATACCTGCAAGGTGCAGAGCAACCGGGTGTTCTGCGACACCATGAACAGCCTGACACTGCCC
AGCGAAGTGTCCCTGTGTAACACCGACATCTTCAACTCTAAGTACGACTGCAAGATCATGACCAGCAAGACCGACATCAGCTCCTCCGTGATCA
CAAGCCTGGGCGCCATCGTGTCCTGCTACGGCAAGACCAAGTGCACCGCCAGCAACAAGAACCGGGGAATCATCAAGACCTTCAGCAACGGCTG
CGACTACGTGTCCAACAAGGGGGTGGACACCGTGTCTGTGGGCAACACCCTGTACTACGTGAACAAGCTGGAAGGGAAGAATCTGTACGTGAAG
GGCGAGCCCATCATCAACTACTACGACCCCCTGGTGTTCCCCAGCGACGAGTTCGATGCCAGCATCAGCCAAGTGAACGAGAAGATCAACCAGA
GCCTGGCCTTCATCAGAAAGTCCGATGAGCTGCTGCACAATGTGAACACCGGCAAGTCCACCACAAATATCATGATCACCACCATCATTATCGT
GATCATCGTGGTGCTGCTGAGCCTGATCGCCATCGGCCTGCTGCTGTACTGCAAGGCCAAGAACACCCCCGTGACCCTGTCCAAGGATCAGCTG
AGCGGCATCAACAATATCGCCTTCTCCAAGTGA

Fig. 41

>RSV-F_subtypeB_CHO_codonOPTI

ATGGAACTGCTGATCCACCGGTCCTCCGCCATCTTCCTGACCCTGGCCATCAACGCCCTGTACCTGACCTCCTCCCAGAACATCACCGAGGAAT
TCTACCAGTCTACCTGCTCCGCCGTGTCCCGGGGCTACTTCTCTGCTCTGAGAACCGGCTGGTACACCTCCGTGATCACCATCGAGCTGTCCAA
TATCACCGAGACAAAGTGCAACGGCACCGACACCAAAGTGAAGCTGATCAAGCAGGAACTGGACAAGTACAAGAACGCCGTGACCGAACTGCAG
CTGCTGATGCAGAATACCCCTGCCGCCAACAACCGGGCCAGAAGAGAAGCCCCCCAGCACATGAACTACACCATCAACACCACCAAGAACCTGA
ACGTGTCCATCTCCAAGAAGCGGAAGCGGCGGTTCCTGGGCTTTCTGCTGGGAGTGGGCTCCGCTATCGCCTCCGGAATCGCCGTGTCTAAGGT
GCTGCACCTGGAAGGCGAAGTGAACAAGATCAAGAATGCCCTGCTGTCCACCAACAAGGCCGTGGTGTCCCTGTCCAACGGCGTGTCCGTGCTG
ACCTCCAAGGTGCTGGATCTGAAGAACTACATCAACAACCAGCTGCTGCCCATCGTGAACCAGCAGTCCTGCCGGATCTTCAACATCGAGACAG
TGATCGAGTTCCAGCAGAAGAACTCCCGGCTGCTGGAAATCACCCGCGAGTTCTCTGTGAATGCCGGCGTGACCACCCCCCTGTCCACCTACAT
GCTGACCAACTCCGAGCTGCTGTCCCTGATCAACGACATGCCCATCACCAACGACCAGAAAAAGCTGATGTCCTCCAACGTGCAGATCGTGCGG
CAGCAGAGCTACTCCATCATGTCCATTATCAAAGAAGAGGTGCTGGCCTACGTGGTGCAGCTGCCTATCTACGGCGTGATCGACACCCCCTGCT
GGAAGCTGCACACCAGCCCTCTGTGCACCACCAACATCAAAGAGGGCTCCAACATCTGCCTGACCAGAACCGACCGGGGCTGGTACTGTGACAA
CGCTGGCTCCGTCTCATTCTTTCCACAAGCCGATACCTGCAAGGTGCAGTCCAACCGGGTGTTCTGCGACACCATGAATTCTCTGACCCTGCCC
TCCGAAGTGTCTCTGTGTAACACCGACATCTTCAACTCTAAGTACGACTGCAAGATCATGACCAGCAAGACCGATATCTCCAGCTCTGTGATCA
CCTCCCTGGGCGCCATCGTGTCCTGCTACGGCAAGACCAAGTGCACCGCCTCCAACAAGAACCGGGGCATCATCAAGACCTTCTCCAACGGCTG
CGACTACGTGTCCAACAAGGGGGTGGACACCGTGTCTGTGGGCAACACCCTGTACTACGTGAACAAGCTGGAAGGGAAGAATCTGTACGTGAAG
GGCGAGCCCATCATCAACTACTACGACCCCCTGGTGTTCCCCAGCGACGAGTTCGACGCCTCCATCAGCCAAGTGAACGAGAAGATCAACCAGT
CCCTGGCCTTCATCCGGAAGTCCGATGAGCTGCTGCACAATGTGAACACCGGCAAGTCCACCACAAATATCATGATCACCACCATCATTATCGT
GATCATCGTGGTGCTGCTGAGCCTGATCGCCATCGGCCTGCTGCTGTACTGCAAGGCCAAGAACACCCCCGTGACCCTGAGCAAGGACCAGCTG
TCCGGCATCAACAATATCGCCTTCAGCAAGTGA

Fig. 42

>RSV-F_subtypeB_SF9_codonOPTI

```
ATGGAACTGCTGATCCACCGTTCCTCCGCTATCTTCCTGACCCTGGCTATCAACGCTCTGTACCTGACCTCCTCCCAGAACATCACCGAGGAAT
TCTACCAGTCTACCTGCTCCGCTGTGTCCCGTGGTTACTTCTCCGCTCTGCGTACCGGCTGGTACACCTCCGTGATCACCATCGAGCTGTCCAA
CATCACTGAGACTAAGTGCAACGGCACCGACACCAAAGTGAAGCTGATCAAGCAAGAGCTGGACAAGTACAAGAACGCTGTGACCGAACTGCAG
CTGCTGATGCAGAACACCCCCGCTGCTAACAACCGTGCTCGTCGCGAAGCTCCCCAGCACATGAACTACACCATCAACACCACCAAGAACCTGA
ACGTGTCCATCTCCAAGAAGCGCAAGCGCCGTTTCCTGGGTTTCCTGCTGGGTGTCGGTTCCGCTATCGCTTCCGGTATCGCTGTCTCCAAGGT
GCTGCACCTCGAGGGCGAAGTGAACAAGATCAAGAACGCCCTGCTGTCCACCAACAAGGCTGTGGTGTCCCTGTCCAACGGTGTCTCCGTGCTG
ACCTCCAAGGTCCTCGACCTGAAGAACTACATCAACAACCAGCTGCTGCCCATCGTGAACCAGCAGTCCTGCCGTATCTTCAACATCGAGACTG
TGATCGAGTTCCAGCAGAAGAACTCCCGTCTGCTCGAGATCACCCGCGAGTTCTCCGTGAACGCTGGTGTCACCACCCCCTGTCCACCTACAT
GCTGACCAACTCCGAGCTGCTGTCCCTGATCAACGACATGCCCATCACCAACGACCAAAAGAAGCTGATGTCCTCCAACGTGCAGATCGTGCGT
CAGCAGTCTTACTCCATCATGTCCATCATCAAGGAAGAGGTGCTGGCTTACGTGGTGCAGCTGCCTATCTACGGTGTCATCGACACCCCCTGCT
GGAAGCTGCACACCTCCCCACTGTGCACCACCAACATCAAGGAAGGTTCCAACATCTGCCTGACCCGTACCGACCGTGGCTGGTACTGCGACAA
CGCTGGTTCCGTTTCATTCTTCCCACAAGCCGACACTTGCAAGGTGCAGTCCAACCGTGTGTTCTGCGACACCATGAACTCCCTGACTCTGCCC
TCCGAGGTGCCCTCTGCAACACCGACATCTTCAACTCTAAGTACGACTGCAAGATCATGACCTCTAAGACTGACATCTCCTCCAGCGTCATCA
CCTCCCTGGGTGCTATCGTGTCCTGCTACGGCAAGACCAAGTGCACCGCTTCAACAAGAACCGCGGTATCATCAAGACCTTCTCCAACGGTTG
CGACTACGTGTCCAACAAGGGCGTGGACACCGTGTCCGTGGGCAACACCCTGTACTACGTGAACAAGCTCGAGGGCAAGAACCTCTACGTGAAG
GGCGAGCCTATCATCAACTACTACGACCCCCTGGTGTTCCCATCCGACGAGTTCGACGCTTCCATCTCCCAAGTGAACGAGAAGATCAACCAGT
CCCTGGCTTTCATCCGCAAGTCCGACGAGCTGCTCCACAACGTGAACACCGGCAAGTCCACTACTAACATCATGATCACCACTATCATCATCGT
GATCATCGTCGTGCTGCTGAGCCTGATCGCTATCGGCCTGCTGCTGTACTGCAAGGCTAAGAACACTCCCGTGACCCTGTCTAAGGACCAGCTG
TCCGGTATCAACAACATCGCCTTCAGCAAGTAA
```

Fig. 43

>RSV-F_subtypeB_mouse_codonOPTI

```
ATGGAACTGCTGATCCACAGAAGCAGCGCCATCTTCCTGACCCTGGCCATCAACGCCCTGTACCTGACCAGCAGCCAGAACATCACCGAGGAAT
TCTACCAGAGCACCTGTAGCGCCGTGTCCAGAGGCTACTTCAGCGCCCTGAGAACCGGCTGGTACACCAGCGTGATCACCATCGAGCTGAGCAA
CATCACAGAGACAAAGTGCAACGGCACCGACACCAAAGTGAAGCTGATCAAGCAGGAACTGGACAAGTACAAGAACGCCGTGACCGAACTGCAG
CTGCTGATGCAGAACACCCCTGCCGCCAACAACAGAGCCAGAAGAGAAGCCCCCAGCACATGAACTACACCATCAACACCACCAAGAACCTGA
ACGTGTCCATCAGCAAGAAGAGGAAGAGAAGATTCCTGGGCTTCCTGCTGGGGTGGCAGCGCTATCGCCTTCTGGAATCGCCGTGTCTAAGGT
GCTGCACCTGGAAGGCGAAGTGAACAAGATCAAGAACGCCCTCTGAGCACCAACAAGGCCGTGGTCCCTGAGCAACGGCGTGTCCGTGCTG
ACCTCCAAGGTGCTGGATCTGAAGAACTACATCAACAACCAGCTGCTGCCCATCGTGAACCAGCAGAGCTGCAGAATCTTCAACATCGAGACAG
TGATCGAGTTCCAGCAGAAGAACAGCAGGCTGCTGGAAATCACCCGCGAGTTCAGCGTGAACGCTGGCGTGACCACACCCCTGAGCACCTACAT
GCTGACCAACAGCGAGCTGCTGTCTCTGATCAACGACATGCCCATCACCAACGACCAGAAAAAGCTGATGAGCAGCAACGTGCAGATCGTGCGG
CAGCAGTCCTACAGCATCATGAGCATCATCAAAGAAGAGGTGCTGGCCTACGTGGTGCAGCTGCCTATCTACGGCGTGATCGACACCCCCTGCT
GGAAGCTGCACACCAGCCCTCTGTGCACCACCAACATCAAGAGGGCAGCAACATCTGCCTGACCAGAACCGACAGAGGCTGGTACTGCGACAA
CGCCGGCTCCGTCTCATTCTTTCCACAAGCCGACACATGCAAGGTGCAGAGCAACAGAGTGTTCTGCGACACCATGAACAGCCTGACACTGCCC
AGCGAAGTGTCCCTGTGTAACACCGACATCTTCAACTCTAAGTACGACTGCAAGATCATGACCAGCAAGACCGACATCAGCTCCTCCGTGATCA
CAAGCCTGGGCGCCATCGTGTCCTGCTACGGCAAGACCAAGTGCACCGCCAGCAACAAGAACAGGGGAATCATCAAGACCTTCAGCAACGGCTG
CGACTACGTGTCCAACAAGGGGGTGGACACCGTGTCTGTGGGCAACACCCTGTACTACGTGAACAAGCTGGAAGGGAAGAATCTGTACGTGAAG
GGCGAGCCCATCATCAACTACTACGACCCCTGGTGTTCCCCAGCGACGAGTTCGACGCCAGCATCAGCCAAGTGAACGAGAAGATCAACCAGA
GCCTGGCCTTCATCAGAAAGTCCGATGAGCTGCTGCACAATGTGAACACCGGCAAGTCCACAACAAACATCATGATCACCACCATCATTATCGT
GATCATCGTGGTGCTGCTGAGCCTGATCGCCATCGGCCTGCTGCTGTACTGCAAGGCCAAGAACACACCCGTGACCCTGTCCAAGGACCAGCTG
AGCGGCATCAACAATATCGCCTTCTCCAAGTGA
```

Fig. 44

>RSV_F_subtypeA_DS-CAV1_nt_Human_codon_opti

ATGGAACTGCTGATCCTGAAGGCCAACGCCATCACCACCATCCTGACCGCCGTGACCTTCTGCTTCGCCAGCGGCCAGAACATCACCGAGGAAT
TCTACCAGAGCACCTGCAGCGCCGTGAGCAAGGGCTACCTGAGCGCCCTGCGGACCGGCTGGTACACCAGCGTGATCACCATCGAGCTGTCCAA
CATCAAAGAAAACAAGTGCAACGGCACCGACGCCAAAGTGAAGCTGATCAAGCAGGAACTGGACAAGTACAAGAACGCCGTGACCGAGCTGCAG
CTGCTGATGCAGAGCACCCCCGCCACCAACAACAGAGCCAGAAGAGAGCTGCCCCGGTTCATGAACTACACCCTGAACAACGCCAAGAAAAACCA
ACGTGACCCTGAGCAAGAAGAGAAAGAGAAGATTCCTGGGCTTCCTGCTGGGCGTGGGCAGCGCCATTGCCAGCGGCGTGGCCGTGTGCAAAGT
GCTGCACCTGGAAGGCGAAGTGAACAAGATCAAGTCCGCCCTGCTGTCCACCAACAAGGCCGTGGTGTCCCTGAGCAACGGCGTGAGCGTGCTG
ACCTTCAAGGTGCTGGATCTGAAGAACTACATCGACAAGCAGCTGCTGCCCATCCTGAACAAGCAGAGCTGCAGCATCAGCAACATCGAGACAG
TGATCGAGTTCCAGCAGAAGAACAACCGGCTGCTGGAAATCACCCGGGAGTTCAGCGTGAACGCCGGAGTGACCACCCCCGTGTCCACCTACAT
GCTGACCAACAGCGAGCTGCTGTCCCTGATCAATGACATGCCCATCACCAACGACCAGAAAAAGCTGATGAGCAACAACGTGCAGATCGTGCGG
CAGCAGAGCTACTCCATCATGTGCATCATCAAAGAAGAGGTGCTGGCCTACGTGGTGCAGCTGCCCCTGTACGGCGTGATCGACACCCCCTGCT
GGAAGCTGCACACCAGCCCCCTGTGCACAACCAACACCAAAGAGGGCAGCAACATCTGCCTGACCCGGACCGACCGGGGCTGGTACTGCGACAA
CGCCGGCAGCGTGTCCTTCTTTCCACAGGCCGAGACATGCAAGGTGCAGAGCAACCGGGTGTTCTGCGACACCATGAACAGCCTGACCCTGCCC
TCCGAAGTGAACCTGTGCAACGTGGACATCTTCAACCCCAAGTACGACTGCAAGATCATGACCTCCAAGACCGACGTGTCCAGCTCCGTGATCA
CCTCCCTGGGCGCCATCGTGTCCTGCTACGGCAAGACCAAGTGCACCGCCAGCAACAAGAACAGAGGCATCATCAAGACCTTCAGCAACGGCTG
CGACTACGTGTCCAATAAGGGCGTGGACACCGTGTCCGTGGGCAACACACTGTACTACGTGAATAAGCAGGAAGGCAAGAGCCTGTACGTGAAG
GGCGAGCCCATCATCAACTTCTACGACCCCCTGGTGTTCCCCAGCGACGAGTTCGACGCCAGCATCAGCCAGGTGAACGAGAAGATCAACCAGA
GCCTGGCCTTCATCAGAAAGAGCGACGAACTGCTGTCCGCCATCGGCGGCTACATCCCCGAGGCCCCCAGAGATGGCCAGGCCTACGTGCGGAA
GGACGGCGAGTGGGTGCTGCTGTCTACATTTCTGGGCGGCCTGGTGCCTAGAGGCTCTCACCACCACCATCACCACAGCGCCTGGTCCCACCCC
CAGTTCGAGAAGTGA

Fig. 45

>RSV_F_subtypeA_DS_nt_Human_codon_opti

ATGGAACTGCTGATCCTGAAGGCCAACGCCATCACCACCATCCTGACCGCCGTGACCTTCTGCTTCGCCAGCGGCCAGAACATCACCGAGGAAT
TCTACCAGAGCACCTGCAGCGCCGTGAGCAAGGGCTACCTGAGCGCCCTGCGGACCGGCTGGTACACCAGCGTGATCACCATCGAGCTGTCCAA
CATCAAAGAAAACAAGTGCAACGGCACCGACGCCAAAGTGAAGCTGATCAAGCAGGAACTGGACAAGTACAAGAACGCCGTGACCGAGCTGCAG
CTGCTGATGCAGAGCACCCCCGCCACCAACAACAGAGCCAGAAGAGAGCTGCCCCGGTTCATGAACTACACCCTGAACAACGCCAAGAAAACCA
ACGTGACCCTGAGCAAGAAGAGAAAGAGAAGATTCCTGGGCTTCCTGCTGGGCGTGGGCAGCGCCATTGCCAGCGGCGTGGCCGTGTGCAAAGT
GCTGCACCTGGAAGGCGAAGTGAACAAGATCAAGTCCGCCCTGCTGTCCACCAACAAGGCCGTGGTGTCCCTGAGCAACGGCGTGAGCGTGCTG
ACCAGCAAGGTGCTGGATCTGAAGAACTACATCGACAAGCAGCTGCTGCCCATCGTGAACAAGCAGAGCTGCAGCATCAGCAACATCGAGACAG
TGATCGAGTTCCAGCAGAAGAACAACCGGCTGCTGGAAATCACCCGGGAGTTCAGCGTGAACGCCGGAGTGACCACCCCCGTGTCCACCTACAT
GCTGACCAACAGCGAGCTGCTGTCCCTGATCAATGACATGCCCATCACCAACGACCAGAAAAAGCTGATGAGCAACAACGTGCAGATCGTGCGG
CAGCAGAGCTACTCCATCATGTGCATCATCAAAGAAGAGGTGCTGGCCTACGTGGTGCAGCTGCCCCTGTACGGCGTGATCGACACCCCCTGCT
GGAAGCTGCACACCAGCCCCCTGTGCACAACCAACACCAAAGAGGGCAGCAACATCTGCCTGACCCGGACCGACCGGGGCTGGTACTGCGACAA
CGCCGGCAGCGTGTCCTTCTTTCCACAGGCCGAGACATGCAAGGTGCAGAGCAACCGGGTGTTCTGCGACACCATGAACAGCCTGACCCTGCCC
TCCGAAGTGAACCTGTGCAACGTGGACATCTTCAACCCCAAGTACGACTGCAAGATCATGACCTCCAAGACCGACGTGTCCAGCTCCGTGATCA
CCTCCCTGGGCGCCATCGTGTCCTGCTACGGCAAGACCAAGTGCACCGCCAGCAACAAGAACAGAGGCATCATCAAGACCTTCAGCAACGGCTG
CGACTACGTGTCCAATAAGGGCGTGGACACCGTGTCCGTGGGCAACACACTGTACTACGTGAATAAGCAGGAAGGCAAGAGCCTGTACGTGAAG
GGCGAGCCCATCATCAACTTCTACGACCCCCTGGTGTTCCCCAGCGACGAGTTCGACGCCAGCATCAGCCAGGTGAACGAGAAGATCAACCAGA
GCCTGGCCTTCATCAGAAAGAGCGACGAACTGCTGTCCGCCATCGGCGGCTACATCCCCGAGGCCCCCAGAGATGGCCAGGCCTACGTGCGGAA
GGACGGCGAGTGGGTGCTGCTGTCTACATTTCTGGGCGGCCTGGTGCCTAGAGGCTCTCACCACCACCATCACCACAGCGCCTGGTCCCACCCC
CAGTTCGAGAAGTGA

Fig. 46

>RSV_F_subtypeA_CAV1_nt_Human_codon_opti
ATGGAACTGCTGATCCTGAAGGCCAACGCCATCACCACCATCCTGACCGCCGTGACCTTCTGCTTCGCCAGCGGCCAGAACATCACCGAGGAAT
TCTACCAGAGCACCTGCAGCGCCGTGAGCAAGGGCTACCTGAGCGCCCTGCGGACCGGCTGGTACACCAGCGTGATCACCATCGAGCTGTCCAA
CATCAAAGAAAACAAGTGCAACGGCACCGACGCCAAAGTGAAGCTGATCAAGCAGGAACTGGACAAGTACAAGAACGCCGTGACCGAGCTGCAG
CTGCTGATGCAGAGCACCCCCGCCACCAACAACAGAGCCAGAAGAGAGCTGCCCCGGTTCATGAACTACACCCTGAACAACGCCAAGAAAACCA
ACGTGACCCTGAGCAAGAAGAGAAAGAGAAGATTCCTGGGCTTCCTGCTGGGCGTGGGCAGCGCCATTGCCAGCGGCGTGGCCGTGTCCAAAGT
GCTGCACCTGGAAGGCGAAGTGAACAAGATCAAGTCCGCCCTGCTGTCCACCAACAAGGCCGTGGTGTCCCTGAGCAACGGCGTGAGCGTGCTG
ACCTTCAAGGTGCTGGATCTGAAGAACTACATCGACAAGCAGCTGCTGCCCATCCTGAACAAGCAGAGCTGCAGCATCAGCAACATCGAGACAG
TGATCGAGTTCCAGCAGAAGAACAACCGGCTGCTGGAAATCACCCGGGAGTTCAGCGTGAACGCCGGAGTGACCACCCCCGTGTCCACCTACAT
GCTGACCAACAGCGAGCTGCTGTCCCTGATCAATGACATGCCCATCACCAACGACCAGAAAAAGCTGATGAGCAACAACGTGCAGATCGTGCGG
CAGCAGAGCTACTCCATCATGAGCATCATCAAAGAAGAGGTGCTGGCCTACGTGGTGCAGCTGCCCCTGTACGGCGTGATCGACACCCCCTGCT
GGAAGCTGCACACCAGCCCCCTGTGCACAACCAACACCAAAGAGGGCAGCAACATCTGCCTGACCCGGACCGACCGGGGCTGGTACTGCGACAA
CGCCGGCAGCGTGTCCTTCTTTCCACAGGCCGAGACATGCAAGGTGCAGAGCAACCGGGTGTTCTGCGACACCATGAACAGCCTGACCCTGCCC
TCCGAAGTGAACCTGTGCAACGTGGACATCTTCAACCCCAAGTACGACTGCAAGATCATGACCTCCAAGACCGACGTGTCCAGCTCCGTGATCA
CCTCCCTGGGCGCCATCGTGTCCTGCTACGGCAAGACCAAGTGCACCGCCAGCAACAAGAACAGAGGCATCATCAAGACCTTCAGCAACGGCTG
CGACTACGTGTCCAATAAGGGCGTGGACACCGTGTCCGTGGGCAACACACTGTACTACGTGAATAAGCAGGAAGGCAAGAGCCTGTACGTGAAG
GGCGAGCCCATCATCAACTTCTACGACCCCCTGGTGTTCCCCAGCGACGAGTTCGACGCCAGCATCAGCCAGGTGAACGAGAAGATCAACCAGA
GCCTGGCCTTCATCAGAAGAGCGACGAACTGCTGTCCGCCATCGGCGGCTACATCCCCGAGGCCCCAGAGATGGCCAGGCCTACGTGCGGAA
GGACGGCGAGTGGGTGCTGCTGTCTACATTTCTGGGCGGCCTGGTGCCTAGAGGCTCTCACCACCACCATCACCACAGCGCCTGGTCCCACCCC
CAGTTCGAGAAGTGA

Fig. 47

CONFORMATIONALLY STABILIZED RSV PRE-FUSION F PROTEINS

CROSS-REFERENCE TO RELATED APPLICATIONS

This application claims the benefit of U.S. Provisional Patent Application No. 61/858,533, filed Jul. 25, 2013, the contents of which are hereby incorporated by reference.

STATEMENT REGARDING FEDERALLY SPONSORED RESEARCH

This invention was made with government support under grant number 1R43AI112124-01A1 awarded by the National Institute of Allergy and Infectious Diseases (NIAID). The government has certain rights in the invention.

SEQUENCE LISTING

The instant application contains a Sequence Listing which has been submitted electronically in ASCII format and is hereby incorporated by reference in its entirety. Said ASCII copy, created on Jul. 24, 2014, is named Avatar_007_US2_Sequence_Listing.txt and is 195,572 bytes in size.

COPYRIGHT & INCORPORATION-BY-REFERENCE

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

For the purposes of only those jurisdictions that permit incorporation by reference, the text of all documents cited herein is hereby incorporated by reference in its entirety.

BACKGROUND OF THE INVENTION

Each year, respiratory syncytial virus (RSV) infects 4-5 million children in the US, and is the leading cause of infant hospitalizations (~150,000 hospitalizations). Globally, it accounts for 6.7% of deaths in infants less than 1 year old, second only to malaria. In addition, it poses a serious threat to other high-risk groups, including elderly and immuno-compromised subjects, where it results in approximately an additional 180,000 hospitalizations and 12,000 deaths in the US. There are no current frontline treatments for RSV, and the only currently approved prophylactic treatment for RSV is passive administration of the licensed monoclonal antibody Synagis (palivizumab), which recognizes the RSV fusion (F) protein, and reduces incidence of severe disease by only ~50%. The high cost of prophylaxis with Synagis limits its use only to premature infants and infants less than 24 months old with congenital heart disease. For a review see Costello et al., "Targeting RSV with Vaccines and Small Molecule Drugs, Infectious Disorders," Drug Targets, 2012, vol. 12, no. 2. The development of a more effective and, ideally, more cost-effective RSV vaccine would be of enormous value. Clinical evidence that RSV F protein-specific antibodies can protect against disease has prompted a concerted effort to identify additional and better monoclonal antibodies, and to develop a protective vaccine to address this significant unmet medical need.

BRIEF SUMMARY OF THE INVENTION

Some aspects of the present invention are summarized below. Additional aspects are described in the Detailed Description of the Invention, the Examples, the Figures and the claims herein.

The RSV F protein is known to induce potent neutralizing antibodies that correlate with protection against RSV. Recently it has been shown that the pre-fusion conformation of the RSV F protein trimer (which may be referred to as "pre-fusion F" or "pre-F" herein) is the primary determinant of neutralizing activity in human sera. Also, the most potent neutralizing antibodies (nAbs) isolated to date specifically bind only to the pre-fusion conformation. However, soluble pre-F is highly unstable and readily transitions to the post-fusion conformation—limiting its usefulness as a vaccine immunogen. An RSV F protein stabilized in its pre-fusion (pre-F) conformation could be very valuable—providing a candidate RSV vaccine immunogen. Similarly, such a stabilized RSV pre-F protein could also be useful for the generation of antibodies, such as diagnostic and therapeutic antibodies. The crystal structure of the RSV F protein (bound to a potent nAb—D25) in its pre-fusion conformation was recently described. See McLellan et al., 2013, Science, 340, p. 1113-1117, the contents of which are hereby incorporated by reference in their entirety. Building on this work, the present inventors have performed extensive analysis of the structure of the RSV F protein and have developed a variety of novel design strategies and novel constructs to stabilize or "lock" the RSV F protein in its pre-F conformation.

In some embodiments the present invention provides RSV F polypeptides, proteins, and protein complexes, such as those that can be or are stabilized or "locked" in a pre-fusion conformation, for example using targeted cross-links, such as targeted di-tyrosine cross-links. The present invention also provides methods for making and using such RSV F polypeptides, proteins, and protein complexes.

In some embodiments, the present invention provides specific locations within the amino acid sequence of the RSV F protein at which, or between which, cross-links can be made in order to stabilize the RSV F protein in its pre-F conformation. In some embodiments, the cross-links are targeted di-tyrosine cross-links. Where di-tyrosine cross-links are used, the present invention provides specific amino acid residues (or pairs of amino acid residues) that either comprise a pre-existing tyrosine residue or can be or are mutated to a tyrosine residue such that di-tyrosine cross-links can be made.

In some embodiments, the present invention provides an isolated RSV F polypeptide, protein or protein complex comprising at least one di-tyrosine cross-link, wherein at least one tyrosine of the at least one di-tyrosine cross-links originates from a point mutation to tyrosine.

In some embodiments, the invention provides an isolated RSV F polypeptide, protein or protein complex having at least about 75% sequence identity to SEQ ID NO:1, 2, 3, 4, 5, 6, 7, 8, 9 or 10, or amino acid residues 1-513 thereof (comprising the RSV F ectodomain), wherein the protein polypeptide comprises at least one tyrosine residue that originates from a point mutation to tyrosine. In some such embodiments the RSV F polypeptides, proteins or protein complexes contain at least one di-tyrosine cross-link wherein at least one tyrosine residue of the at least one cross-link originates from a point mutation to tyrosine.

In some embodiments, the invention provides an isolated RSV F polypeptide having the amino acid sequence of SEQ ID NO:11, 12, 13, 14, 15, 16, 17, 18, 19, 20, 21, 22, 23, 24, 25, 26, 27, 28, 29, 30, 31 or 32, or amino acid residues 1-513 thereof (comprising the RSV F ectodomain). In some embodiments, the invention provides an isolated RSV F protein or polypeptide having at least about 75% sequence identity to SEQ ID NO:11, 12, 13, 14, 15, 16, 17, 18, 19, 20, 21, 22, 23, 24, 25, 26, 27, 28, 29, 30, 31 or 32, or amino acid residues 1-513 thereof (comprising the RSV F ectodomain). In some such embodiments the RSV F polypeptides, proteins or protein complexes contain at least one di-tyrosine cross-link wherein at least one tyrosine residue of the at least one cross-link originates from a point mutation to tyrosine.

In some embodiments, where di-tyrosine cross-links are present, the di-tyrosine cross-link comprises two pre-existing tyrosine residues. In some embodiments, the di-tyrosine cross-link comprises a pre-existing tyrosine cross-linked to a tyrosine originating from a point mutation to tyrosine. In some embodiments, the di-tyrosine cross-link comprises two tyrosines originating from point mutations to tyrosine. In some embodiments, the di-tyrosine cross-link comprises an intra-protomer bond, an inter-protomer bond, an intra-molecular bond, an inter-molecular bond, or any combination thereof. In some embodiments, the di-tyrosine cross-link comprises a bond within or between a RSV F protein F1 polypeptide and a RSV F protein F2 polypeptide. In some embodiments, the point mutation to tyrosine is located at one or more amino acid positions selected from the group consisting of amino acid positions: 77, 88, 97, 147, 150, 155, 159, 183, 185, 187, 220, 222, 223, 226, 255, 427 or 469 of SEQ ID NO: 1 or SEQ ID NO: 4, or any amino acid position that corresponds to one of such amino acid positions in another RSV F amino acid sequence or ectodomain thereof.

In some embodiments, the invention provides an isolated RSV F polypeptide, protein or protein complex having at least about 75% sequence identity to SEQ ID NO:1, 2, 3, 4, 5, 6, 7, 8, 9 or 10, wherein the polypeptide comprises at least one di-tyrosine cross-link, wherein one or both tyrosines of the cross-link originates from a point mutation to tyrosine, and wherein the cross-links are located between one or more paired tyrosine amino acid residues located at amino acid positions: 147 and 286; 198 and 220; 198 and 222; 198 and 223; 198 and 226; 33 and 469; 77 and 222; 88 and 255; 97 and 159; 183 and 427; 185 and 427; or 187 and 427. In some embodiments, the RSV F polypeptide, protein, or protein complex comprises more than one di-tyrosine cross-link. In some embodiments, the RSV F polypeptide, protein, or protein complex comprises two, three, four, five or more di-tyrosine cross-links. In some embodiments, the RSV F polypeptide, protein, or protein complex comprises di-tyrosine cross-links at paired tyrosine amino acid residues located at amino acid positions 77 and 222, and 33 and 469.

In some embodiments, the RSV F polypeptides, proteins, or protein complexes of the invention further comprise one or more additional cross-links, such as disulfide bonds. In such embodiments, at least one cysteine of the one or more disulfide bonds originates from a point mutation to cysteine. In some embodiments, the RSV F polypeptides, proteins, or protein complexes further comprise cavity-filling hydrophobic amino acid substitutions. In some embodiments, the RSV F polypeptides, proteins, or protein complexes further comprises a trimerization domain. In such embodiments, the trimerization domain is a foldon domain.

In some embodiments, the RSV F polypeptides, proteins, or protein complexes of the invention are capable of eliciting a protective immune response in a subject and/or eliciting production of RSV-specific neutralizing antibodies in a subject. In some embodiments, the the RSV F polypeptides, proteins, or protein complexes of the invention comprise at least one antigenic site capable of binding a neutralizing antibody, for example, the antigenic site 0.

In some embodiments, the invention provides compositions (such as pharmaceutical compositions and/or vaccine compositions) comprising one or more RSV F polypeptides, proteins, or protein complexes of the invention. In some embodiments, such compositions comprise an adjuvant, a carrier, an immunostimulatory agent, or any combination thereof. In some embodiments, the composition is, or forms part of, a vaccine for respiratory syncytial virus. In some embodiments, the invention provides a method of vaccinating a subject against RSV, the method comprising administering an effective amount of a composition comprising one or more of the RSV F polypeptides, proteins, or protein complexes of the invention to a subject. In some embodiments, the subject is a human of less than 24 months in age or a human of greater than 50 years in age. In some embodiments, the administering comprises a single immunization. In some embodiments, a method of the invention further comprises administering to a subject a pharmaceutical composition comprising one or more RSV F polypeptides, proteins, or protein complexes of the invention so as to treat or prevent an RSV infection in the subject. In some embodiments, the invention provides a medicament for inducing an immune response in a subject, comprising one or more the RSV F polypeptides, proteins, or protein complexes of the invention. In some embodiments, the medicament is a vaccine.

In some embodiments, the invention provides a method of making a RSV vaccine immunogen, comprising (a) identifying or obtaining a RSV F polypeptide, protein or protein complex in a pre-fusion conformation; (b) selecting one or more regions in the RSV F polypeptide, protein or protein complex where the introduction of one or more cross-links (such as di-tyrosine cross-links) could stabilize the pre-fusion conformation; (c) introducing into the RSV F protein one or more cross-links (such as di-tyrosine cross-links) at one or more of the regions selected in step (b) to form an engineered RSV F polypeptide, protein or protein complex; and (d) determining if the engineered RSV F polypeptide, protein or protein complex has one or more properties selected from the group consisting of: (i) enhanced ability bind to a neutralizing antibody, (ii) enhanced ability bind to a broadly neutralizing, (iii) enhanced ability bind to and activate B cell receptors, (iv) enhanced ability to elicit an antibody response in an animal, (v) enhanced ability to elicit a protective antibody response in an animal, (vi) enhanced ability to elicit production of neutralizing antibodies in an animal, (vii) enhanced ability to elicit production of broadly neutralizing antibodies in an animal, (viii) enhanced ability to elicit a protective immune response in an animal, and (ix) enhanced ability to bind to and elicit production of antibodies that recognize quaternary neutralizing epitopes in an animal, wherein if the engineered RSV F polypeptide, protein or protein complex has one or more properties i. to ix., the engineered RSV F polypeptide, protein or protein complex is a RSV vaccine immunogen candidate. In some such embodiments, step (d) comprises performing one or more assays to assess the ability of the engineered RSV F protein to bind to a neutralizing antibody, bind to a broadly neutralizing antibody, bind to and activate a B cell receptors elicit an antibody response in an animal, elicit a protective antibody response in an animal, elicit production of neutralizing antibodies in an animal, elicit production of broadly neutralizing antibodies in an animal, elicit a protective immune response in an animal, and/or elicit production of antibodies that recognize quaternary neutralizing epitopes in an animal. In some embodiments, where di-tyrosine cross-links are used, at least one tyrosine of the one or more di-tyrosine cross-links introduced in step (c) originates from a point mutation to tyrosine. In some embodiments, the method further comprises, prior to step (c), introducing into the RSV F protein one or more point mutations to tyrosine at one or more of the regions selected in step (b). These and other embodiments of the present invention are described throughout the present patent specification.

BRIEF DESCRIPTION OF THE DRAWINGS

FIGS. 1A-1B. Amino acid sequences of (A) soluble RSV F protein from RSV subtype A (WT) (SEQ ID NO:1), and (B) full-length RSV F protein from RSV subtype A (SEQ ID NO:2) (Accession No. AHJ60043.1). Amino acid residues 1-513 of both sequences are the core sequences of the RSV F protein that are common to both the soluble and membrane-bound (full-length) forms. The C-terminal sequences from amino acid residue 514 onwards in SEQ ID NO. 1 comprise a foldon trimerization domain followed by a thrombin cleavage site, 6× His-tag (SEQ ID NO: 46), and a strep tag. The C-terminal sequences from amino acid residue 514 onwards in SEQ ID NO. 2 comprise the endogenous RSV F protein sequence containing the transmembrane region and cytoplasmic tail.

FIGS. 2A-2B. Amino acid sequences of (A) soluble RSV F protein from RSV subtype B (SEQ ID NO:3), and (B) full-length RSV F protein from RSV subtype B (SEQ ID NO:4) (Accession No. AHL84194). Amino acid residues 1-513 of both sequences are the core sequences of the RSV F protein that are common to both the soluble and membrane-bound (full-length) forms. The C-terminal sequences from amino acid residue 514 onwards in SEQ ID NO. 3 comprise a foldon trimerization domain followed by a thrombin cleavage site, 6× His-tag (SEQ ID NO: 46), and a strep tag. The C-terminal sequences from amino acid residue 514 onwards in SEQ ID NO. 4 comprise the endogenous RSV F protein sequence containing the transmembrane region and cytoplasmic tail.

FIGS. 3A-3B. Amino acid sequences of (A) soluble DS-Cav1 modified RSV F protein (SEQ ID NO:5), and (B) full-length DS-Cav1 modified RSV F protein (SEQ ID NO:6) (McLellan et al. (2013) Science 342:592-598). Amino acid residues 1-513 of both sequences are the core sequences of the RSV F protein that are common to both the soluble and membrane-bound (full-length) forms. The C-terminal sequences from amino acid residue 514 onwards in SEQ ID NO. 5 comprise a foldon trimerization domain followed by a thrombin cleavage site, 6× His-tag (SEQ ID NO: 46), and a strep tag. The C-terminal sequences from amino acid residue 514 onwards in SEQ ID NO. 6 comprise the endogenous RSV F protein sequence containing the transmembrane region and cytoplasmic tail.

FIGS. 4A-4B. Amino acid sequences of (A) soluble Cav1 modified RSV F protein (SEQ ID NO:7), and (B) full-length Cav1 modified RSV F protein sequence (SEQ ID NO:8) (McLellan et al. (2013) Science 342:592-598).). Amino acid residues 1-513 of both sequences are the core sequences of the RSV F protein that are common to both the soluble and membrane-bound (full-length) forms. The C-terminal sequences from amino acid residue 514 onwards in SEQ ID NO. 7 comprise a foldon trimerization domain followed by a thrombin cleavage site, 6× His-tag (SEQ ID NO: 46), and a strep tag. The C-terminal sequences from amino acid residue 514 onwards in SEQ ID NO. 8 comprise the endogenous RSV F protein sequence containing the transmembrane region and cytoplasmic tail.

FIGS. 5A-5B. Amino acid sequences of (A) soluble DS modified RSV F protein (SEQ ID NO:9), and (B) full-length DS modified RSV F protein sequence (SEQ ID NO:10) (McLellan et al. (2013) Science 342:592-598).). Amino acid residues 1-513 of both sequences are the core sequences of the RSV F protein that are common to both the soluble and membrane-bound (full-length) forms. The C-terminal sequences from amino acid residue 514 onwards in SEQ ID NO. 9 comprise a foldon trimerization domain followed by a thrombin cleavage site, 6× His-tag (SEQ ID NO: 46), and a strep tag. The C-terminal sequences from amino acid residue 514 onwards in SEQ ID NO. 10 comprise the endogenous RSV F protein sequence containing the transmembrane region and cytoplasmic tail.

FIG. 6. Sequence alignment of RSV F proteins from RSV subtype A (SEQ ID NO:1—identified as "RSV_F_WT" in the figure) and subtype B (SEQ ID NO:4). Amino acid residues shown in bold and underlined in the subtype A sequence indicate sites that can be targeted for di-tyrosine cross-linking either as single or double mutants. The equivalent sites in subtype B are also shown in boxes. The designated positions targeted for di-tyrosine cross-linking are 100% conserved between RSV subtypes A and B. Amino acid residues 1-513 of both sequences are the core sequences of the RSV F protein. The C-terminal sequences from amino acid residue 514 onwards in SEQ ID NO. 1 comprise a foldon trimerization domain followed by a thrombin cleavage site, 6× His-tag (SEQ ID NO: 46), and a strep tag. The C- terminal sequences from amino acid residue 514 onwards in SEQ ID NO. 4 comprise the endogenous RSV F protein sequence containing the transmembrane region and cytoplasmic tail.

FIG. 7. Sequence alignment of DS-Cav1 RSV F protein (SEQ ID NO:5), and RSV F proteins from RSV subtype A (SEQ ID NO:1) and subtype B (SEQ ID NO:4). The C-terminal sequences shown in italics in the DS-Cav1 and RSV subtype A sequences (residues 514 - 568) contain the exogenous Foldon trimerization domain followed by a thrombin cleavage site, 6× His-tag (SEQ ID NO: 46) and a strep tag. The C-terminal sequence shown in bold and underlined in the RSV subtype B sequence (residues 514 - 574) is the endogenous F protein sequence containing the transmembrane region and cytoplasmic tail.

FIG. 8. Amino acid sequence of a modified soluble RSV F protein (subtype A) comprising a to-tyrosine mutation at position 147 (A147Y) (SEQ ID NO:11). Amino acid residues 1-513 are the core sequences of the RSV F protein. The C-terminal sequences from amino acid residue 514 onwards comprise a foldon trimerization domain followed by a thrombin cleavage site, 6× His-tag (SEQ ID NO: 46), and a strep tag.

FIG. 9. Amino acid sequence of a modified soluble RSV F protein (subtype A) comprising a to-tyrosine mutation at position 220 (V220Y) (SEQ ID NO:12). Amino acid residues 1-513 are the core sequences of the RSV F protein. The C-terminal sequences from amino acid residue 514 onwards comprise a foldon trimerization domain followed by a thrombin cleavage site, 6× His-tag (SEQ ID NO: 46), and a strep tag.

FIG. 10. Amino acid sequence of a modified soluble RSV F protein (subtype A) comprising a to-tyrosine mutation at position 222 (E222Y) (SEQ ID NO:13). Amino acid residues 1-513 are the core sequences of the RSV F protein. The C-terminal sequences from amino acid residue 514 onwards comprise a foldon trimerization domain followed by a thrombin cleavage site, 6× His-tag (SEQ ID NO: 46), and a strep tag.

FIG. 11. Amino acid sequence of a modified soluble RSV F protein (subtype A) comprising a to-tyrosine mutation at position 223 (F223Y) (SEQ ID NO:14). Amino acid residues 1-513 are the core sequences of the RSV F protein. The C-terminal sequences from amino acid residue 514 onwards comprise a foldon trimerization domain followed by a thrombin cleavage site, 6× His-tag (SEQ ID NO: 46), and a strep tag.

FIG. 12. Amino acid sequence of a modified soluble RSV F protein (subtype A) comprising a to-tyrosine mutation at position 226 (K226Y) (SEQ ID NO:15). Amino acid residues 1-513 are the core sequences of the RSV F protein. The C-terminal sequences from amino acid residue 514 onwards comprise a foldon trimerization domain followed by a thrombin cleavage site, 6× His-tag (SEQ ID NO: 46), and a strep tag.

FIG. 13. Amino acid sequence of a modified soluble RSV F protein (subtype A) comprising a to-tyrosine mutation at position 469 (V469Y) (SEQ ID NO:16). Amino acid residues 1-513 are the core sequences of the RSV F protein. The C-terminal sequences from amino acid residue 514 onwards comprise a foldon trimerization domain followed by a thrombin cleavage site, 6× His-tag (SEQ ID NO: 46), and a strep tag.

FIG. 14. Amino acid sequence of a modified soluble RSV F protein (subtype A) comprising to-tyrosine mutations at positions 77 (K77Y) and 222 (E222Y) (SEQ ID NO:17). Amino acid residues 1-513 are the core sequences of the RSV F protein. The C-terminal sequences from amino acid residue 514 onwards comprise a foldon trimerization domain followed by a thrombin cleavage site, 6× His-tag (SEQ ID NO: 46), and a strep tag.

FIG. 15. Amino acid sequence of a modified soluble RSV F protein (subtype A) comprising to-tyrosine mutations at positions 88 (N88Y) and 255 (S255Y) (SEQ ID NO:18). Amino acid residues 1-513 are the core sequences of the RSV F protein. The C-terminal sequences from amino acid residue 514 onwards comprise a foldon trimerization domain followed by a thrombin cleavage site, 6× His-tag (SEQ ID NO: 46), and a strep tag.

FIG. 16. Amino acid sequence of a modified soluble RSV F protein (subtype A) comprising to-tyrosine mutations at positions 97 (M97Y) and 159 (H159Y) (SEQ ID NO:19). Amino acid residues 1-513 are the core sequences of the RSV F protein. The C-terminal sequences from amino acid residue 514 onwards comprise a foldon trimerization domain followed by a thrombin cleavage site, 6× His-tag (SEQ ID NO: 46), and a strep tag.

FIG. 17. Amino acid sequence of a modified soluble RSV F protein (subtype A) comprising to-tyrosine mutations at positions 185 (V185Y) and 427 (K427Y) (SEQ ID NO:20). Amino acid residues 1-513 are the core sequences of the RSV F protein. The C-terminal sequences from amino acid residue 514 onwards comprise a foldon trimerization domain followed by a thrombin cleavage site, 6× His-tag (SEQ ID NO: 46), and a strep tag.

FIG. 18. Amino acid sequence of a modified soluble RSV F protein (subtype A) comprising to-tyrosine mutations at positions 187 (V187Y) and 427 (K427Y) (SEQ ID NO:21). Amino acid residues 1-513 are the core sequences of the RSV F protein. The C-terminal sequences from amino acid residue 514 onwards comprise a foldon trimerization domain followed by a thrombin cleavage site, 6× His-tag (SEQ ID NO: 46), and a strep tag.

FIG. 19. Amino acid sequence of a modified soluble RSV F protein (subtype A) comprising to tyrosine mutations at positions 183 (N183Y) and 427 (K427Y) (SEQ ID NO:22). Amino acid residues 1-513 are the core sequences of the RSV F protein. The C-terminal sequences from amino acid residue 514 onwards comprise a foldon trimerization domain followed by a thrombin cleavage site, 6× His-tag (SEQ ID NO: 46), and a strep tag.

FIG. 20A-20C. Sequence alignment of soluble RSV F protein subtype A (SEQ ID NO:1) and examples of modified RSV F proteins derived therefrom (SEQ ID NOS:11-21) comprising single or double to-tyrosine mutations. Tyrosines in boxes are introduced into the WT subtype A sequence. Where two new tyrosines are introduced into the same sequence, they are typically intended to cross-link with each other. Where only a single tyrosine is introduced, that tyrosine is typically expected to cross-link with an endogenous or pre-existing tyrosine in that sequence which is shown in bold and underlined. Amino acid residues 1-513 of each sequence are the core sequences of the RSV F protein. The C-terminal sequences from amino acid residue 514 onwards comprise a foldon trimerization domain followed by a thrombin cleavage site, 6× His-tag (SEQ ID NO: 46), and a strep tag.

FIG. 21. Amino acid sequence of a modified soluble RSV F protein (DS-Cav1) comprising a to-tyrosine mutation at position 147 (A147Y) (SEQ ID NO:23). Amino acid residues 1-513 are the core sequences of the RSV F protein. The C-terminal sequences from amino acid residue 514 onwards comprise a foldon trimerization domain followed by a thrombin cleavage site, 6× His-tag (SEQ ID NO: 46), and a strep tag.

FIG. 22. Amino acid sequence of a modified soluble RSV F protein (DS-Cav1) comprising a to-tyrosine mutation at position 220 (V220Y) (SEQ ID NO:24). Amino acid residues 1-513 are the core sequences of the RSV F protein. The C-terminal sequences from amino acid residue 514 onwards comprise a foldon trimerization domain followed by a thrombin cleavage site, 6× His-tag (SEQ ID NO: 46), and a strep tag.

FIG. 23. Amino acid sequence of a modified soluble RSV F protein (DS-Cav1) comprising a to-tyrosine mutation at position 222 (E222Y) (SEQ ID NO:25). Amino acid residues 1-513 are the core sequences of the RSV F protein. The C-terminal sequences from amino acid residue 514 onwards comprise a foldon trimerization domain followed by a thrombin cleavage site, 6× His-tag (SEQ ID NO: 46), and a strep tag.

FIG. 24. Amino acid sequence of a modified soluble RSV F protein (DS-Cav1) comprising a to-tyrosine mutation at position 223 (F223Y) (SEQ ID NO:26). Amino acid residues 1-513 are the core sequences of the RSV F protein. The C-terminal sequences from amino acid residue 514 onwards comprise a foldon trimerization domain followed by a thrombin cleavage site, 6× His-tag (SEQ ID NO: 46), and a strep tag.

FIG. 25. Amino acid sequence of a modified soluble RSV F protein (DS-Cav1) comprising a to-tyrosine mutation at position 226 (K226Y) (SEQ ID NO:27). Amino acid residues 1-513 are the core sequences of the RSV F protein. The C-terminal sequences from amino acid residue 514 onwards comprise a foldon trimerization domain followed by a thrombin cleavage site, 6× His-tag (SEQ ID NO: 46), and a strep tag.

FIG. 26. Amino acid sequence of a modified soluble RSV F protein (DS-Cav1) comprising a to-tyrosine mutation at position 469 (V469Y) (SEQ ID NO:28). Amino acid residues 1-513 are the core sequences of the RSV F protein. The C-terminal sequences from amino acid residue 514 onwards comprise a foldon trimerization domain followed by a thrombin cleavage site, 6× His-tag (SEQ ID NO: 46), and a strep tag.

FIG. 27. Amino acid sequence of a modified soluble RSV F protein (subtype A) comprising to-tyrosine mutations at positions 222 (E222Y) and 469 (V469Y) (SEQ ID NO:29) designed to facilitate the formation of multiple di-tyrosine cross-links. Amino acid residues 1-513 are the core sequences of the RSV F protein. The C-terminal sequences from amino acid residue 514 onwards comprise a foldon trimerization domain followed by a thrombin cleavage site, 6× His-tag (SEQ ID NO: 46), and a strep tag.

FIG. 28. Amino acid sequence of a modified soluble RSV F protein (subtype A) comprising to-tyrosine mutations at positions 226 (K226Y) and 469 (V469Y) (SEQ ID NO:30) designed to facilitate the formation of multiple di-tyrosine cross-links. Amino acid residues 1-513 are the core sequences of the RSV F protein. The C-terminal sequences from amino acid residue 514 onwards comprise a foldon trimerization domain followed by a thrombin cleavage site, 6× His-tag (SEQ ID NO: 46), and a strep tag.

FIG. 29. Amino acid sequence of a modified soluble RSV F protein (DS-Cav1) comprising to-tyrosine mutations at positions 222 (E222Y) and 469 (V469Y) (SEQ ID NO:31) designed to facilitate the formation of multiple di-tyrosine cross-links. Amino acid residues 1-513 are the core sequences of the RSV F protein. The C-terminal sequences from amino acid residue 514 onwards comprise a foldon trimerization domain followed by a thrombin cleavage site, 6× His-tag (SEQ ID NO: 46), and a strep tag.

FIG. 30. Amino acid sequence of a modified soluble RSV F protein (DS-Cav1) comprising to-tyrosine mutations at positions 226 (K226Y) and 469 (V469Y) (SEQ ID NO:32) designed to facilitate the formation of multiple di-tyrosine cross-links. Amino acid residues 1-513 are the core sequences of the RSV F protein. The C-terminal sequences from amino acid residue 514 onwards comprise a foldon trimerization domain followed by a thrombin cleavage site, 6× His-tag (SEQ ID NO: 46), and a strep tag.

FIGS. 31A-31B. Ribbon diagrams depicting examples of two targeted positions in the RSV prefusion F protein trimer where intra-protomeric and intra-protomeric di-tyrosine cross-links can be introduced. (A) Side-view (and enlargement) of an engineered F1-F1 inter-protomeric di-tyrosine bond between a tyrosine introduced at position 185 (V185Y) and a tyrosine introduced at position 427 (K427Y) (SEQ ID NO:20). (B) Top-down view (and enlargement) of an engineered F1-F1 intra-protomeric di-tyrosine bond between an endogenous tyrosine at position 198 (198Y) and a tyrosine introduced at position 222 (E222Y) (SEQ ID NO:13). Targeted tyrosine residues are depicted in square boxes.

FIGS. 35A-35B. Di-tyrosine cross-linking stabilizes key epitope on RSV prefusion F protein. HEK 293 cells were transfected with constructs expressing the wild-type (WT) RSV-F or a variant containing the K226Y substitution. (A) 72 h post transfection, supernatants were cross-linked (DT) or left uncross-linked and total protein was measured by ELISA using a high-affinity human anti-hRSV antibody (100 ng/ml in PBS) that recognizes both pre- and post-fusion forms of RSV-F. (B) Following storage at 4 degrees C. for 16 days presentation of site ∅ was measured by ELISA using a preF specific human monoclonal antibody (2 μg/ml in PBS) that recognizes site ∅.

FIGS. 36A-36B. Sequence alignment of nucleotide sequences encoding the RSV F protein (full-length—with transmembrane and cytoplasmic domains) from RSV subtype A (SEQ ID NO:33—identified as "RSV_F_WT_Subtype_A" in the figure) and RSV subtype B (SEQ ID NO:34—identified as "RSV_F_WT_Subtype_B" in the figure). Nucleotides 1-1539 encode amino acid residues 1-513, which are the core ectodomain sequences of the RSV F protein. Nucleotides 1540 onwards comprise sequences that encode the endogenous RSV F transmembrane region and cytoplasmic tail.

FIG. 37. Nucleotide sequences encoding the RSV F protein (full-length—with transmembrane and cytoplasmic domains) from RSV subtype A that has been codon optimized for expression in human cells (SEQ ID NO:35). Nucleotides 1-1539 encode amino acid residues 1-513, which are the core ectodomain sequences of the RSV F protein. Nucleotides 1540 onwards comprise sequences that encode the endogenous RSV F transmembrane region and cytoplasmic tail.

FIG. 38. Nucleotide sequences encoding the RSV F protein (full-length—with transmembrane and cytoplasmic domains) from RSV subtype A that has been codon optimized for expression in hamster cells (such as CHO cells) (SEQ ID NO:36). Nucleotides 1-1539 encode amino acid residues 1-513, which are the core ectodomain sequences of the RSV F protein. Nucleotides 1540 onwards comprise sequences that encode the endogenous RSV F transmembrane region and cytoplasmic tail.

FIG. 39. Nucleotide sequences encoding the RSV F protein (full-length—with transmembrane and cytoplasmic domains) from RSV subtype A that has been codon optimized for expression in insect cells (such as SF9 insect cells) (SEQ ID NO:37). Nucleotides 1-1539 encode amino acid residues 1-513, which are the core ectodomain sequences of the RSV F protein. Nucleotides 1540 onwards comprise sequences that encode the endogenous RSV F transmembrane region and cytoplasmic tail.

FIG. 40. Nucleotide sequences encoding the RSV F protein (full-length—with transmembrane and cytoplasmic domains) from RSV subtype A that has been codon optimized for expression in mouse cells (SEQ ID NO:38). Nucleotides 1-1539 encode amino acid residues 1-513, which are the core ectodomain sequences of the RSV F protein. Nucleotides 1540 onwards comprise sequences that encode the endogenous RSV F transmembrane region and cytoplasmic tail.

FIG. 41. Nucleotide sequences encoding the RSV F protein (full-length—with transmembrane and cytoplasmic domains) from RSV subtype B that has been codon optimized for expression in human cells (SEQ ID NO:39). Nucleotides 1-1539 encode amino acid residues 1-513, which are the core ectodomain sequences of the RSV F protein. Nucleotides 1540 onwards comprise sequences that encode the endogenous RSV F transmembrane region and cytoplasmic tail.

FIG. 42. Nucleotide sequences encoding the RSV F protein (full-length—with transmembrane and cytoplasmic domains) from RSV subtype B that has been codon optimized for expression in hamster cells (such as CHO cells) (SEQ ID NO:40). Nucleotides 1-1539 encode amino acid residues 1-513, which are the core ectodomain sequences of the RSV F protein. Nucleotides 1540 onwards comprise sequences that encode the endogenous RSV F transmembrane region and cytoplasmic tail.

FIG. 43. Nucleotide sequences encoding the RSV F protein (full-length—with transmembrane and cytoplasmic domains) from RSV subtype B that has been codon optimized for expression in insect cells (such as SF9 insect cells) (SEQ ID NO:41). Nucleotides 1-1539 encode amino acid residues 1-513, which are the core ectodomain sequences of the RSV F protein. Nucleotides 1540 onwards comprise sequences that encode the endogenous RSV F transmembrane region and cytoplasmic tail.

FIG. 44. Nucleotide sequences encoding the RSV F protein (full-length—with transmembrane and cytoplasmic domains) from RSV subtype B that has been codon optimized for expression in mouse cells (SEQ ID NO:42). Nucleotides 1-1539 encode amino acid residues 1-513, which are the core ectodomain sequences of the RSV F protein. Nucleotides 1540 onwards comprise sequences that encode the endogenous RSV F transmembrane region and cytoplasmic tail.

FIG. 45. Nucleotide sequences encoding the RSV F protein (full-length—with transmembrane and cytoplasmic domains) from RSV subtype A that has been codon optimized for expression in human cells and also comprises DS-CAV1 mutations (SEQ ID NO:43). The mutations are shown in bold and with boxes surrounding the mutated codons. Nucleotides 1-1539 encode amino acid residues 1-513, which are the core ectodomain sequences of the RSV F protein. Nucleotides 1540 onwards comprise sequences that encode the endogenous RSV F transmembrane region and cytoplasmic tail.

FIG. 46. Nucleotide sequences encoding the RSV F protein (full-length—with transmembrane and cytoplasmic domains) from RSV subtype A that has been codon optimized for expression in human cells and also comprises DS mutations (SEQ ID NO:44). The mutations are shown in bold and with boxes surrounding the mutated codons. Nucleotides 1-1539 encode amino acid residues 1-513, which are the core ectodomain sequences of the RSV F protein. Nucleotides 1540 onwards comprise sequences that encode the endogenous RSV F transmembrane region and cytoplasmic tail.

FIG. 47. Nucleotide sequences encoding the RSV F protein (full-length—with transmembrane and cytoplasmic domains) from RSV subtype A that has been codon optimized for expression in human cells and also comprises CAV1 mutations (SEQ ID NO:45). The mutations are shown in bold and with boxes surrounding the mutated codons. Nucleotides 1-1539 encode amino acid residues 1-513, which are the core ectodomain sequences of the RSV F protein. Nucleotides 1540 onwards comprise sequences that encode the endogenous RSV F transmembrane region and cytoplasmic tail.

DETAILED DESCRIPTION OF THE INVENTION

Figure 32:
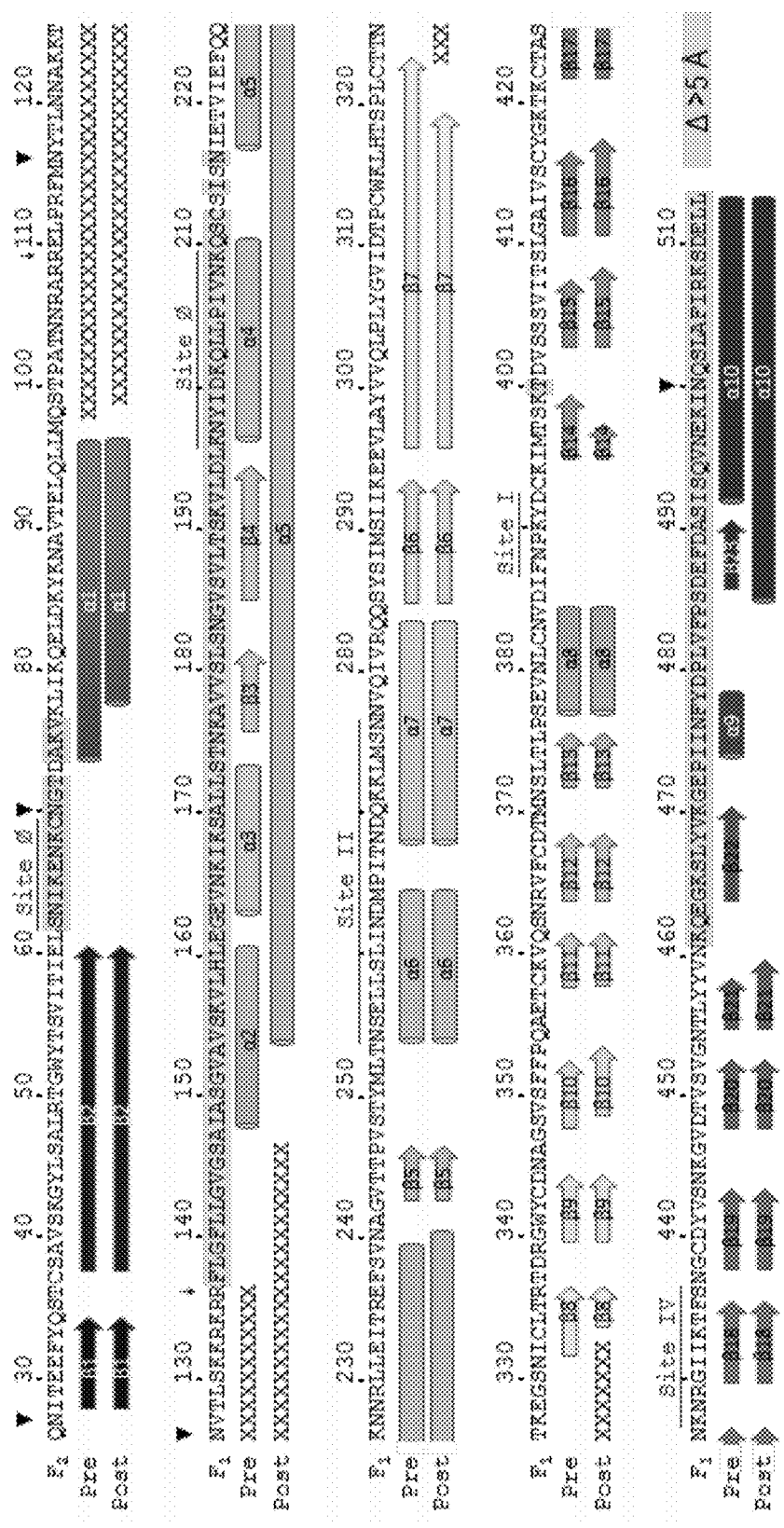
FIG. 32. Alignment of the RSV type A F protein sequence (SEQ ID NO: 47), and of the prefusion and post-fusion secondary structures. Cylinders and arrows below the sequence represent α-helices and β-strands, respectively. An "X" below the amino acid sequence indicates where the structure is disordered or missing. Gray shadowing indicates the position of residues that move more than 5Å in the transition from the prefusion to postfusion conformation. Black triangles indicate sites of N-linked glycosylation, text and lines above the amino acid sequence indicate the antigenic sites, and arrows indicate the position of the furin cleavage sites. Figure from McLellan et al., 2013, Science 340:1113-1117, supplementary materials.

The present invention provides, in part, RSV F polypeptides, proteins and protein complexes, such as those that can be or are stabilized in a pre-fusion conformation, methods of making such polypeptides, proteins and protein complexes, compositions (such as pharmaceutical compositions and vaccine compositions) comprising such polypeptides, proteins and protein complexes, and methods of use of such polypeptides, proteins and protein complexes, for example in vaccination methods, therapeutic methods and other methods. In some embodiments, the RSV polypeptides, proteins and protein complexes may be useful as conformationally-specific immunogens, for example in RSV vaccines.

Definitions and Abbreviations

As used in the present specification the terms "about" and "approximately," when used in relation to numerical values, mean within+ or −20% of the stated value.

As used herein the terms "protein" and "polypeptide" are used interchangeably, unless otherwise stated. As used herein the term "protein complex" refers to an assembly of two or more proteins or protein subunits, such as two or more monomers or protomers. Unless otherwise stated, all description herein that relates to proteins applies equally to protein complexes, and vice versa.

As used herein the terms "stabilized" and "locked" are used interchangeably, for example in relation to the effect of cross-linking in stabilizing or locking the RSV F protein in its pre-fusion conformation . These terms do not require 100% stability. Rather these terms denote a degree of improved or increased stability. For example, in some embodiments, when the term "stabilized" is used in relation to a RSV F protein cross-linked in its pre-fusion conformation, the term denotes that the pre-fusion conformation has greater stability than it would have had prior to or without such cross-linking. Stability, and relative stability, may be measured in various ways as described in other sections of this application, for example based on the half-life of the RSV pre-fusion conformation. The improvement or increase in stability may be to any degree that is useful or significant for the intended application. For example, in some embodiments stability may be increased by about 10%, 25%, 50%, 100%, 200% (i.e. 2-fold), 300% (i.e. 3-fold), 400% (i.e. 4-fold), 500% (i.e. 5-fold), 1000% (i.e. 10-fold), or more.

RSV F Polypeptides, Proteins & Protein Complexes

The RSV Fusion or "F" protein is the envelope glycoprotein of respiratory syncytial viruses. The RSV F protein may be translated as a single polypeptide precursor in either a soluble (without the transmembrane domain) or membrane-bound (with the transmembrane domain) form. This polypeptide forms a trimer, which may, in some situations, be proteolytically cleaved by one or more cellular proteases at conserved furin consensus cleavage sites to yield two disulfide-bonded fragments known as the F1 (C-terminal) and F2 (N-terminal) fragments. The F2 fragment includes approximately the first 83 amino acids of the RSV F precursor. Either the uncleaved precursor protein, or a heterodimer of the cleaved F2 and F1 fragments, can form an RSV F protomer. Three such protomers assemble to form the final RSV F protein complex, which is a homotrimer of three protomers.

The RSV F protein trimer mediates fusion of viral and cellular membranes. The pre-fusion conformation of the RSV F protein trimer (which may be referred to herein as "pre-F") is highly unstable (metastable). However, once the RSV virus docks with the cell membrane, the RSV F protein trimer undergoes a series of conformational changes and transitions to a highly stable post-fusion ("post-F") conformation. The RSV F protein is known to induce potent neutralizing antibodies (nAbs) that correlate with RSV protection. For example, immunization with the RSV F protein induces nAbs that are protective in humans (e.g. Synagis). Several neutralizing epitopes (sites I, II and IV) are present on the post-fusion form of RSV F protein. Recently, however, Magro et al. showed that incubation of human sera with the RSV F protein in its post-fusion conformation failed to deplete the majority of neutralizing activity against the F protein, indicating the presence of neutralizing antigenic sites unique to the pre-fusion conformation (Magro et al. 2012, PNAS 109(8): 3089). By x-ray crystallography, the epitopes recognized by palivizumab (Synagis), motavizumab (Numax), and that of the more recently discovered 101F monoclonal antibody (McLellan et al., 2010, J. Virol., 84(23): 12236-441; and McLellan et al., 2010, Nat. Struct. Mol. Biol., February 17(2): 248-50) were mapped. Most recently, McLellan et al. (Science 340:1113-1117 (2013)) solved the structure of the F protein in its pre-fusion conformation, which revealed a novel neutralizing epitope—site Ø—that is only displayed in the pre-fusion conformation, and to which a series of antibodies bind, e.g. 5C4, that are up to 50-fold more potently neutralizing than Synagis and Numax. Accordingly, there is mounting evidence that an RSV vaccine immunogen in this pre-fusion conformation and displaying site could elicit effective protection. However, to date the highly unstable (metastable) nature of the pre-fusion conformation of the RSV F protein has proved to be a significant barrier to the development of such a vaccine. Based on a comparison of the pre- and post-fusion RSV F structures of McLellan et al. there appear to be two regions of the F protein that undergo large conformational changes (>5 Å). These regions are located at the N- and C-termini of the F1 subunit (residues 137-216 and 461-513, respectively) (see FIG. 32). In the crystal structure of the RSV F protein held in its pre-fusion conformation by the D25-antibody bound to the site epitope, the C-terminal F1 residues can be stabilized in the pre-fusion conformation by appending a foldon trimerization domain. To stabilize the N-terminal region of F1, McLellan et al. found that binding of the antibody D25 was sufficient for crystallographic studies. However, for production of a vaccine immunogen alternative stabilization strategies are needed, such as those that do not require the RSV F protein to be bound to a large antibody molecule. One alternative approach that has been attempted involved the introduction of paired cysteine mutations (for disulfide bond formation) and cavity-filling mutations near the F1 N-terminus (see the DS-Cav1 RSV F protein variant described in McLellan et al. (2013) Science 342:592-598, which is hereby incorporated by reference in its entirety). However, crystallographic analysis of such variants revealed that the structure was only partially in the pre-fusion conformation. Accordingly, additional engineering of the RSV F protein is needed in order to achieve an immunogen for clinical vaccine development.

The present invention provides certain alternative approaches for stabilizing the RSV F protein in its pre-fusion conformation, including providing specific locations within the RSV F protein that can be or should be cross-linked, and providing mutant forms of the RSV F protein that can facilitate the formation of such cross-links. Such cross-links and mutations can be used alone (e.g. in the context of a wild type RSV F protein or in the context of a RSV F protein that does not comprise any man made mutations or other man made modifications), or can be used in combination with one or more other man made mutations, modifications, cross-links, or stabilization strategies. Thus, for example, the approaches described herein can be used in conjunction with the use of added foldon trimerization domains, stabilizing antibodies (such as D25), and/or other partially or potentially stabilizing modifications or mutations—such as those in the DS-Cav1 RSV F protein variant described by McLellan et al.

The present inventors have performed extensive analysis of the structure of the RSV F protein and have developed a variety of novel design strategies and novel engineered RSV F polypeptides, proteins and protein complexes. The present invention also provides methods for making and using such RSV F polypeptides, proteins, and protein complexes. In some embodiments, the present invention provides specific locations within the amino acid sequence of the RSV F protein at which, or between which, targeted cross-links can be made in order to "lock" the RSV F protein in its pre-F conformation. In some embodiments, the targeted cross-links are di-tyrosine cross-links. Where di-tyrosine cross-links are used, the present invention provides specific amino acid residues (or pairs of amino acid residues) that either comprise a pre-existing tyrosine residue or can be or are mutated to a tyrosine residue such that di-tyrosine cross-links can be made.

Throughout the present patent specification, when reference is made to specific amino acid residues or specific amino acid regions in the RSV F protein by referring to their amino residue number or numbers (such as amino acid residues 77, 88, 97, or 222, for example), and unless otherwise stated, the numbering is based on the RSV amino acid sequences provided herein in the sequence listing and in the Figures (see, for example, FIG. 6 and SEQ ID NO: 1). However, it should be noted, and one of skill in the art will understand, that different RSV sequences may have different numbering systems, for example, if there are additional amino acid residues added or removed as compared to SEQ ID NO: 1. As such, it is to be understood that when specific amino acid residues are referred to by their number, the description is not limited to only amino acids located at precisely that numbered position when counting from the beginning of a given amino acid sequence, but rather that the equivalent/corresponding amino acid residue in any and all RSV F sequences is intended—even if that residue is not at the same precise numbered position, for example if the RSV sequence is shorter or longer than SEQ ID NO: 1, or has insertions or deletions as compared to SEQ ID NO: 1. One of skill in the art can readily determine what is the corresponding/equivalent amino acid position to any of the specific numbered residues recited herein, for example by aligning a given RSV F sequence to SEQ ID NO. 1 or to any of the other RSV F amino acid sequences provided herein.

The present invention provides RSV F protein and polypeptide amino acid sequences, and compositions and methods comprising such sequences. However, the invention is not limited to the specific RSV F sequences disclosed herein. Rather the present invention contemplates variations, modifications and derivatives of the specific sequences provided herein.

In some embodiments, the RSV F polypeptides, proteins or protein complexes of the present invention can be derived from (or can comprise, consist essentially of, or consist of) the amino acid sequences of any suitable RSV F polypeptide, protein or protein complex sequence known in the art, including, without limitation: the amino acid sequence of RSV subtype A (for example in soluble form (SEQ ID NO:1, or amino acid residues 1-513 thereof) or in a full-length form (SEQ ID NO:2)); the amino acid sequence of RSV subtype B (for example in soluble form (SEQ ID NO:3, or amino acid residues 1-513 thereof) or in full-length form (SEQ ID NO:4)); the amino acid sequence of RSV variant DS-Cav1 (for example in soluble form (SEQ ID NO:5, or amino acid residues 1-513 thereof) or in full-length form (SEQ ID NO:6)); the amino acid sequence of RSV variant Cav1 (for example in soluble form (SEQ ID NO:7, or amino acid residues 1-513 thereof) or in full-length form (SEQ ID NO:8)); or the amino acid sequence of RSV variant DS (for example in soluble form (SEQ ID NO:9, or amino acid residues 1-513 thereof) or in full-length form (SEQ ID NO:10)), or any fragment thereof. In some embodiments, the RSV F proteins and polypeptides of the present invention can be derived from (or can comprise, consist essentially of, or consist of) amino acid sequences that have at least about 60%, 65%, 70%, 75%, 80%, 85%, 90%, 95%, 98%, or 99% sequence identity to any known RSV F sequences or RSV F ectodomain sequences (including but not limited to amino acid residues 1-513 of SEQ ID NOs:1-10, or SEQ ID NOs:1-10), or to RSV F sequences from any known RSV groups, subgroups, families, subfamilies, types, subtypes, genera, species, strains, and/or clades, or any fragment thereof. It should be noted that amino acid residues 1-513 of the various RSV F sequences provided herein are core RSV F ectodomain sequences. Amino acid residues 514 onwards in all such sequences comprise additional domains that may be present in some embodiments but not in others. In some embodiments variants of such additional domains may be present. For example, amino acid residues 514 onwards in all soluble RSV F sequences provided herein comprise an optional foldon trimerization domain, thrombin cleavage site, 6× His-tag (SEQ ID NO: 46), and a strep tag. In some embodiments these additional sequences may be absent, modified, rearranged or replaced. For example, in some embodiments different trimerization domains may be used, or different epitope tags may be used. Similarly, amino acid residues 514 onwards in all "full-length" or membrane-bound RSV F sequences provided herein comprise an optional RSV F protein transmembrane region and cytoplasmic tail. In some embodiments these additional sequences may be absent, modified, rearranged or replaced, for example with different transmembrane or cytoplasmic domains.

In some embodiments the present invention provides RSV F polypeptides, proteins, and/or protein complexes that comprise one or more artificially-introduced cross-links, wherein at least one of the following amino acid residues within the RSV F polypeptides, proteins, and/or protein complexes is artificially cross-linked to another amino acid residue in the RSV F protein: Y33, K77, N88, M97, A147, S150, S155, H159, N183, V185, V187, Y198, V220, E222, F223, K226, S255, Y286, K427 and V469. In some such embodiments the cross-link is a di-tyrosine cross-link.

In some embodiments the present invention provides RSV F polypeptides, proteins, and/or protein complexes that comprise one or more artificially-introduced cross-links, wherein such artificially introduced cross-links connect two of the following amino acid residues: Y33, K77, N88, M97, A147, S150, S155, H159, N183, V185, V187, Y198, V220, E222, F223, K226, S255, Y286, K427 and V469. In some such embodiment the cross-link is a di-tyrosine cross-link.

In some embodiments the present invention provides RSV F polypeptides, proteins, and/or protein complexes in which the amino acid residues in one or more of the following pairs of amino residues are cross-linked to each other by an artificially introduced cross-link: 147/286, 198/220, 198/222, 198/223, 198/226, 33/496, 77/222, 88/255, 97/159, 183/427, 185/427, and 187/427. In some such embodiments the cross-link is a di-tyrosine cross-link.

In some embodiments the present invention provides RSV F polypeptides, proteins, and/or protein complexes comprising an artificially introduced cross-link between two of the following regions: the F1 mobile N-terminus (residues 137-216), α2 (residues 148-160), α3 (residues 163-173), β3 (residues 176-182), α4 (residues 186-195), α4 (residues 197-211), the F1 mobile C-terminus (residues 461-513), (322 (residues 464-471), α9 (residues 474-479), β23 (residues 486-491), and α10 (residues 493-514). In some such embodiments the cross-link is a di-tyrosine cross-link.

In some embodiments the present invention provides RSV F polypeptides, proteins, and/or protein complexes comprising an artificially introduced cross-link between two of the following regions: amino acid residues from about position 67 to about position 87, amino acid residues from about position 78 to about position 98, amino acid residues from about position 87 to about position 107, amino acid residues from about position 137 to about position 157, amino acid residues from about position 140 to about position 160, amino acid residues from about position 145 to about position 165, amino acid residues from about position 149 to about position 169, amino acid residues from about position 173 to about position 193, amino acid residues from about position 175 to about position 195, from about position 177 to about position 197, amino acid residues from about position 188 to about position 208, amino acid residues from about position 210 to about position 230, amino acid residues from about position 212 to about position 232, amino acid residues from about position 213 to about position 233, amino acid residues from about position 216 to about position 236, amino acid residues from about position 245 to about position 265, amino acid residues from about position 276 to about position 296, amino acid residues from about position 417 to about position 437, and amino acid residues from about position 459 to about position 479. In some such embodiments the cross-link is a di-tyrosine cross-link.

In embodiments where the RSV F polypeptides, proteins, and/or protein complexes of the invention comprise one or more di-tyrosine cross-links, di-tyrosine cross-links may be introduced between two endogenous tyrosine residues, between two tyrosine residues originating from "to-tyrosine" mutations, or between a tyrosine residue originating from a "to-tyrosine" mutation and an endogenous tyrosine residue. In some embodiments, more than one di-tyrosine cross-link is introduced into a RSV F protein or polypeptide.

In embodiments where the RSV F polypeptides, proteins, and/or protein complexes of the invention comprise one or more di-tyrosine cross-links, non-limiting examples of amino acid positions where a "to-tyrosine" mutation can be introduced include K77, N88, M97, A147, S150, S155, H159, N183, V185, V187, V220, E222, F223, K226, S255, K427 and V469 (see FIG. 6), or any combination thereof.

In embodiments where the RSV F polypeptides, proteins, and/or protein complexes of the invention comprise one or more di-tyrosine cross-links, non-limiting examples of pre-existing or endogenous tyrosine residues that can be used to form a di-tyrosine cross-link include Y33, Y198 and Y286 (see FIG. 6), or any combination thereof.

In embodiments where the RSV F polypeptides, proteins, and/or protein complexes of the invention comprise one or more di-tyrosine cross-links, non-limiting examples of residue pairs between which a di-tyrosine cross-link can be introduced include 147/286, 198/220, 198/222, 198/223, 198/226, 33/496, 77/222, 88/255, 97/159, 183/427, 185/427, and 187/427, or any combination thereof.

In embodiments where the RSV F polypeptides, proteins, and/or protein complexes of the invention comprise one or more di-tyrosine cross-links, non-limiting examples of regions or secondary structures of the RSV F protein from which amino acids may be selected for tyrosine substitution and/or di-tyrosine cross-linking include the F1 mobile N-terminus (residues 137-216), α2 (residues 148-160), α3 (residues 163-173), β3 (residues 176-182), β4 (residues 186-195), α4 (residues 197-211), the F1 mobile C-terminus (residues 461-513), β22 (residues 464-471), α9 (residues 474-479), β23 (residues 486-491), and α10 (residues 493-514). Non-limiting examples of other regions of RSV F protein from which one or more amino acids may be selected for tyrosine substitution and/or cross-linking include residues from about position 67 to about position 87, from about position 78 to about position 98, from about position 87 to about position 107, from about position 137 to about position 157, from about position 140 to about position 160, from about position 145 to about position 165, from about position 149 to about position 169, from about position 173 to about position 193, from about position 175 to about position 195, from about position 177 to about position 197, from about position 188 to about position 208, from about position 210 to about position 230, from about position 212 to about position 232, from about position 213 to about position 233, from about position 216 to about position 236, from about position 245 to about position 265, from about position 276 to about position 296, from about position 417 to about position 437, and from about position 459 to about position 479.

In some embodiments, the present invention provides RSV F polypeptides, proteins, and/or protein complexes that are derived from, comprise, consist essentially of, or consist of, the amino acid sequence of SEQ ID NO:11, 12, 13, 14, 15, 16, 17, 18, 19, 20, 21, 22, 23, 24, 25, 26, 27, 28, 29, 30, 31, or 32, or amino acid residues 1-513 thereof, (each of which are mutants of the RSV F amino acid sequence that comprise one or more "to tyrosine" mutations to facilitate di-tyrosine cross-linking and to facilitate "locking" of the RSV F protein in its pre-F conformation), or any fragment thereof, such as fragments comprising amino acid residues 1-513 thereof, and/or fragments comprising the F1 or F2 fragments of the RSV F protein, or any other fragments of the RSV F protein that may be generated proteolytically and/or that may be assembled into or form part of a functional RSV F protein. In some embodiments, the present invention provides RSV F polypeptides, proteins, and/or protein complexes that are derived from, comprise, consist essentially of, or consist of, an amino acid sequence having at least about 75%, 80%, 85%, 90%, 95%, 98%, or 99% sequence identity to SEQ ID NO: 11, 12, 13, 14, 15, 16, 17, 18, 19, 20, 21, 22, 23, 24, 25, 26, 27, 28, 29, 30, 31, or 32, or amino acid residues 1-513 thereof, or any fragment thereof.

Non-limiting examples of amino acid positions in an RSV F protein or polypeptide to which di-tyrosine cross-links may be targeted include Y33 (pre-existing Tyr residue) and V469Y (to-Tyr substitution), where a F2-F1 intra-protomer bond will form, the positions Y198 (pre-existing Tyr residue) and E222Y (to-Tyr substitution), where an F1-F1 intra-molecular bond would form, the positions K77Y (to-Tyr substitution) and E222Y (to-Tyr substitution), where an $F_2$-$F_1$ inter-protomer bond would form, the positions N88Y (to-Tyr substitution) and S255Y (to-Tyr substitution), where an $F_2$-$F_1$ inter-protomer bond would form, the positions M97Y (to-Tyr substitution) and H159Y (to-Tyr substitution), where an $F_2$-$F_1$ inter-protomer bond would form, the positions V185Y (to-Tyr substitution) and K427Y (to-Tyr substitution), where an $F_1$-$F_1$ inter-protomer bond would form, and the positions N183Y (to-Tyr substitution) and K427Y (to-Tyr substitution), where an $F_1$-$F_1$ inter-protomer bond would form. These positions were initially identified by analysis of the atomic level structure of the RSV prefusion F protein. Further non-limiting examples include positions A147Y (to-Tyr substitution) and Y286 (pre-existing Tyr), Y198 (pre-existing Tyr residue) and V220Y (to-Tyr substitution), Y198 (pre-existing Tyr residue) and F223Y (to-Tyr substitution), Y198 (pre-existing Tyr residue) and K226Y (to-Tyr substitution), V187Y (to-Tyr substitution) and K427Y (to-Tyr substitution) and N88Y (to-Tyr substitution) and S255Y (to-Tyr substitution). In some embodiments, the RSV polypeptides, proteins or protein complexes of the invention comprise one of the above listed di-tyrosine cross-links. In some embodiments, the RSV polypeptides, proteins or protein complexes of the invention comprise two of the above listed di-tyrosine cross-links. In some embodiments, the RSV polypeptides, proteins or protein complexes of the invention comprise three of the above listed di-tyrosine cross-links. In some embodiments, the RSV polypeptides, proteins or protein complexes of the invention comprise four of the above listed di-tyrosine cross-links. In some embodiments, the RSV polypeptides, proteins or protein complexes of the invention comprise five or more of the above listed di-tyrosine cross-links. In some embodiments, the RSV polypeptides, proteins or protein complexes of the invention comprise any combination or one or more of the above listed di-tyrosine cross-links.

Non-limiting examples of RSV F proteins designed to have more than one di-tyrosine cross-link include RSV F proteins with two "to-tyrosine" mutations (E222Y/V469Y), for example, derived from subtype A (SEQ ID NO:29) or DS-Cav1 (SEQ ID NO:31) where the tyrosine substituted at position 222 is designed to pair with the endogenous tyrosine at position 198, and the tyrosine substituted at position 469 is designed to pair with the endogenous tyrosine at position 33, thus stabilizing the RSV F protein by the formation of two di-tyrosine cross-links; and RSV F proteins with two to-tyrosine mutations (K226Y/V469Y), for example, derived from subtype A (SEQ ID NO:30) or DS-Cav1(SEQ ID NO:32) where the tyrosine substituted at position 226 is designed to pair with the endogenous tyrosine at position 198, and the tyrosine substituted at position 469 is designed to pair with the endogenous tyrosine at position 33, thus stabilizing the F protein by the formation of two di-tyrosine cross-links.

As described above, each protomer of the mature RSV F trimer may be cleaved into two distinct polypeptide chains termed F1 and F2 which associate non-covalently to form a protomer. A bond between a F1 polypeptide and a F2 polypeptide within the same protomer is an example of an inter-molecular bond and an intra-protomer bond. The invention provides exemplary RSV F proteins and polypeptides comprising cross-links designed to stabilize this interaction, including without limitation, SEQ ID NO:16 (V469Y, where the introduced tyrosine at position 469 is designed to pair with endogenous tyrosine 33), SEQ ID NO:17 (K77Y/E222Y, designed to form a di-tyrosine pair between the introduced tyrosines), SEQ ID NO:18 (N88Y/S255Y, designed to form a di-tyrosine pair between the introduced tyrosines), and SEQ ID NO:19 (M97Y/H159Y, designed to form a di-tyrosine pair between the introduced tyrosines), as well as RSV F polypeptides, proteins or protein complexes derived from such sequences and including the specific "to tyrosine" mutations present in such sequences. The invention also provides exemplary RSV F proteins and polypeptides comprising cross-links designed to hold two protomers of the trimer together (inter-molecular, inter-protomer bond), including without limitation, SEQ ID NO:20 (V185Y/K427Y), SEQ ID NO:21 (V187Y/K427Y) SEQ ID NO:22 (N183Y/K427Y), as well as RSV F polypeptides, proteins or protein complexes derived from such sequences and including the specific "to tyrosine" mutations present in such sequences. In each of these proteins, one introduced tyrosine in one protomer is designed to pair with the other introduced tyrosine on the adjacent protomer. For example, in SEQ ID NO:20 (V185Y/K427Y), the tyrosine at position 185 on "protomer A" would form a di-tyrosine bond with the tyrosine at position 427 on "protomer B" (see FIG. 31A).

In some embodiments, the F1 polypeptide of a RSV F protein is cross-linked with the F2 polypeptide of the same protomer (inter-molecular/intra-protomer bond). In some embodiments, the F1 polypeptide is intra-molecularly cross-linked (e.g., both tyrosines of the cross-link are located within the same F1 polypeptide). In some embodiments, the F2 polypeptide is intra-molecularly cross-linked (e.g., both tyrosines of the cross-link are located within the same F1 polypeptide). In some embodiments, the F1 polypeptide of the RSV prefusion F protein is cross-linked with the F1 polypeptide of an adjacent protomer (inter-protomer bond). In some embodiments, the F1 polypeptide of the RSV prefusion F protein is cross-linked with the F2 polypeptide of an adjacent protomer (inter-protomer bond).

The transition from the pre-F to the post-F structures involves very significant rearrangement of parts of the RSV protein, in particular the C- and N-termini of $F_1$, while the rest of the protein moves significantly less. In order to stabilize the preF conformation by the methods of this invention, parts of the protein that move significantly (e.g. more than 5Å) can be attached to parts of the protein that move less significantly (e.g. less than 5Å), either between two residues of the $F_1$ chain of a single protomer, between two residues of the $F_2$ chain of single protomer, between one residue of the $F_1$ chain and one residue of the $F_2$ chain within the same protomer, or between $F_1$ and/or $F_2$ residues of two adjacent protomers. Alternatively, parts of the protein that move significantly (e.g. more than 5Å) can be attached to other parts of the protein that also move significantly (e.g. more than 5Å), also either between two residues of the $F_1$ chain, between two residues of the $F_2$ chain, between one residue of the $F_1$ chain and one residue of the $F_2$ chain of within the same protomer, or between $F_1$ and/or $F_2$ residues of two adjacent protomers. Covalent attachment of moving parts to either moving or non-moving parts prevents the transition from the prefusion structure to either intermediate structures or to the postfusion structure.

Positions in $F_2$ that move more than 5Å in the pre-fusion to post-fusion transition include the positions 62 through 76, whereas positions 26 through 61 and 77 through 97 move less than 5Å (and positions 98-109 have yet to be determined in the pre-fusion structure). Positions in $F_1$ that move more than 5Å in the pre-F to post-F transition include the positions 137 through 216 ($F_1$ mobile N-terminus) and 461 through 513 ($F_1$ mobile C-terminus). The $F_1$ mobile N-terminus of the preF structure further comprises the 2 (positions 148 through 173), 3 (positions 176 through 182), and 4 (positions 197 through 211) secondary structures that can each either be attached to one another, or to other moving or non-moving parts within the same protomer or between protomers of the F protein trimer (complex consisting of three protomers). The $F_1$ mobile C-terminus of the preF structure further comprises the 22 (positions 464 479), 3 (positions 486 t structures that can each either be attached to one another, or to other moving or non-moving parts within the same protomer or between protomers of the F protein trimer. (See FIG. 32.)

In some embodiments (including all of those described above, and those involving RSV F polypeptides, proteins, and/or protein complexes having any of the specific amino acid sequences recited herein, and those involving variants or fragments of such RSV F polypeptides, proteins, and/or protein complexes having less than 100% identity to the specific amino acid sequence provided herein), the RSV F polypeptides, proteins, and/or protein complexes of the invention should have one or more desired properties such as being capable of (1) forming the pre-F conformation, (2) being "locked" in the pre-F conformation by cross-linking, (3) binding to a pre-F specific antibody, (4) binding to an antibody that binds to site 0, (5) binding to a neutralizing antibody, (6) binding to a broadly neutralizing antibody, (7) binding to an antibody selected from the group consisting of D25, AM22, 5C4, 101F (8) binding to palivizumab (Synagis), (9) binding to and/or activating a B cell receptor, (10) eliciting an antibody response in an animal, (11) eliciting a protective antibody response in an animal, (12) eliciting production of neutralizing antibodies in an animal, (13) eliciting production of broadly neutralizing antibodies in an animal, (14) eliciting production of antibodies that recognize quaternary neutralizing epitopes (QNEs) in an animal, and/or (15) eliciting a protective immune response in an animal.

Unless otherwise stated, all description herein that relates to specific RSV F polypeptides, proteins, and protein complexes, relates equally to all homologs, orthologs, analogs, derivatives, mutant forms, fragments, chimeras, fusion proteins etc. thereof, such as those that have certain desired properties or features (for example those that are in the pre-F conformation, or that are capable of forming part of a complex having the desired pre-F conformation, or that have desired functional properties, including, but not limited to, being capable of binding to, or eliciting the production of, one or more anti-RSV antibodies, such as antibodies that are specific to the RSV pre-F conformation and/or that bind to the 0 site).

Similarly, all description herein that relates to specific polypeptides, proteins, and/or protein complexes polypeptides, proteins, and/or protein complexes (e.g. those having specific amino acid sequences or those from a specific RSV type, subtype, or strain) relates equally to other related forms of such polypeptides, proteins, and/or protein complexes that may exist in nature (for example in different RSV types, subtypes or strains) or that are related to the specific sequences provides herein but have been altered artificially in some way, such as by recombinant means, chemical means, or any other means. The polypeptides, proteins, and/or protein complexes described herein can have, or can be derived from, the nucleotide and/or amino acid sequences of any suitable RSV polypeptides, proteins, and/or protein complexes known in the art. In some embodiments, the RSV F polypeptides, proteins, and/or protein complexes of the invention may be, or may be derived from, derivatives and/or analogs of specific specific RSV F polypeptides, proteins, and/or protein complexes described herein or known in the art, including proteins that are substantially homologous to any such proteins, or fragments thereof (e.g., in various embodiments, those having at least about 40% or 50% or 60% or 70% or 75% or 80% or 85% or 90% or 95% or 98% or 99% identity with an amino acid or nucleic acid sequence of any specific RSV F polypeptides, proteins, and/or protein complexes described herein or known in the art, when aligned using any suitable method known to one of ordinary skill in the art, such as, for example, using a computer homology program known in the art) or whose encoding nucleic acid is capable of hybridizing to a coding nucleic acid sequence of a protein of the invention, under high stringency, moderate stringency, or low stringency conditions.

In some embodiments, the invention provides fragments of the specific RSV F polypeptides, proteins, and protein complexes described herein, such as those comprising, consisting essentially of, or consisting of, at least about 10 amino acids, 20 amino acids, 50 amino acids, 100 amino acids, 200 amino acids, or 500 amino acids.

In some embodiments one or more amino acid residues within a specific RSV F polypeptide, protein, and/or protein complex as described herein, or as known in the art, can be deleted, added, or substituted with another amino acid. In embodiments where such mutations are introduced, the RSV F polypeptides, proteins, or protein complexes can be microsequenced to determine a partial amino acid sequence. In other embodiments the nucleic acid molecules encoding the RSV F polypeptides, proteins, and/or protein complexes can be sequenced to identify and/or confirm the introduction of mutations.

In some embodiments, one or more amino acid residues can be substituted by another amino acid having a similar polarity and that may acts as a functional equivalent, resulting in a silent alteration. In some embodiments substitutions for an amino acid within the sequence may be selected from other members of the class to which the amino acid belongs e.g. to create a conservative substitution. For example, the nonpolar (hydrophobic) amino acids include alanine, leucine, isoleucine, valine, proline, phenylalanine, tryptophane and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such substitutions are generally understood to be conservative substitutions.

In some embodiments artificial, synthetic, or non-classical amino acids or chemical amino acid analogs can be used to make the RSV F polypeptides, proteins, and/or protein complexes of the invention. Non-classical amino acids include, but are not limited to, the D-isomers of the common amino acids, fluoro-amino acids, and "designer" amino acids such as β-methyl amino acids, Cγ-methyl amino acids, Nγ-methyl amino acids, and amino acid analogs in general. Additional non-limiting examples of non-classical amino acids include, but are not limited to: α-aminocaprylic acid, Acpa; (S)-2-aminoethyl-L-cysteine/HCl, Aecys; aminophenylacetate, Afa; 6-amino hexanoic acid, Ahx; γ-amino isobutyric acid and α-aminoisobytyric acid, Aiba; alloisoleucine, Aile; L-allylglycine, Alg; 2-amino butyric acid, 4-aminobutyric acid, and α-aminobutyric acid, Aba; p-aminophenylalanine, Aphe; b-alanine, Bal; p-bromophenylalaine, Brphe; cyclohexylalanine, Cha; citrulline, Cit; β-chloroalanine, Clala; cycloleucine, Cle; p-cholorphenylalanine, Clphe; cysteic acid, Cya; 2,4-diaminobutyric acid, Dab; 3-amino propionic acid and 2,3-diaminopropionic acid, Dap; 3,4-dehydroproline, Dhp; 3,4-dihydroxylphenylalanine, Dhphe; p-flurophenylalanine, Fphe; D-glucoseaminic acid, Gaa; homoarginine, Hag; δ-hydroxylysine/HCl, Hlys; DL-β-hydroxynorvaline, Hnvl; homoglutamine, Hog; homophenylalanine, Hoph; homoserine, Hos; hydroxyproline, Hpr; p-iodophenylalanine, Iphe; isoserine, Ise; α-methylleucine, Mle; DL-methionine-S-methylsulfoniumchloide, Msmet; 3-(1-naphthyl) alanine, 1Nala; 3-(2-naphthyl) alanine, 2Nala; norleucine, Nle; N-methylalanine, Nmala; Norvaline, Nva; O-benzylserine, Obser; O-benzyltyrosine, Obtyr; O-ethyltyrosine, Oetyr; O-methylserine, Omser; O-methylthreonine, Omthr; O-methyltyrosine, Omtyr; Ornithine, Orn; phenylglycine; penicillamine, Pen; pyroglutamic acid, Pga; pipecolic acid, Pip; sarcosine, Sar; t-butylglycine; t-butylalanine; 3,3,3-trifluroalanine, Tfa; 6-hydroxydopa, Thphe; L-vinylglycine, Vig; (-)-(2R)-2-amino-3-(2-aminoethylsulfonyl) propanoic acid dihydroxochloride, Aaspa; (2S)-2-amino-9-hydroxy-4,7-dioxanonanoic acid, Ahdna; (2S)-2-amino-6-hydroxy-4-oxahexanoic acid, Ahoha; (-)-(2R)-2-amino-3-(2-hydroxyethylsulfonyl) propanoic acid, Ahsopa; (-)-(2R)-2-amino-3-(2-hydroxyethylsulfanyl) propanoic acid, Ahspa; (2S)-2-amino-12-hydroxy-4,7,10-trioxadodecanoic acid, Ahtda; (2S)-2,9-diamino-4,7-dioxanonanoic acid, Dadna; (2S)-2,12-diamino-4,7,10-trioxadodecanoic acid, Datda; (S)-5,5-difluoronorleucine, Dfnl; (S)-4,4-difluoronorvaline, Dfnv; (3R)-1-1-dioxo-[1,4]thiaziane-3-carboxylic acid, Dtca; (S)-4,4,5,5,6,6,6-heptafluoronorleucine, Hfnl; (S)-5,5,6,6,6-pentafluoronorleucine, Pfnl; (5)-4,4,5,5,5-pentafluoronorvaline, Pfnv; and (3R)-1,4-thiazinane-3-carboxylic acid, Tca. Furthermore, the amino acid can be D (dextrorotary) or L (levorotary). For a review of classical and non-classical amino acids, see Sandberg et al., 1998 (Sandberg et al., 1998. New chemical descriptors relevant for the design of biologically active peptides. A multivariate characterization of 87 amino acids. J Med Chem 41(14): pp. 2481-91).

Nucleic Acids

In addition to providing certain RSV F polypeptides, proteins, and/or protein complexes, as described herein, the present invention also provides nucleic acids encoding such RSV F polypeptides, proteins, and/or protein complexes, and compositions and vectors comprising such nucleic acids. Such nucleic acids can be obtained or made using any suitable method known in the art. For example, nucleic acid molecules encoding RSV F polypeptides, proteins, and/or protein complexes may be obtained from cloned DNA or made by chemical synthesis. In some embodiments the nucleic acids may be obtained by reverse transcribing RNA prepared by any of the methods known to one of ordinary skill in the art, such as random- or poly A-primed reverse transcription. Whatever the source, a nucleic acid molecule encoding a RSV F polypeptide, protein, and/or protein complex of the present invention can be cloned into any suitable vector, such as those to be used for propagation of the nucleic acid molecule or those to be used for expression of the nucleic acid molecule. The nucleic acid may be cleaved at specific sites using various restriction enzymes, if needed. In embodiments requiring expression, the nucleic acid can be operatively linked to a promoter suitable for directing expression in the desired cell type, such as a mammalian cell or an insect cell, and may be incorporated into any suitable expression vector, such as a mammalian or insect expression vector.

In some embodiments, the RSV F polypeptides, proteins or protein complexes of the present invention can derived from nucleic sequences that encode (or that comprise, consist essentially of, or consist of nucleotide sequences that encode) any suitable RSV F polypeptide, protein or protein complex sequence known in the art, or any fragment thereof, including, without limitation: a nucleotide sequence that encodes the wild-type (WT) full length F protein from RSV subtype A (for example, SEQ ID NO:33), or a nucleotide sequence that encodes the wild-type (WT) full length F protein from RSV subtype B (for example, SEQ ID NO:34), or variants of such sequences that have been codon optimized for expression in cells of any particular species of interest, or that contain any mutations of interest. For example, in some embodiments, the RSV F polypeptides, proteins or protein complexes of the present invention can derived from nucleotide sequences that encode the F protein of RSV F type A, but that have been codon optimized for expression in human (e.g. SEQ ID NO:35), hamster (e.g. SEQ ID NO:36), insect (e.g. SEQ ID NO:37), or mouse cells (e.g. SEQ ID NO:38), or optimized for expression in any other cell type. Similarly, in some embodiments, the RSV F polypeptides, proteins or protein complexes of the present invention can derived from nucleotide sequences that encode the F protein of RSV F type B, but that have been codon optimized for expression in human (e.g. SEQ ID NO:39), hamster (e.g. SEQ ID NO:40), insect (e.g. SEQ ID NO:41), or mouse cells (e.g. SEQ ID NO:42), or optimized for expression in any other cell type. Similarly, in some embodiments, the RSV F polypeptides, proteins or protein complexes of the present invention can derived from nucleotide sequences that encode the F protein of RSV F type A or B, and which may or may not have been codon optimized for expression cells of any given species of interest, and which also comprise one or more other mutations of interest. For example, in some embodiments, the RSV F polypeptides, proteins or protein complexes of the present invention can be derived from nucleotide sequences that comprise DS-CAV1 (SEQ ID NO:43), DS (SEQ ID NO: 44), and/or CAV1 (SEQ ID NO:45) mutant sequences. Although the three specific sequences provided in SEQ ID NO:s 43, 44, and 45 comprise the DS, CAV1, and DS-CAV1 mutations in the context of a human codon optimized full-length RSV type A sequence, such mutations, or indeed any other mutations of interest (including all of the "to-tyrosine" mutations of the invention), could equally be present in a backbone of any other suitable RSV type A or type B sequence, including, but not limited to, those sequences that have been optimized for expression in any species of interest, or that include any mutations of interest, or that include only certain portions of the RSV type A or B sequences, such as, for example, only nucleotides 1-1539 that encode only the RSV F ectodomain (without the transmembrane and/or cytoplasmic domains).

One of skill in the art will recognize that there are a variety of nucleotide sequences that can encode the various RSV F polypeptides and proteins described herein, and all such nucleotide sequences are intended to fall within the scope of the present invention. For example, in some embodiments, the RSV F proteins and polypeptides of the present invention can be derived from nucleotide sequences that have at least about 60%, 65%, 70%, 75%, 80%, 85%, 90%, 95%, 98%, or 99% sequence identity to any known nucleotide sequences that encode an RSV F protein, including, but not limited to, any of those illustrated herein (including SEQ ID NOs: 33, 34, 35, 36, 37, 38, 39, 40, 41, 42, 43, 44, and 45), or that have at least about 60%, 65%, 70%, 75%, 80%, 85%, 90%, 95%, 98%, or 99% sequence identity to nucleotides 1-1539 thereof (which encode the ectodomain sequences), or that have at least about 60%, 65%, 70%, 75%, 80%, 85%, 90%, 95%, 98%, or 99% sequence identity to nucleotide sequences that encode RSV F proteins from any known RSV groups, subgroups, families, subfamilies, types, subtypes, genera, species, strains, and/or clades, or any fragment thereof.

Furthermore, one or skill in the art can readily visualize, or make, nucleic acid molecules that comprise any one or more of the specific "to-tyrosine" mutations described herein, for example, by locating the nucleotide codon that encodes the specific amino acid residue to be mutated, and mutating the nucleotides at that codon as necessary to result in a tyrosine-encoding codon.

Cross-Linking

In some embodiments the RSV F polypeptides and/or proteins of the invention are assembled into protein complexes having a desired conformational structure, such as the pre-F conformation, and are cross-linked in order to stabilize that conformation. Details of particular regions of the RSV F protein that can be cross-linked, as well as particular RSV mutants designed to facilitate such cross-linking, are described in other sections of this application. In some embodiments the cross-links may be used to stabilize the tertiary and/or quarternary structures of the RSV prefusion F protein. In some embodiments, the cross-linking may be intra-and/or intermolecular cross-linking. In some embodiments, the cross-links that are used are targeted cross-links. In some embodiments, the cross-links that are used are stable under physiological conditions. In some embodiments, the cross-links that are used do not lead to aggregate formation of the RSV prefusion F protein, for example during expression and/or during storage (such as storage of compositions comprising high concentrations of the RSV prefusion F protein). In some embodiments the introduction of such cross-links may enhance the effectiveness of the RSV polypeptides, proteins and proteins of the invention as immunogens, such as vaccine immunogens. In some embodiments the introduction of such cross-links may stabilize epitopes (such as the Φ epitope) within the RSV F protein such that the epitopes can be recognized by particular antibodies, elicit production of antibodies, and/or activate B cell receptors upon antibody binding.

In some embodiments targeted cross-linking can be used. A targeted cross-link is one that can be made to form at a particular position or positions within the RSV F protein or protein complex. Several strategies may be used to target cross-links to specific locations in an RSV F protein or polypeptide, such as the specific locations described herein. The present invention provides residue pairs within the RSV F protein that, when cross-linked, can or may stabilize a RSV F polypeptide, protein, or protein complex in its pre-F conformation, and/or in a conformation that is capable of binding to, or eliciting the production of, neutralizing antibodies, and/or that is capable of generating a neutralizing antibody response in an animal. A targeted cross-link may be introduced at one or more of the locations or positions specified herein by exploiting the physical and/or chemical properties of certain amino acid side chains, for example by making use of enzymatic reactions that recognize specific amino acid sequences or three-dimensional structures, or by incorporating non-natural amino acids that have the ability to form cross-links in a folded protein or protein complex.

Cross-links or modifications may be targeted to specific sites in the structure of the RSV F protein or polypeptide in order to achieve the desired outcome, e.g. stabilization or the pre-F conformation. The present invention contemplates the targeted introduction of one or more cross-links and/or other stabilizing modifications at any suitable position(s) in a RSV F protein or polypeptide, preferably where the cross-link or modification stabilizes the RSV F protein or polypeptide in a pre-fusion conformation, or provides enhanced stabilization of the pre-fusion conformation. The invention contemplates that any RSV F protein amino acid residue, residue pair, secondary structure or other region described herein for di-tyrosine cross-linking may also be used in the formation of other targeted cross-links or bonds or other modifications, including but not limited to amino acid positions Y33, K77, N88, M97, A147, S150, S155, H159, N183, V185, V187, Y198, V220, E222, F223, K226, S255, Y286, K427 and V469, or any combination thereof; residue pairs 147/286, 198/220, 198/222, 198/223, 198/226, 33/496, 77/222, 88/255, 97/159, 183/427, 185/427, and 187/427, or any combination thereof; regions or secondary structures including the F1 mobile N-terminus (residues 137-216), α2 (residues 148-160), α3 (residues 163-173), β3 (residues 176-182), β4 (residues 186-195), α4 (residues 197-211), the F1 mobile C-terminus (residues 461-513), β22 (residues 464-471), α9 (residues 474-479), β23 (residues 486-491), and α10 (493-514); and other regions of RSV F protein including residues from about position 67 to about position 87, from about position 78 to about position 98, from about position 87 to about position 107, from about position 137 to about position 157, from about position 140 to about position 160, from about position 145 to about position 165, from about position 149 to about position 169, from about position 173 to about position 193, from about position 175 to about position 195, from about position 177 to about position 197, from about position 188 to about position 208, from about position 210 to about position 230, from about position 212 to about position 232, from about position 213 to about position 233, from about position 216 to about position 236, from about position 245 to about position 265, from about position 276 to about position 296, from about position 417 to about position 437, and from about position 459 to about position 479.

A wide variety of methods of cross-linking proteins intra- and inter-molecularly are known in the art, including those having cross-links with varying lengths of spacer arms, and those with and without fluorescent and functional groups for purification. Such methods include, but are not limited to, the use of heterobifunctional cross-linkers (e.g. succinimidyl acetylthioacetate (SATA), trans-4-(maleimidylmethyl) cyclohexane-1-carboxylate (SMCC), and succinimidyl 3-(2-pyridyldithio)propionate (SPDP)), homobifunctional cross-linkers (e.g. succinimidyl 3-(2-pyridyldithio)propionate), photoreactive cross-linkers (e.g. 4-azido-2,3,5,6-tetrafluorobenzoic acid, STP ester, sodium salt (ATFB STP ester), 4-azido-2,3,5,6-tetrafluorobenzoic acid, succinimidyl ester (ATFB, SE), 4-azido-2,3,5,6-tetrafluorobenzyl amine, hydrochloride, benzophenone-4-isothiocyanate, benzophenone-4-maleimide, 4-benzoylbenzoic acid, succinimidyl ester, N-((2-pyridyldithio)ethyl)-4-azidosalicylamide (PEAS; AET), thiol reactive cross-linkers (e.g. maleimides and iodoacetamides), amine reactive cross-linkers (e.g. glutaraldyde, bis(imido esters), bis(succinimidyl esters), diisocyanates and diacid chlorides). Because thiol groups are highly reactive and relatively rare in most proteins by comparison to amine groups, thiol-reactive cross-linking may be used in some embodiments. In cases where thiol groups are missing or not present at appropriate sites in the structures of RSV prefusion F protein, they can be introduced using one of several thiolation methods. For example, Succinimidyl trans-4-(maleimidylmethyl)cyclohexane-1-carboxylate can be used to introduce thiol-reactive groups at amine sites.

Several oxidative cross-links are known, such as disulfide bonds (which form spontaneously and are pH and redox sensitive), and di-tyrosine bonds (which are highly stable, and irreversible under physiological conditions).

In some embodiments the cross-links stabilize the tertiary structure of a RSV pre-fusion F protein. In some embodiments the cross-links stabilize the quaternary structure of a RSV pre-fusion F protein. In some embodiments the cross-links stabilize both the tertiary and quaternary structure of a RSV pre-fusion F protein.

In some embodiments a RSV F protein or polypeptide of the invention has cross-links that are thermostable. In some embodiments a RSV F protein or polypeptide of the invention has cross-links that are not toxic. In some embodiments a RSV F protein or polypeptide of the invention has cross-links that are targeted cross-links, or non-targeted cross-links, or reversible cross-links, or irreversible cross-links, or cross-links formed by use of homo-bifunctional cross-linking agents, or cross-links formed by use of hetero-bifunctional cross-linking agents, or cross-links formed by use of reagents that react with amine groups, or cross-links formed by use of reagents that react with thiol groups, or cross-links formed by use of reagents that are photoreactive, or cross-links formed between amino acid residues, or cross-links formed between mutated amino acid residues incorporated into the structure of the proteins or protein complexes, or oxidative cross-links, or di-tyrosine bonds, or glutaraldehyde cross-links, or any combination thereof. In some embodiments the RSV F protein or polypeptide of the invention does not have glutaraldehyde cross-links.

In some embodiments the RSV F protein or polypeptide of the invention does not have any artificially-introduced disulfide bonds, or if it does have such disulfide bonds, also has additional artificially-introduced cross-links. In some embodiments the RSV F protein or polypeptide of the invention does not have any artificially introduced disulfide bonds, but may have naturally occurring disulfide bonds. Disulfide bonds can be introduced artificially when cysteine side-chains are engineered by point mutation. Disulfide bonds are, however, known to be pH sensitive and to be dissolved under certain redox conditions, and the preventative and/or therapeutic utility of proteins and/or protein complexes engineered with disulfide cross-links, for example to be used as immunogens in vivo, may therefore be compromised. Furthermore, undesired disulfide bonds often form between proteins with free sulfhydryl groups that mediate aggregate formation (see, for example, Harris R J et al. 2004, Commercial manufacturing scale formulation and analytical characterization of therapeutic recombinant antibodies. Drug Dev Res 61 (3): 137-154; Costantino & Pikal (Eds.), 2004. Lyophilization of Biopharmaceuticals, editors Costantino & Pekal. Lyophilization of Biopharmaceuticals. Series: Biotechnology: Pharmaceutical Aspects II, see pages 453-454; Tracy et al., 2002, U.S. Pat. No. 6,465,425), which has also been reported as a problem with HIV gp120 and gp41 (Jeffs et al. 2004. Expression and characterization of recombinant oligomeric envelope glycoproteins derived from primary isolates of HIV-1.Vaccine 22:1032-1046; Schulke et al., 2002. Oligomeric and conformational properties of a proteolytically mature, disulfide-stabilized human immunodeficiency virus type 1 gp140 envelope glycoprotein. J Virol 76:7760-7776). Thus, in many embodiments it is preferred that disulfide bonding is not used, or is not used as the sole method of cross-linking.

If the structure and/or immunogenicity of the RSV prefusion F protein is compromised or altered by a cross-link, maintaining its overall structure and function can be achieved by controlling the availability of amino acid side-chains for the cross-linking reaction or by introducing additional cross-links or other stabilizing modifications. For example, in the case of DT cross-linking, tyrosyl side-chains that are available for reaction, but that lead to the distortion of the structure of the complex, and that compromise the immunogenicity/antigenicity of the RSV F protein, can be removed by mutating such residues to another amino acid such as, for example, phenylalanine. Furthermore, point mutations may be introduced at positions where the amino acid side-chains will react with cross-linking agents or each other, such that the formation of the bond(s) causes the most beneficial outcome. These positions may also be identified as described herein.

When at a selected residue a reactive side-chain is not already present, a point mutation may be introduced, for example using molecular biological methods to introduce such a point mutation into the cDNA of a nucleic acid directing its expression, such that a reactive side-chain is present and available for the reaction.

Cross-links that may be used include, but are not limited to, reversible cross-links resulting from the use of homo- and hetero-bifunctional cross-linking agents that react with amine and/or thiol groups, photoreactive cross-link reagents, any cross-links that may form between non-classical amino acids incorporated into the structure of a protein or protein complex, any oxidative cross-links, such as, but not limited to, di-tyrosine cross-links/bonds, heterobifunctional cross-linkers (e.g. succinimidyl acetylthioacetate (SATA), trans-4-(maleimidylmethyl) cyclohexane-1-carboxylate (SMCC), and succinimidyl 3-(2-pyridyldithio)propionate (SPDP)), homobifunctional cross-linkers (e.g. succinimidyl 3-(2-pyridyldithio)propionate), photoreactive cross- linkers (e.g. 4-azido-2,3,5,6-tetrafluorobenzoic acid, STP ester, sodium salt (ATFB, STP ester), 4-azido-2,3,5,6-tetrafluorobenzoic acid, succinimidyl ester (ATFB, SE), 4-azido-2,3,5,6-tetrafluorobenzyl amine, hydrochloride, benzophenone-4-isothiocyanate, benzophenone-4-maleimide, 4-benzoylbenzoic acid, succinimidyl ester, N-((2-pyridyldithio)ethyl)-4-azidosalicylamide (PEAS; AET), thiol reactive cross-linkers (e.g. maleimides and iodoacetamides), amine reactive cross-linkers (e.g. glutaraldyde, bis(imido esters), bis(succinimidyl esters), diisocyanates and diacid chlorides).

The present invention also contemplates the introduction of targeted non-covalent tyrosine-stacking interactions as "cross-links" to stabilize protein-protein interactions and/or desired protein or peptide conformations, such as the pre-fusion conformation of RSV F protein. The cross-link comprises a targeted pi stacking interaction including but not limited to a T-shaped, sandwich, or parallel displaced pi stacking interaction between the aromatic side chains of an introduced/engineered tyrosine and an endogenous tyrosine, phenylalanine, histidine, or tryptophan within the protein or protein complex, or between the aromatic side chain of an introduced/engineered tyrosine and a second introduced/engineered tyrosine within the protein or protein complex.

Irreversible cross-links, as used in the context of this application, include those that are not significantly dissolved under physiologically relevant conditions. It is preferred that the type of cross-links used should not lead to aggregate formation during expression or when the RSV F polypeptides, proteins and/or protein complexes of the invention are stored at high concentrations. Disulfide bonds are not irreversible cross-links. Rather they are reversible cross-links and may dissolve under physiologically relevant conditions and/or lead to aggregate formation during protein expression and/or production or when stored in high concentrations.

In some embodiments cross-links may be targeted to the specific regions of RSV F polypeptides, proteins and/or protein complexes described herein in order to achieve the desired conformational stabilization and/or the desired immunogenic properties (e.g. the ability to maintain the pre-F conformation and/or to bind to broadly neutralizing antibodies). Alternatively, proteins with the cross-links at the locations specified herein may be isolated from a mixture of cross-linked and un-cross-linked proteins with and without desired modifications, for example based on chemical, physical, and/or functional characteristics. Such characteristics may include, for example, trimerization, the presence of the pre-F conformation, and/or any desired antigenic, immunogenic, or biochemical characteristics.

Alternatively, in some embodiments, cross-links may not be targeted, and proteins with the desired cross-links or properties may be isolated from a mixture of modified and unmodified proteins made using a non-targeted cross-linking system.

In embodiments where RSV F polypeptides, proteins or protein complexes with the desired cross-links are to be isolated from a mixture of cross-linked and un-cross-linked proteins, such isolation or separation may be performed on the basis of one or more characteristics including, but not limited to, molecular weight, molecular volume, chromatographic properties, mobility in electrophoresis, antigenic and biochemical characteristics, fluorescence characteristics, solubility, binding to antibodies, structural characteristics, immunological characteristics, or any other suitable characteristics.

In addition to the specific cross-linking positions described herein, additional positions within RSV F polypeptides, proteins or protein complexes can be identified at which further cross-links can be made, for example where a reactive side-chain would be able to form a bond with a reactive side-chain elsewhere on the RSV F protein/complex. In some embodiments, such additional positions can be selected, for example, to maintain or improve the immunogenicity/antigenicity of the protein, polypeptide or protein complex. In some embodiments, such additional positions to be cross-linked can be selected in pairs.

Di-tyrosine (DT) Cross-Linking

In some embodiments the present invention provides RSV F polypeptides, proteins and/or protein complexes that comprise di-tyrosine (DT) cross-links, and methods of making such DT-cross-linked RSV F polypeptides, proteins and/or protein complexes.

Di-tyrosine cross-linking introduces one or more covalent carbon-carbon bonds into proteins or protein complexes. This provides a method for stabilizing proteins, protein complexes, and conformations, by introduction of intra- and/or inter-polypeptide di-tyrosine bonds while maintaining their structural and functional integrity (See Marshall et al., U.S. Pat. Nos. 7,037,894 & 7,445,912, the contents of which are hereby incorporated by reference). The minimally altering, and zero-length DT cross-link is not hydrolyzed under physiological conditions, and has been demonstrated to maintain proteins' structural integrity by liquid chromatography/mass spectrometry (LC/MS). Di-tyrosine cross-links are known to be safe, as they form naturally in vivo, both in the context of proteins evolved to utilize their specific characteristics (e.g. Elvin C M et al. 2005, Nature 437:999-1002; Tenovuo J & Paunio K 1979, Arch Oral Biol.; 24(8):591-4), and as a consequence of non-specific protein oxidation (Giulivi et al. 2003, Amino Acids 25(3-4):227-32), and as they are present in large quantities in some of our most common foods: DT bonds form the structure of wheat gluten—the quarternary protein structure comprising the glutenin subunits—e.g. in bread dough during mixing and baking (Tilley et al. 2001, Agric. Food Chem 49, 2627). Di-tyrosine bonds do not form spontaneously in vitro. Rather, the enzymatic cross-link reaction is carried out under optimized conditions to preserve protein structure and function. Therefore, non-specific bonding/aggregation does not occur (unlike with disulfide bonding), and therefore large-scale manufacturing of a DT stabilized immunogen may be economically more feasible.

Tyrosyl side-chains are present in many redox enzymes, and catalysis of the enzyme-specific reactions often involves tyrosyl radicals that are long-lived and have comparatively low reactivity. Under optimized conditions radical formation is specific to tyrosyl side-chains. In close proximity, tyrosyl side chains undergo radical coupling and form a covalent, carbon-carbon bond. Tyrosyl radicals that do not react revert to non-radicalized tyrosyl side-chains (Malencik & Anderson, 2003. Di-tyrosine as a product of oxidative stress and fluorescent probe. Amino Acids 25: 233-247). Therefore, tyrosyl side-chains must be situated in close proximity to form DT bonds, either within a single folded polypeptide chain, or on closely interacting protein domains within a complex. Because a Cα-Cα separation of approximately 5-8 Å is a prerequisite to bond formation (Brown et al., 1998. Determining protein-protein interactions by oxidative cross-linking of a glycine-glycine-histidine fusion protein. Biochemistry 37, 4397-4406; Marshall et al. 2006, U.S. Pat. No. 7,037,894), and because no atom is added in the formation of these bonds, the resulting "staple" is "zero length" and non-disruptive to the protein structure.

Tyrosines residues to be cross-linked may be naturally present in the primary structure of the protein to be cross-linked or may be added by controlled point mutation. To form DT bonds, proteins with tyrosyl side chains can be subjected to reaction conditions that lead to the formation of DT bonds. Such conditions are, or become, oxidative reaction conditions, as the DT bond formation reaction is an oxidative cross-linking reaction. In some embodiments the DT cross-linking reaction conditions yield proteins that are otherwise not, or not detectably, modified. Such conditions may be obtained by use of enzymes that catalyze the formation of $H_2O_2$, such as peroxidases. DT bond formation may be monitored by spectrophotometry with an excitation wavelength of around 320 nm, and fluorescence measured at a wavelength of around 400 nm (see, for example, FIG. 34), while loss of tyrosyl fluorescence is monitored also monitored by standard procedures. When loss of tyrosyl florescence is no longer stoichiometric with DT bond formation, the reaction may be stopped by any methods known to one skilled in the art, such as, for example, by the addition of a reducing agent and subsequent cooling (on ice) or freezing of the sample. Further details of how to perform DT cross-linking are known in the art and are described in, for example, Marshall et al. 2006, U.S. Pat. No. 7,037,894, the contents of which are hereby incorporated by reference.

The major advantages of di-tyrosine cross-linking in protein engineering include (i) the ability to target specific residues for cross-linking (based on the primary, secondary, tertiary, and/or quaternary structures of proteins and complexes), (ii) minimal structural modification, (iii) specificity of the reaction (tyrosine is the only amino acid known to form cross-links under specific cross-linking conditions); (iv) stability of the linkage, (v) zero length of the cross-link (no atom is added), and (vi) the scalability of the cross-linking chemistry.

In some embodiments, targeted DT cross-links may be introduced at one or more of the specific locations in the RSV F protein that are recited herein. In other embodiments, additional positions within RSV F polypeptides, proteins or protein complexes can be identified at which DT cross-links can be made. In some embodiments, di-tyrosine bonds or cross-links are targeted to specific residue pairs within the structure of a RSV F protein or polypeptide where DT bonds will, or are expected to, form due to, for example, their close proximity. In some embodiments tyrosyl side chains are already present at amino acid residues to be cross-linked. In some cases naturally occurring tyrosine residues may constitute either one or both of the paired tyrosine residues necessary for di-tyrosine bond formation. However, in other cases the RSV F polypeptides, proteins and/or protein complexes of the invention are mutated or engineered to add one or more tyrosine residues, or to substitute one or more non-tyrosine residues for tyrosine residues. Such mutations are referred to herein as "to-tyrosine" mutations, and can be introduced at locations where it is desirable to form di-tyrosine cross-links/bonds. In some embodiments, the present invention provides mutant RSV F polypeptides, proteins, and/or protein complexes in which tyrosyl side chains are introduced at desired cross-linking positions by introducing point mutations to tyrosine in a nucleic acid sequence encoding the RSV F polypeptide, protein, or protein complex. Alternatively, in some embodiments RSV proteins, polypeptides or protein complexes, or portions thereof, may be synthesized to include tyrosine residues or amino acids having tyrosyl side chains at desired cross-linking positions. Conversely, in some embodiments the present invention provides mutant RSV F polypeptides, proteins, and/or protein complexes in which tyrosyl side chains are removed at undesirable cross-linking positions by introducing point mutations from tyrosine in a nucleic acid sequence encoding the RSV F polypeptide, protein, or protein complex, or RSV F polypeptides, proteins, or protein complexes may be synthesized to exclude tyrosine residues or amino acids having tyrosyl side chains at positions where cross-linking is not desired. For example, at least one of the tyrosyl side chains can be replaced with another side chain, such as a phenylalanine side chain (see, for example, Marshall CP et al., US patent application Ser. No. 09/837,235, the contents of which are hereby incorporated by reference). Accordingly, the RSV F polypeptides, proteins and protein complexes of the invention may comprise point mutations "to tyrosine" or "from tyrosine." Such mutations can be made by altering the nucleic acid sequences that encode the RSV F polypeptides, proteins and/or protein complexes of the invention using any suitable mutagenesis methods known in the art. Alternatively, mutant RSV F polypeptides, proteins and/or protein complexes may be synthesized, purified, and/or produced by any other suitable methods known in the art.

In some embodiments, the present invention contemplates the targeted introduction of one or more di-tyrosine cross-link at any suitable position(s) in a RSV F polypeptide, protein or protein complex where the cross-link will or may stabilize the RSV F polypeptide, protein or protein complex in its pre-fusion conformation. Such stabilization may be achieved, for example, by introducing cross-links that stabilize interactions between or within RSV F protein F1 and F2 polypeptides and/or by introducing cross-links that stabilize the interactions between or within RSV F protein protomers. In some embodiments, the F1 polypeptide of a RSV F protein is cross-linked with the F2 polypeptide of the same protomer (inter-molecular/intra-protomer bond). In some embodiments, the F1 polypeptide is intra-molecularly cross-linked (e.g., both tyrosines of the cross-link are located within the same F1 polypeptide). In some embodiments, the F2 polypeptide is intra-molecularly cross-linked (e.g., both tyrosines of the cross-link are located within the same F1 polypeptide). In some embodiments, the F1 polypeptide of the RSV prefusion F protein is cross-linked with the F1 polypeptide of an adjacent protomer (inter-protomer bond). In some embodiments, the F1 polypeptide of the RSV prefusion F protein is cross-linked with the F2 polypeptide of an adjacent protomer (inter-protomer bond).

Making and Analyzing RSV F Polypeptides, Proteins, and Protein Complexes

In some embodiments the present invention provides methods for making the RSV F polypeptides, proteins, and protein complexes of the invention. The RSV F polypeptides, proteins, and protein complexes of the invention can be made by any suitable means known in the art. In some embodiments the RSV F polypeptides, proteins, and/or protein complexes of the invention can be made by recombinant means. In some embodiments, the RSV F polypeptides, proteins, and/or protein complexes of the invention, or any portion thereof, can be made by chemical synthesis means. For example, a peptide corresponding to a portion of a protein or protein complex as described herein can be synthesized by use of a peptide synthesizer.

Recombinant Production Methods

In embodiments where the RSV F polypeptides, proteins and protein complexes of the invention are made by recombinant means, nucleic acids encoding the RSV F polypeptides, proteins and protein complexes of the invention can be expressed in any suitable cell type, including, but not limited to mammalian cells and insect cells (such as SF9 or Hi5 cells, using a baculovirus expression system). Methods for expressing polypeptides and proteins from nucleic acid molecules are routine and well known in the art, and any suitable methods, vectors, systems, and cell types known in the art can be used. For example, typically nucleic acid sequences encoding the RSV F polypeptides, proteins and/or protein complexes of the invention will be placed into a suitable expression construct containing a suitable promoter, which will then be delivered to cells for expression.

Chimeric/Fusion Proteins & Oligomerization Domains

In some embodiments it may be desirable to add chimeric domains to the RSV F polypeptides, proteins and/or protein complexes described herein, to produce chimeric proteins/fusion proteins, for example to facilitate the analysis and/or isolation and/or purification of the RSV F polypeptides, proteins and/or protein complexes described herein. In some embodiments, the RSV F polypeptides, proteins and protein complexes of the invention may comprise leader sequences, precursor polypeptide sequences, secretion signals, localization signals, epitope tags, and the like. Epitope tags that can be used include, but are not limited to, FLAG tags, glutathione S-transferase (GST) tags, green fluorescent protein (GFP) tags, hemagglutinin A (HA) tags, histidine (His) tags, luciferase tags, maltose-binding protein (MBP) tags, c-Myc tags, protein A tags, protein G tags, streptavidin (strep) tags, and the like.

In some embodiments it may be desirable to add oligomerization domains to facilitate the assembly of RSV F polypeptides, proteins and/or protein complexes as described herein, and/or to facilitate stabilization of the pre-F conformation, and/or to stabilize other structural features of the RSV F polypeptides, proteins and/or protein complexes. In some embodiments the oligomerization domains are trimerization motifs, including, but not limited to, the T4 foldon motif. There are a wide variety of trimerization domains in natural proteins that can be used for these purposes including, but not limited to, those described in Habazettl et al., 2009 (Habazettl et al., 2009. NMR Structure of a Monomeric Intermediate on the Evolutionarily Optimized Assembly Pathway of a Small Trimerization Domain. J.Mol.Biol. pp. null), Kammerer et al., 2005. (Kammerer et al., 2005. A conserved trimerization motif controls the topology of short coiled coils. Proc Natl Acad Sci USA 102 (39): 13891-13896), Innamorati et al., 2006. (Innamorati et al., 2006. An intracellular role for the C1 σ-globular domain. Cell signal 18(6): 761-770), and Schelling et al., 2007 (Schelling et al., 2007. The reovirus σ-1 aspartic acid sandwich : A trimerization motif poised for conformational change. Biol Chem 282(15): 11582-11589). Stabilizing trimeric protein complexes can also be accomplished using the GCN4 and T4 fibrinitin motifs (Pancera et al., 2005. Soluble Mimetics of Human Immunodeficiency Virus Type 1 Viral Spikes Produced by Replacement of the Native Trimerization Domain with a Heterologous Trimerization Motif: Characterization and Ligand Binding Analysis. J Virol 79(15): 9954-9969; Guthe et al., 2004. Very fast folding and association of a trimerization domain from bacteriophage T4 fibritin. J. Mol. Biol. v337 pp. 905-15; Papanikolopoulou et al., 2008. Creation of hybrid nanorods from sequences of natural trimeric fibrous proteins using the fibritin trimerization motif. Methods Mol Biol 474:15-33). Heterologous oligomerization motifs may be introduced by any recombinant methods known to one of ordinary skill in the art in order to stabilize the protein-protein interactions of the proteins of the present invention.

Chimeric RSV F polypeptides, proteins and/or protein complexes can be made by any method known to one of ordinary skill in the art, and may comprise, for example, one or several RSV F polypeptides, proteins and/or protein complexes of the invention, and/or any fragment, derivative, or analog thereof (for example, consisting of at least a domain of a polypeptide, protein, or protein complex of the invention, or at least 6, and preferably at least 10 amino acids of thereof) joined at its amino- or carboxy-terminus via a peptide bond to an amino acid sequence of another protein or other protein domain or motif. In some embodiments such chimeric proteins can be produced by any method known to one of ordinary skill in the art, including, but not limited to, recombinant expression of a nucleic acid encoding a chimeric protein (e.g. comprising a first coding sequence joined in-frame to a second coding sequence); ligating the appropriate nucleic acid sequences encoding the desired amino acid sequences to each other in the proper coding frame, and expressing the chimeric product.

Post Translational Modifications

In some embodiments, the RSV F polypeptides, proteins and protein complexes described herein may be altered by adding or removing post-translational modifications, by adding or removing chemical modifications or appendices, and/or by introducing any other modifications known to those of ordinary skill in the art. Included within the scope of the invention are RSV F polypeptides, proteins and protein complexes that are modified during or after translation or synthesis, for example, by glycosylation (or deglycosylation), acetylation (or deacetylation), phosphorylation (or dephosphorylation), amidation (or deamidization), pegylation, derivatization by known protecting/blocking groups, proteolytic cleavage, or buy any other means known in the art. For example, in some embodiments the RSV F polypeptides, proteins and/or protein complexes may be subjected to chemical cleavage by cyanogen bromide, trypsin, chymotrypsin, papain, V8 protease, NaBH4, acetylation, formylation, oxidation, reduction, metabolic synthesis in the presence of tunicamycin, etc. In some embodiments such posttranslational modifications can be used to render the RSV F polypeptides, proteins, and/or protein complexes of the present invention more immunogenic, more stable, and/or more capable of binding to, or eliciting the production of, neutralizing and broadly neutralizing antibodies.

Obtaining RSV F in its Pre-F Conformation

In some embodiments the RSV F polypeptides and/or proteins of the invention are assembled into protein complexes having a desired conformational structure, such as the pre-F conformation, and are cross-linked in order to stabilize that conformation. As described elsewhere in the present application, the pre-F conformation of the RSV F protein comprises a trimer formed from three protomers. In some embodiments, prior to and/or during the enzymatic cross-linking reaction, the RSV F protein may be obtained in (and/or maintained in) the pre-F conformation, for example while cross-linking is performed. In some embodiments the RSV F protein may be produced and/or isolated in such a way that most, or substantially all, of the RSV F molecules are present in the pre-F conformation. In some embodiments RSV F molecules in the pre-F conformation may be separated from a mixed population of RSV F protein molecules comprising some that are in the pre-F conformation and some that are in other conformations. In some embodiments, the RSV F protein is expressed in cells (for example as its membrane bound or soluble form) and spontaneously assembles into its normal pre-F conformation. In some embodiments no additional stabilization may be necessary to retain the RSV F protein in its pre-F form. In some embodiments the expressed and assembled/folded RSV F protein may be kept under particular conditions, or in particular compositions, that favor formation and/or maintenance of the pre-F conformation. For example, in some embodiments the RSV prefusion F protein may be maintained in the absence of cells—contact with which might otherwise trigger a switch to the post-F conformation. The RSV prefusion F protein may be obtained and/or isolated and/or maintained in the pre-F conformation using any suitable method known in the art, including, but not limited to, standard protein purification methods, such as ion exchange chromatography, size exclusion chromatography, and/or affinity chromatography methods. In some embodimemts the RSV prefusion F protein may be expressed in the presence of, co-expressed with, or contacted with, molecules that bind to the RSV F protein and stabilize it in its pre-F conformation, including, but not limited to, antibodies, small molecules, peptides, and/or peptidomimetics. Non-limiting examples of antibodies that bind to the pre-fusion RSV F protein include the 5C4, AM22, and D25 antibodies (see McLellan et al. (2013) Science 342:592-598, which is hereby incorporated by reference in its entirety). In some embodiments, the RSV F protein may be obtained, isolated, or maintained in its pre-F conformation by controlling the ionic strength of the media/buffer in which the protein is present (such as by using high or low ionic strength media). In some embodiments the RSV F protein may be obtained, isolated, or maintained at one or more temperatures that favor preservation of the pre-F conformation. In some embodiments the RSV F protein may be obtained, isolated, or maintained over a period of time that diminishes the degree to which the pre-F conformation lost.

In some embodiments analysis may be performed to confirm that the desired conformation, such as the pre-F conformation, has been formed and/or maintained in the RSV F protein. Such analysis may be performed prior to cross-linking, during the cross-linking process, after the cross-linking process, or at any combination of such stages. Such analysis may comprise any suitable methods known in the art for assessing the 3-dimensional structure of a protein or protein complex, including functional analysis, crystallographic analysis, and the like. In some embodiments such analysis may include assessing binding of the RSV protein to certain antibodies, such as those that are specific to the pre-F conformation and/or those that are known to bind to the Ø site, as described elsewhere herein, including, but not limited to the 5C4, AM22, and D25 antibodies.

Protein Purification

In some embodiments the methods for making RSV F polypeptides, proteins, and protein complexes of the invention may comprise purifying the RSV F polypeptides, proteins, or protein complexes before, during, or after, one or more steps in the manufacturing process. For example, in some embodiments the RSV F polypeptides, proteins, and/or protein complexes of the invention may be purified after completion of all of the manufacturing steps. In some embodiments the RSV F polypeptides, proteins, and/or protein complexes of the invention may be purified before commencing the cross-linking process or after one or more of the intermediate method steps in the process, for example, after expression of an RSV F polypeptide or protein, after assembly of a protein complex, after obtaining the RSV F protein in its pre-F conformation, or during or after performing a cross-linking reaction. The RSV F polypeptides, proteins, and/or protein complexes of the invention may be isolated or purified using any suitable method known in the art. Such methods include, but are not limited to, chromatography (e.g. ion exchange, affinity, and/or sizing column chromatography), ammonium sulfate precipitation, centrifugation, differential solubility, or by any other technique for the purification of proteins known to one of ordinary skill in the art. In specific embodiments it may be necessary to separate the desirable influenza RSV F polypeptides, proteins, and/or protein complexes of the invention from those that were not sufficiently cross-linked, or those in which the pre-F conformation was not sufficiently stabilized. This can be done using any suitable system known in the art. For example, RSV proteins in the pre-F conformation can be separated from those that are not in the pre-F conformation using antibody-based separation methods using pre-F or post-F specific antibodies. The RSV F polypeptides, proteins, and/or protein complexes of the invention may be purified from any source used to produce them. For example, the RSV F polypeptides, proteins, and/or protein complexes of the invention may be purified from sources including insect, prokaryotic, eukaryotic, mono-cellular, multi-cellular, animal, plant, fungus, vertebrate, mammalian, human, porcine, bovine, feline, equine, canine, avian, or tissue culture cells, or any other source. The degree of purity may vary, but in various embodiments, the purified RSV F polypeptides, proteins, and/or protein complexes of the invention are provided in a form in which is they comprise more than about 10%, 20%, 50%, 70%, 75%, 80%, 85%, 90%, 95%, 98%, 99%, or 99.9% of the total protein in the final composition. In some embodiments the RSV F polypeptides, proteins, and/or protein complexes of the invention may be isolated and purified from other proteins, or any other undesirable products (such as non-cross-linked or non-pre-F RSV F), by standard methods including, but not limited to, chromatography, glycerol gradients, affinity chromatography, centrifugation, ion exchange chromatography, size exclusion chromatography, and affinity chromatography, or by any other standard technique for the purification of proteins known in the art. The RSV F polypeptides, proteins, and/or protein complexes to be isolated may be expressed in high or low ionic media, or isolated in high or low ionic buffers or solutions. The RSV F polypeptides, proteins, and/or protein complexes of the invention may also be isolated at one or more temperatures that favor preservation of the desired conformation. They may also be isolated over a period of time that diminishes the degree to which a preparation would have lost the desired conformation. The degree to which a preparation of proteins retains one or more desired conformations (such as the pre-F conformation and/or conformations that favor binding to neutralizing antibodies., or the desired properties) may be assayed by any suitable method known in the art, including, for example, but not limited to, biochemical, biophysical, immunologic, and virologic analyses. Such assays include, for example, but are not limited to, immunoprecipation, enzyme-linked immunosorbent assays (ELISAs), or enzyme-linked immunosorbent spot (ELISPOT) assays, crystallographic analysis (including co-crystallization with antibodies), sedimentation, analytical ultracentrifugation, dynamic light scattering (DLS), electron microscopy (EM), cryo-EM tomography, calorimetry, surface plasmon resonance (SPR), fluorescence resonance energy transfer (FRET), circular dichroism analysis, and small angle x-ray scattering, neutralization assays, antibody-dependent cellular cytotoxicity assays, and/or virologic challenge studies in vivo.

The yield of the RSV F polypeptides, proteins, and/or protein complexes of the invention can be determined by any means known in the art, for example, by comparing the amount of the final engineered proteins (such as cross-linked pre-F RSV) as compared to the amount of the starting material, or as compared to the amount of the materials present in any preceding step of the production methods. Protein concentrations can determined by standard procedures, such as, for example, Bradford or Lowrie protein assays. The Bradford assay is compatible with reducing agents and denaturing agents (Bradford, M, 1976. Anal. Biochem. 72: 248). The Lowry assay has better compatibility with detergents and the reaction is more linear with respect to protein concentrations and read-out (Lowry, O J, 1951. Biol. Chem. 193: 265).

Exemplary Production Methods

In some embodiments the present invention provides a method for producing a RSV F protein stabilized in its pre-fusion conformation, the method comprising: (a) obtaining an RSV F protein in its pre-F conformation, (b) identifying one or more regions in the tertiary and/or quaternary structure of the RSV prefusion F protein in which the introduction of one or more cross-links could stabilize the pre-F conformation, and (c) introducing into the RSV prefusion F protein one or more cross-links at one or more of the regions identified in step (b) to form an engineered RSV F protein locked in its pre-fusion conformation. In some embodiments, the regions identified in step (b) comprise one or more of the specific regions or specific amino acid residues described herein. In some embodiments the cross-links are targeted cross-links. In some embodiments the cross-links are targeted DT cross-links. In some embodiments the cross-links are stable under physiological conditions. In some embodiments, the engineered RSV F protein stabilized in its pre-fusion conformation is useful as a vaccine immunogen. In some embodiments, the engineered RSV F protein locked in its pre-fusion conformation has one or more of the following properties: (i) enhanced ability bind to a neutralizing antibody as compared to the RSV F protein not so engineered (i.e. as compared to the RSV F protein without or before introduction of the cross-links), (ii) enhanced ability bind to a broadly neutralizing antibody as compared to the RSV F protein not so engineered, (iii) enhanced ability bind to and activate B cell receptors as compared to the RSV F protein not so engineered, (iv) enhanced ability to elicit an antibody response in an animal as compared to the RSV F protein not so engineered, (v) enhanced ability to elicit a protective antibody response in an animal as compared to the RSV F protein not so engineered, (vi) enhanced ability to elicit production of neutralizing antibodies in an animal as compared to the RSV F protein not so engineered, (vii) enhanced ability to elicit production of broadly neutralizing antibodies in an animal as compared to the RSV F protein not so engineered, (viii) enhanced ability to elicit a protective immune response in an animal as compared to the RSV F protein not so engineered, and (ix) enhanced ability to bind to and elicit production of antibodies that recognize quaternary neutralizing epitopes in an animal as compared to the RSV F protein not so engineered. In some embodiments the methods for producing an RSV F protein stabilized in its pre-fusion conformation described herein also comprise performing an assay to determine if the engineered RSV F protein stabilized in its pre-fusion conformation and/or has one or more of the properties listed above.

Properties of RSV F Polypeptides, Proteins and/or Protein Complexes

In some embodiments, the RSV F polypeptides, proteins and/or protein complexes of the invention, including in particular those that are cross-linked as described herein, have certain structural, physical, functional, and/or biological properties. Such properties may include one or more of the following, or any combination of the following: existence of the pre-F conformation, stability of the RSV pre-F conformation; Improved stability of the RSV pre-F conformation (as compared to non-cross-linked RSV F proteins); Improved half-life of the RSV pre-F conformation (as compared to non-cross-linked RSV F proteins); Improved thermostability (as compared to non-cross-linked RSV F proteins); Prolonged shelf-life (as compared to non-cross-linked RSV F proteins); Prolonged half-life inside the body of a subject (as compared to non-cross-linked RSV F proteins); Ability to be stored in solution without forming aggregates (including when present at a high concentration in solution); Reduced aggregation in solution (as compared to non-cross-linked RSV F proteins); Binding to an antibody; Binding to a neutralizing antibody; Binding to a broadly neutralizing antibody; Binding to a pre-F-specific antibody; Binding to an antibody that recognizes site 0; Binding to a conformationally-specific antibody; Binding to an antibody that recognizes a metastable epitope; Binding to an antibody selected from the group consisting of D25, AM22 and 5C4 (which antibodies are described in McLellan et al., 2013, Science, 340, p. 1113; Kwakkenbos et al., 2010, Nature Medicine, 16, p. 123; Spits & Beaumont, U.S. patent application Ser. No. 12/600,950; Beaumont, Bakker & Yasuda, U.S. patent application Ser. No. 12/898,325, the contents of each of which are hereby incorporated by reference in their entireties); Binding to palivizumab (Synagis); Binding to the neutralizing antibody 101F; Binding to a B cell receptor; Activation of a B Cell receptor; Eliciting an antibody response in an animal; Eliciting a protective antibody response in an animal; Eliciting production of neutralizing antibodies in an animal; Eliciting production of broadly neutralizing antibodies in an animal; Eliciting production of antibodies that recognize quaternary neutralizing epitopes (QNEs) in an animal; Eliciting a protective immune response in an animal; and/or Eliciting a humoral immune response in an animal. In the case of binding to antibody molecules, in some embodiments the RSV F polypeptides, proteins, and/or protein complexes of the invention bind to the antibodies (such as pre-F-specific antibodies, antibodies that bind to site 0, and/or D25, AM22 or 5C4) with high specificity and/or with high affinity.

Assays for Properties

In some embodiments the RSV F polypeptides, proteins, and/or protein complexes of the invention, or any intermediates in their manufacture, may be analyzed to confirm that they have desired properties, such as the desired structural, physical, functional, and/or biological properties—such as those properties listed above or identified elsewhere in this patent specification. For example, in some embodiments in vitro or in vivo assays can be performed to assess the RSV F protein's conformational structure, stability (e.g. thermostability), half-life (e.g. inside the body of a subject), aggregation in solution, binding to an antibody (such as a neutralizing antibody, broadly neutralizing antibody; pre-F-specific antibody; antibody that recognizes site 0, conformationally-specific antibody, antibody that recognizes a metastable epitope, D25, AM22, 5C4, 101F or palivizumab), binding to a B cell receptor, activation of a B Cell receptor, antigenicity, immunogenicity, ability to elicit an antibody response, ability to elicit a protective antibody/immune response, ability to elicit production of neutralizing antibodies, or ability to elicit a production of broadly neutralizing antibodies. In embodiments where the RSV F polypeptides, proteins, and/or protein complexes of the invention are tested in an animal in vivo, the animal may be any suitable animal species, including, but not limited to a mammal (such as a rodent species (e.g. a mouse or rat), a rabbit, a ferret, a porcine species, a bovine species, an equine species, an ovine species, or a primate species (e.g. a human or a non-human primate), or an avian species (such as a chicken).

Assays for assessing a protein's conformational structure are well known in the art and any suitable assay can be used, including, but not limited to, crystallographic analysis (e.g. X-ray crystallography or electron crystallography), sedimentation analysis, analytical ultracentrifugation, electron microscopy (EM), cryo-electron microscopy (cryo-EM), cryo-EM tomography, nuclear magnetic resonance (NMR), small angle x-ray scattering, fluorescence resonance energy transfer (FRET) assays, and the like.

Assays for assessing a protein's stability are well known in the art and any suitable assay can be used, including, but not limited to, denaturing and non-denaturing electrophoresis, isothermal titration calorimetry, and time-course experiments in which proteins are incubated and analyzed over time at varying protein concentrations, temperatures, pHs or redox conditions. Proteins may also be analyzed for susceptibility to proteolytic degradation.

Assays for assessing binding of proteins to antibodies are well known in the art, and any suitable assay can be used, including, but not limited to, immunoprecipation assays, enzyme-linked immunosorbent assays (ELISAs), enzyme-linked immunosorbent spot assays (ELISPOTs), crystallographic assays (including co-crystallization with antibodies), surface plasmon resonance (SPR) assays, fluorescence resonance energy transfer (FRET) assays, and the like.

Assays for assessing neutralization activity are well known in the art, and any suitable assay can be used. For example, assays can be performed to determine the neutralizing activity of antibodies or antisera generated by vaccination/immunization of animals with the RSV F polypeptides, proteins, and/or protein complexes of the invention. Neutralization assays known in the art include, but are not limited to, those described by Dey et al. 2007 (Dey et al., 2007, Characterization of Human Immunodeficiency Virus Type 1 Monomeric and Trimeric gp120 Glycoproteins Stabilized in the CD4-Bound State: Antigenicity, Biophysics, and Immunogenicity. J Virol 81(11): 5579-5593) and Beddows et al., 2006 (Beddows et al., 2007, A comparative immunogenicity study in rabbits of disulfide-stabilized proteolytically cleaved, soluble trimeric human immunodeficiency virus type 1 gp140, trimeric cleavage-defective gp140 and momomeric gp120. Virol 360: 329-340).

Assays for assessing whether a vaccine immunogen is capable of eliciting an immune response and/or proving protective immunity are well known in the art, and any suitable assay can be used. For example, assays can be performed to determine whether vaccination/immunization of animals with the RSV F polypeptides, proteins, and/or protein complexes of the invention provide an immune response and/or protective immunity against infection with RSV. In some embodiments comparisons may be made between placebo and test vaccinated groups with regard to their rates of infection or sero-conversion or viral loads.

Assays for assessing a protein's pharmacokinetics and bio-distribution are also well known in the art, and any

Compositions

In some embodiments the present invention provides compositions comprising any of the RSV F polypeptides, proteins, and/or protein complexes described herein. In some embodiments such compositions may be immunogenic compositions, vaccine compositions and/or therapeutic compositions. In some embodiments, such compositions may be administered to subjects.

In some embodiments the RSV F polypeptides, proteins, and/or protein complexes of the invention may be provided in a composition that comprises one or more additional active components, such as one or more additional vaccine immunogens or therapeutic agents. In some embodiments the RSV F polypeptides, proteins, and/or protein complexes of the invention may be provided in a composition that comprises one or more other components, including, but not limited to, pharmaceutically acceptable carriers, adjuvants, wetting or emulsifying agents, pH buffering agents, preservatives, and/or any other components suitable for the intended use of the compositions. Such compositions can take the form of solutions, suspensions, emulsions and the like. The term "pharmaceutically acceptable carrier" includes various diluents, excipients and/or vehicles in which, or with which, the RSV F polypeptides, proteins, and/or protein complexes of the invention can be provided. The term "pharmaceutically acceptable carrier" includes, but is not limited to, carriers known to be safe for delivery to human and/or other animal subjects, and/or approved by a regulatory agency of the Federal or a state government, and/or listed in the U.S. Pharmacopeia, and/or other generally recognized pharmacopeia, and/or receiving specific or individual approval from one or more generally recognized regulatory agencies for use in humans and/or other animals. Such pharmaceutically acceptable carriers, include, but are not limited to, water, aqueous solutions (such as saline solutions, buffers, and the like), organic solvents (such as certain alcohols and oils, including those of petroleum, animal, vegetable or synthetic origin, such as peanut oil, soybean oil, mineral oil, sesame oil), and the like. In some embodiments the compositions of the invention also comprise one or more adjuvants. Exemplary adjuvants include, but are not limited to, inorganic or organic adjuvants, oil-based adjuvants, virosomes, liposomes, lipopolysaccharide (LPS), molecular cages for antigens (such as immune-stimulating complexes ("ISCOMS")), Ag-modified saponin/cholesterol micelles that form stable cage-like structures that are transported to the draining lymph nodes), components of bacterial cell walls, endocytosed nucleic acids (such as double-stranded RNA (dsRNA), single-stranded DNA (ssDNA), and unmethylated CpG dinucleotide-containing DNA), AUM, aluminum phosphate, aluminum hydroxide, and Squalene. In some embodiments virosomes are used as the adjuvant. Additional commercially available adjuvants that can be used in accordance with the present invention include, but are not limited to, the Ribi Adjuvant System (RAS, an oil-in-water emulsion containing detoxified endotoxin (MPL) and mycobacterial cell wall components in 2% squalene (Sigma M6536)), TiterMax (a stable, metabolizable water-in-oil adjuvant (CytRx Corporation 150 Technology Parkway Technology Park/Atlanta Norcross, Georgia 30092)), Syntex Adjuvant Formulation (SAF, an oil-in-water emulsion stabilized by Tween 80 and pluronic polyoxyethelene/polyoxypropylene block copolymer L121 (Chiron Corporation, Emeryville, Calif.)), Freund's Complete Adjuvant, Freund's Incomplete Adjuvant, ALUM—aluminum hydroxide, Al(OH)3 (available as Alhydrogel, Accurate Chemical & Scientific Co, Westbury, N.Y.), SuperCarrier (Syntex Research 3401 Hillview Ave. P.O. Box 10850 Palo Alto, Calif. 94303), Elvax 40W1,2(an ethylene-vinyl acetate copolymer (DuPont Chemical Co. Wilmington, Del.)), L-tyrosine co-precipitated with the antigen (available from numerous chemical companies); Montanide (a manideoleate, ISA Seppic Fairfield, N.J.)), AdjuPrime (a carbohydrate polymer), Nitrocellulose-absorbed protein, Gerbu adjuvant (C-C Biotech, Poway, Calif.), and the like.

In some embodiments the compositions of the invention comprise an "effective amount" of a RSV F polypeptide, protein, and/or protein complex of the invention. An "effective amount" is an amount required to achieve a desired end result. Examples of desired end results include, but are not limited to, the generation of a humoral immune response, the generation of a neutralizing antibody response, the generation of a broadly neutralizing antibody response, and the generation of protective immunity. The amount of a RSV F polypeptide, protein, and/or protein complex of the invention that is effective to achieve the desired end result will depend on variety of factors including, but not limited to, the type, subtype, and strain of the RSV virus against which protection or some other therapeutic effect is sought, the species of the intended subject (e.g. whether a human or some other animal species), the age and/or sex of the intended subject, the planned route of administration, the planned dosing regimen, the seriousness of any ongoing influenza infection (e.g. in the case of therapeutic uses), and the like. The effective amount—which may be a range of effective amounts—can be determined by standard techniques without any undue experimentation, for example using in vitro assays and/or in vivo assays in the intended subject species or any suitable animal model species. Suitable assays include, but are not limited to, those that involve extrapolation from dose-response curves and/or other data derived from in vitro and/or in vivo model systems. In some embodiments the effective amount may be determined according to the judgment of a medical or veterinary practitioner based on the specific circumstances.

Uses of the RSV F Polypeptides, Proteins & Protein Complexes of the Invention In some embodiments, the RSV F polypeptides, proteins, and protein complexes of the invention may be useful as research tools, as diagnostic tools, as therapeutic agents, as targets for the production of antibody reagents or therapeutic antibodies, and/or as vaccines or components of vaccine compositions. For example, in some embodiments the RSV F polypeptides, proteins, and protein complexes of the invention are useful as a vaccine immunogens in animal subjects, such as mammalian subject, including humans. These and other uses of the RSV F polypeptides, proteins, and protein complexes of the invention are described more fully below. Those of skill in the art will appreciate that the RSV F polypeptides, proteins, and protein complexes of the invention may be useful for a variety of other applications also, and all such applications and uses are intended to fall within the scope of this invention.

Tools for Studying RSV F Antibodies

In one embodiment, the RSV F polypeptides, proteins, and protein complexes of the invention may be useful as analytes for assaying and/or measuring binding of, and/or titers of, anti-RSV F antibodies, for example in ELISA assays, Biacore/SPR binding assays, and/or any other assays for antibody binding known in the art. For example, the RSV F polypeptides, proteins, and protein complexes of the invention could be used to analyze, and/or compare the efficacy of anti-RSV F antibodies.

Tools for Generation of Antibodies

The RSV F polypeptides, proteins, and protein complexes of the invention may also be useful for the generation of therapeutic antibodies and/or antibodies that can be used as research tools or for any other desired use. For example, the RSV F polypeptides, proteins, and protein complexes of the invention can be used for immunizations to obtain antibodies to the RSV F protein for use as research tools and/or as therapeutics. In some embodiments the RSV F polypeptides, proteins, and protein complexes of the invention can be used to immunize a non-human animal, such as a vertebrate, including, but not limited to, a mouse, rat, guinea pig, rabbit, goat, non-human primate, etc. in order to generate antibodies. Such antibodies, which may be monoclonal or polyclonal, and/or cells that produce such antibodies, can then be obtained from the animal. For example, in some embodiments RSV F polypeptides, proteins, and protein complexes of the invention may be used to immunize a mouse and to produce and obtain monoclonal antibodies, and/or hybridomas that produce such monoclonal antibodies. Such methods can be carried out using standard methods known in the art for the production of mouse monoclonal antibodies, including standard methods for hybridoma production. In some embodiments RSV F polypeptides, proteins, and protein complexes of the invention may be used for the production of a chimeric (e.g. part-human), humanized, or fully-human antibody, for example using any of the methods currently known in the art for production of chimeric, humanized and fully human antibodies, including, but not limited to, CDR grafting methods, phage-display methods, transgenic mouse methods (e.g. using a mouse that has been genetically altered to allow for the production of fully human antibodies, such as the Xenomouse) and/or any other suitable method known in the art. Antibodies to the RSV F polypeptides, proteins, and protein complexes of the invention made using such systems can be characterized antigenically using one or a set of several antigens, preferably including the RSV F polypeptides, proteins, and protein complexes of the invention themselves. Additional characterization of such antibodies may be carried out by any standard methods known to one of ordinary skill in the art, including, but not limited to, ELISA-based methods, SPR-based methods, biochemical methods (such as, but not limited to, iso-electric point determination), and methods known in the art for studying biodistribution, safety, and efficacy of antibodies—for example in preclinical and clinical studies.

Administration to Subjects

In some embodiments, the present invention provides methods that comprise administering the RSV F polypeptides, proteins and/or protein complexes of the invention (or compositions comprising such RSV F polypeptides, proteins and/or protein complexes) to subjects. Such methods may comprise methods for treating individuals having RSV (i.e. therapeutic methods) and/or methods for protecting individuals against future RSV infection (i.e. prophylactic methods).

Subjects to which the RSV F polypeptides, proteins and/or protein complexes of the invention, or compositions comprising such RSV F polypeptides, proteins and/or protein complexes, can be administered (for example in the course of a method of treatment or a method of vaccination) include any and all animal species, including, in particular, those that are susceptible to RSV infection or that can provide model animal systems for the study of RSV infection. In some embodiments, the subjects are mammalian species. In some embodiments, the subjects are avian species. Mammalian subjects include, but are not limited to, humans, non-human primates, rodents, rabbits, and ferrets. Avian subjects include, but are not limited to chickens, such as those on poultry farms. In some embodiments the subjects to which the RSV F polypeptides, proteins and/or protein complexes of the invention, or compositions comprising such RSV F polypeptides, proteins and/or protein complexes are cadministered, either have RSV, or are at risk of RSV infection. In some embodiments, the subjects are immunocompromised. In some embodiments, the subjects have a heart disease or disorder. In some embodiments, the subject is a human of greater than about 50 years in age, greater than about 55 years in age, greater than about 60 years in age, greater than about 65 years in age, greater than about 70 years in age, greater than about 75 years in age, greater than about 80 years in age, greater than about 85 years in age, or greater than about 90 years in age. In some embodiments, the subject is a human of less than about 1 month in age, less than about 2 months in age, less than about 3 months in age, less than about 4 months in age, less than about 5 months in age, less than about 6 months in age, less than about 7 months in age, less than about 8 months in age, less than about 9 months in age, less than about 10 months in age, less than about 11 months in age, less than about 12 months in age, less than about 13 months in age, less than about 14 months in age, less than about 15 months in age, less than about 16 months in age, less than about 17 months in age, less than about 18 months in age, less than about 19 months in age, less than about 20 months in age, less than about 21 months in age, less than about 22 months in age, less than about 23 months in age, or less than about 24 months in age.

Various delivery systems are known in the art and any suitable delivery systems can be used to administer the compositions of the present invention to subjects. Such delivery systems include, but are not limited to, intradermal, intramuscular, intraperitoneal, intravenous, subcutaneous, intranasal, epidural, and oral delivery systems. The compositions of the present invention may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. Pulmonary administration can also be employed, e.g., by use of an inhaler or nebulizer, and formulation with an aerosolizing agent.

In some embodiments it may be desirable to administer the pharmaceutical compositions of the invention locally to a tissue in which the RSV F protein or polypeptide may be most effective in generating a desirable outcome. This may be achieved by, for example, local infusion, injection, delivery using a catheter, or by means of an implant, such as a porous, non-porous, or gelatinous implant or an implant comprising one or more membranes (such as sialastic membranes) or fibers from or through which the protein or protein complexes may be released locally. In some embodiments a controlled release system may be used. In some embodiments a pump may be used (see Langer, supra; Sefton, 1987. CRC Crit. Ref. Biomed. Eng. 14: 201; Buchwald et al., 1980. Surgery 88: 507; Saudek et al., 1989. N. Engl. J. Med. 321: 574). In some embodiments polymeric materials may be used to facilitate and/or control release of the RSV prefusion F protein of the invention (see Medical Applications of Controlled Release, Langer and Wise (eds.), 1974. CRC Pres., Boca Raton, Fla.; Controlled Drug Bioavailability, 1984. Drug Product Design and Performance, Smolen and Ball (eds.), Wiley, N.Y.; Ranger & Peppas, 1983 Macromol. Sci. Rev. Macromol. Chem. 23: 61; see also Levy etal., 1985. Science 228:190; During etal, 1989. Ann. Neurol. 25: 351; Howard etal., 1989. J. Neurosurg 71:105). In some embodiments a controlled release system can be placed in proximity to the tissue/organ to which the RSV prefusion F protein or polypeptide is to be delivered (see, e.g., Goodson, 1984. Medical Applications of Controlled Release, supra, vol. 2: 115-138). Some suitable controlled release systems that may be used in conjunction with the present invention are described Langer, 1990, Science; vol. 249: pp. 527-1533

In some embodiments, administration of the compositions of the invention can be performed in conjunction with administration of one or more immunostimulatory agents. Non-limiting examples of such immunostimulatory agents include various cytokines, lymphokines and chemokines with immunostimulatory, immunopotentiating, and pro-inflammatory activities, such as interleukins (e.g., IL-1, IL-2, IL-3, IL-4, IL-12, IL-13); growth factors (e.g., granulocyte-macrophage (GM)-colony stimulating factor (CSF)); and other immunostimulatory agents, such as macrophage inflammatory factor, Flt3 ligand, B7.1; B7.2. The immunostimulatory agents can be administered in the same formulation as the RSV F protein or polypeptide, or can be administered separately.

In some embodiments, the RSV F polypeptides, proteins, and/or protein complexes of the invention, or compositions comprising them, can be administered to subjects in a variety of different RSV vaccination methods or regimens. In some such embodiments, administration of a single dose is preferred. However, in other embodiments, additional dosages can be administered, by the same or different route, to achieve the desired prophylactic effect. In neonates and infants, for example, multiple administrations may be required to elicit sufficient levels of immunity. Administration can continue at intervals throughout childhood, as necessary to maintain sufficient levels of protection against RSV infection. Similarly, adults who are particularly susceptible to RSV infection, such as, for example, the elderly and immunocompromised individuals, may require multiple immunizations to establish and/or maintain protective immune responses. Levels of induced immunity can be monitored, for example, by measuring amounts of neutralizing secretory and serum antibodies, and dosages adjusted or vaccinations repeated as necessary to elicit and maintain desired levels of protection.

In some embodiments, dosing regimens may comprise a single administration/immunization. In other embodiments, dosing regimens may comprise multiple administrations/immunizations. For example, vaccines may be given as a primary immunization followed by one or more boosters. In some embodiments of the present invention such a "prime-boost" vaccination regimen may be used. For example, in some such prime-boost regimens a composition comprising a RSV F polypeptide, protein or protein complex as described herein may be administered to an individual on multiple occasions (such as two, three, or even more occasions) separated in time, with the first administration being the "priming" administration and subsequent administrations being "booster" administrations. In other such prime-boost regimens a composition comprising a RSV F polypeptide, protein or protein complex as described herein may be administered to an individual after first administering to the individual a composition comprising a viral or DNA vector encoding an RSV polypeptide, protein or protein complex as a "priming" administration, with one or more subsequent "booster" administrations of a composition comprising a RSV F polypeptide, protein or protein complex as described herein. Boosters may be delivered via the same and/or different route as the primary immunization. Boosters are generally administered after a time period after the primary immunization or the previously administered booster. For example, a booster can be given about two weeks or more after a primary immunization, and/or a second booster can be given about two weeks or more after the first boosters. Boosters may be given repeatedly at time periods, for example, about two weeks or greater throughout up through the entirety of a subject's life. Boosters may be spaced, for example, about two weeks, about three weeks, about four weeks, about one month, about two months, about three months, about four months, about five months, about six months, about seven months, about eight months, about nine months, about ten months, about eleven months, about one year, about one and a half years, about two years, about two and a half years, about three years, about three and a half years, about four years, about four and a half years, about five years, or more after a primary immunization or after a previous booster.

Preferred unit dosage formulations are those containing a dose or unit (e.g. an effective amount), or an appropriate fraction thereof, of the RSV F polypeptides, proteins, and/or protein complexes of the invention. In addition to such ingredients, formulations of the present invention may include other agents commonly used by one of ordinary skill in the art. Pharmaceutical compositions provided by the invention may be conveniently presented in preferred unit dosage formulations prepared using conventional pharmaceutical techniques. Such techniques include the step of bringing into association the active ingredient and the pharmaceutical carrier(s) or excipient(s) or other ingredients. In general, the formulations are prepared by uniformly and intimately bringing into association the active ingredient with liquid carriers. Formulations suitable for parenteral administration include aqueous and non-aqueous sterile injection solutions which may contain anti-oxidants, buffers, bacteriostats and solutes which render the formulation isotonic with the blood of the intended recipient, and aqueous and non-aqueous sterile suspensions which may include suspending agents and thickening agents. The formulations may be presented in unit-dose or multi-dose containers, for example, sealed ampoules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets commonly used by one of ordinary skill in the art.

Kits

The present invention further provides kits comprising RSV polypeptides, proteins or protein complexes of the invention, or compositions containing such polypeptides, proteins or protein complexes. To facilitate use of the methods and compositions of the invention, any of the components and/or compositions described herein, and additional components useful for experimental or therapeutic or vaccine purposes, can be packaged in the form of a kit. Typically, the kit contains, in addition to the above components, additional materials which can include, e.g., instructions for using the components, packaging material, a container, and/or a delivery device.

Various embodiments of the present invention may also be further described by the following non-limiting examples:

EXAMPLE

RSV F protein variants E222Y (SEQ ID NO:13), K226Y (SEQ ID NO:15), V469Y (SEQ ID NO:16), N88Y/S255Y (SEQ ID NO:18), V185Y/K427Y (SEQ ID NO:20) were expressed in human cells as modified by the introduction of di-tyrosine bonds as described below.

Figure 33:
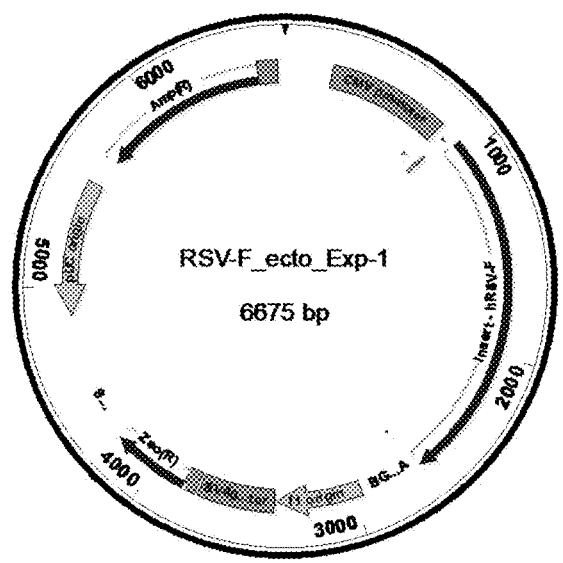
FIG. 33. Illustrative nucleic acid construct for expression of RSV F protein in mammalian cells.

Expression Plasmids. cDNA encoding a C-terminal fusion of the WT human RSV-F ectodomain or DS-Cav1protein ectodomain to the T4 fibritin foldon trimerization motif, thrombin cleavage-site, 6× HIS-tag (SEQ ID NO: 46), and strep-tag were codon-optimized for human expression and synthesized (Geneart). cDNA encoding RSV F protein variants E222Y (SEQ ID NO:13), K226Y (SEQ ID NO:15), V469Y (SEQ ID NO:16), N88Y/S255Y (SEQ ID NO:18), V185Y/K427Y (SEQ ID NO:20) were also synthesized. These DNA sequences were cloned into the pCDNA3.1/zeo+ expression vector (Invitrogen) via 5' BamHI and 3'XhoI restriction endonuclease sites using standard methods (FIG. 33).

Cells and Transfections. HEK 293 cells (ATCC) were grown in Dulbecco's Modification of Eagle's Medium (DMEM, Invitrogen) supplemented with 10% Fetal Bovine Serum and 50 µg/ml gentamycin. Cells were seeded into 6-well tissue culture plates (Corning) and grown till 80% confluent (~24 h). Cells were transfected with 2 µg of each RSV-F expression plasmid per well using a 1:4 ratio (M/V) of DNA to polyethylenimine (25 kDa, linear). 16 h post-transfection, media was removed and replaced with 2 ml/well of serum-free Freestyle-293 expression media (Invitrogen). Cells were cultured at 37 degrees C. for an additional 48 h-72 h in 5% $CO_2$ prior to collection and analysis.

Figures 35A, 35B:
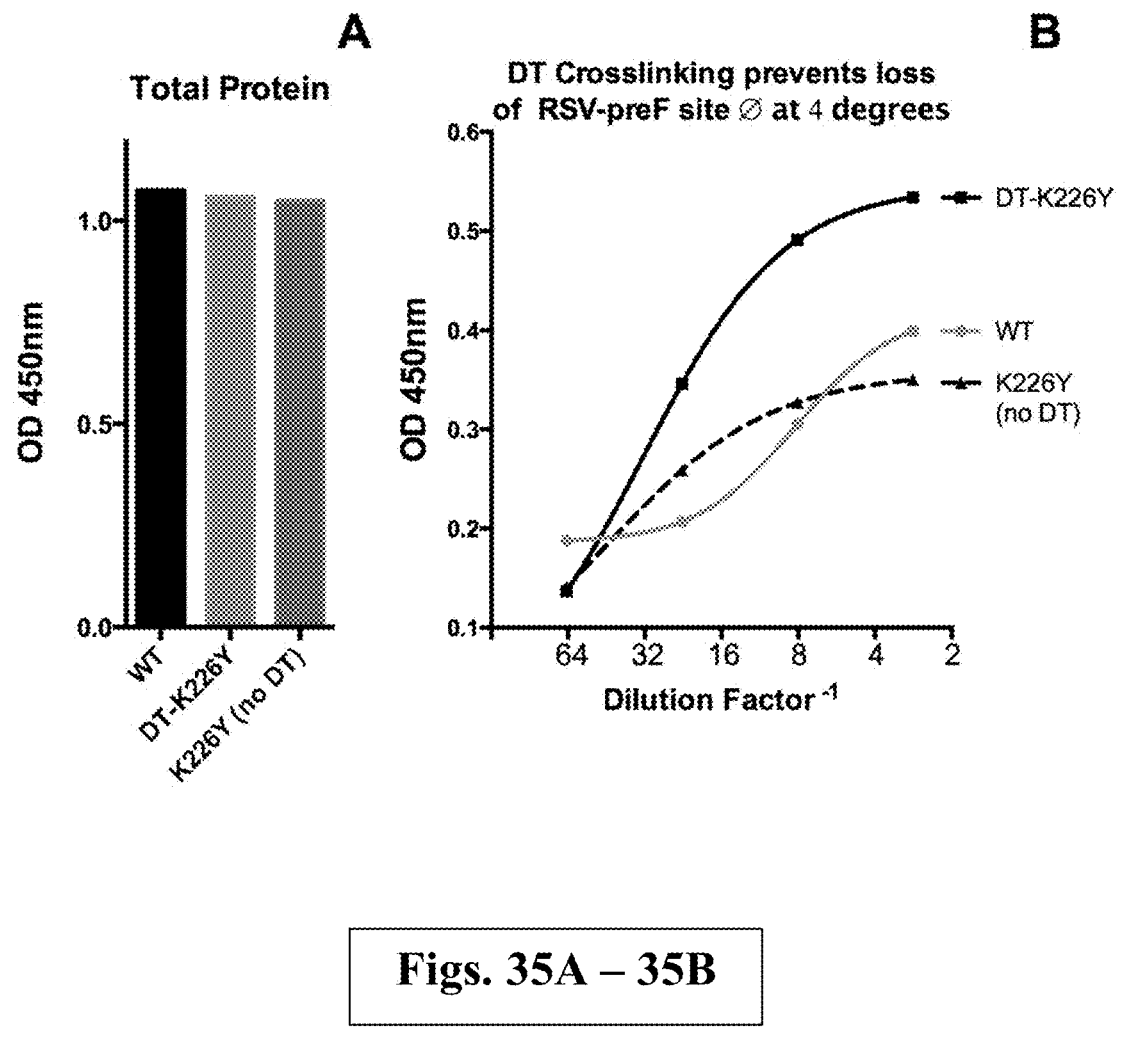

Detection of RSV-F in Cell Supernatants by ELISA. After collection, total RSV-F protein was directly captured from cell supernatants for 1 h at room temperature in EIA/RIA high-bind 96-well plates (Corning). Protein-containing and control wells were subsequently blocked with 4% nonfat milk in PBS-tween20 (0.05%) for 1 h at room temperature. Plates were washed 3× with PBS-T (400 µl/well). Total RSV-F was detected for 1 h using a high-affinity human anti-hRSV antibody (100 ng/ml in PBS) that recognizes both pre- and post-fusion forms of RSV-F. Prefusion F was detected using a pre-F specific human monoclonal antibody (2 µg/ml in PBS) that recognizes site Ø. Wells were again washed 3× in PBS-T followed by a 1 h room temperature incubation with an HRP-conjugated goat anti-human $F(ab)_2$ (Jackson Immunoresearch) at a 1:5000 dilution in PBS. Wells were washed 6× with PBS-T and total RSV-F was detected and quantified using 100 µl A 3,3',5,5'-tetramethylbenzidine (TMB) to produce a colorimetric signal. The colorimetric reaction was stopped by the addition of equal volume 4N sulfuric acid. Final Optical Density readings were taking at 450 nm using a BioRad Benchmark Plus microplate absorbance spectrophotometer. A 2× serial dilution series for each supernatant was used to determine the linear range of detectable signal for each sample allowing accurate comparison of the relative amount of RSV-F between samples (FIG. 35).

Figure 34:
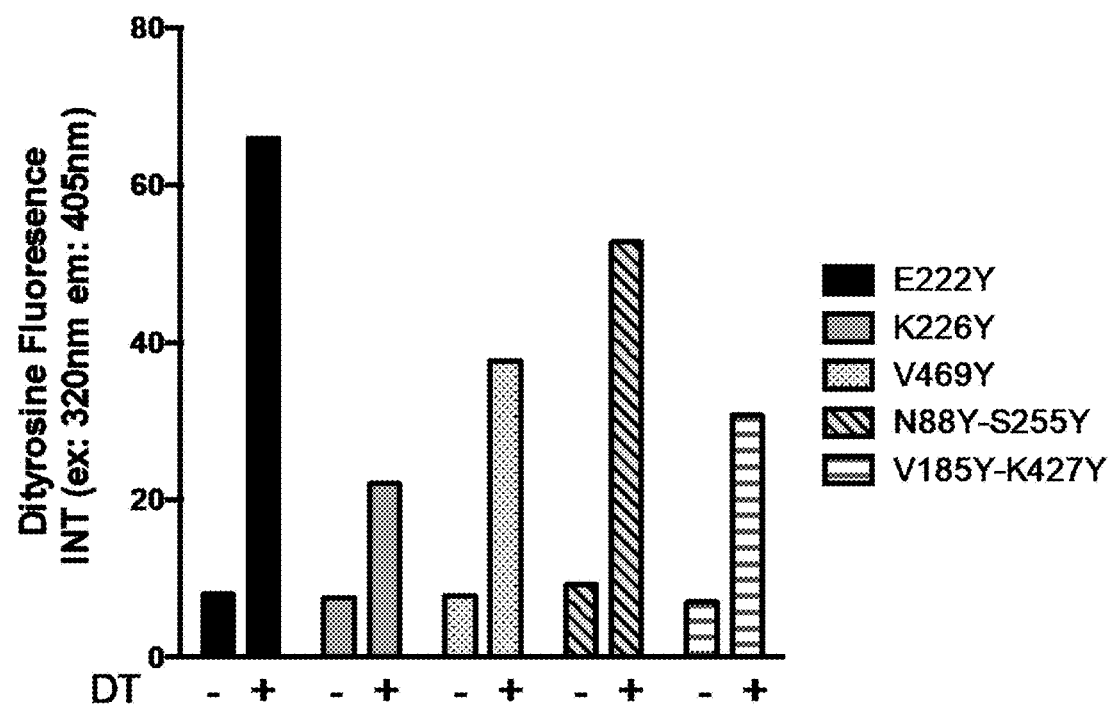
FIG. 34. Targeted di-tyrosine cross-linking of RSV F protein. HEK 293 cells were transfected with vectors expressing RSV-F variants that enabling $F_1$-$F_1$ intra-protomer DT-cross-links (E222Y (SEQ ID NO: 13) and K226Y (SEQ ID NO:15)), $F_1$-$F_1$ intra-protomer DT-cross-links (V469Y (SEQ ID NO:16) and N88Y-S255Y (SEQ ID NO:18)), or $F_1$-$F_1$ intermolecular DT-cross-links (V185Y-K427Y (SEQ ID NO:20)). Background-subtracted fluorescence intensity values are shown. (INT) intensity, (DT) di-tyrosine, (−) and (+) indicate before and after application of the di-tyrosine cross-linking technology, respectively.

Di-tyrosine-Cross-linking in Cell Supernatants. Immediately following collection, 100 µl of transfected and control cell supernatants were transferred to wells of black, flat-bottom, non-binding 96-well FIA plates (Greiner bio-one). 300 ng of *Arthromyces ramosus* peroxidase was added to each sample to be cross-linked. 1 µl of 1.2 mM $H_2O_2$ was then added to both control and DT reactions for a final reaction concentration of 120 µM $H_2O_2$. Reactions were allowed to proceed for 20 minutes at room temperature followed by alkalization of the reactions by addition of equal volume sodium phosphate buffer at pH 10. Di-tyrosine specific fluorescence was read at an excitation wavelength of 320 nm and emission wavelength of 405 nm using a Thermo Scientific Fluoroskan Ascent FL (FIG. 34).

72 h post transfection, supernatents were cross-linked (DT) or left uncross-linked and total protein was measured by ELISA using a high-affinity human anti-hRSV antibody (100 ng/ml in PBS) that recognizes both pre- and post-fusion forms of RSV-F. See FIG. 35A. Following storage at 4 degrees C. for 16 days presentation of site Ø was measured by ELISA using a preF specific human monoclonal antibody (2 µg/ml in PBS) that recognizes site Ø. Di-tyrosine cross-links were found to stabilize key epitope on RSV prefusion F protein. See FIG. 35B.

While the foregoing invention has been described in some detail for purposes of clarity and understanding, it will be clear to one skilled in the art from a reading of this disclosure that various changes in form and detail can be made without departing from the true scope of the invention. The invention may also be further defined in terms of the following claims.

The invention claimed is:

1. An RSV F polypeptide, protein or protein complex comprising:
    (a) a point mutation to tyrosine at amino acid position 226, or an amino acid position corresponding to position 226 as determined by alignment to, and using the amino acid numbering of, SEQ ID NO. 1,
    (b) one or more cavity-filling hydrophobic amino acid substitutions, and
    (c) a trimerization domain.

2. The RSV F polypeptide, protein or protein complex according to claim 1, wherein the trimerization domain is a foldon domain.

3. The RSV F polypeptide, protein or protein complex according to claim 1, further comprising a di-tyrosine cross-link between the tyrosine at amino acid position 226 and a tyrosine at amino acid position 198, or an amino acid position corresponding to position 198 as determined by alignment to, and using the amino acid numbering of, SEQ ID NO.1.

4. The RSV F polypeptide, protein or protein complex according to claim 2, further comprising a di-tyrosine cross-link between the tyrosine at amino acid position 226 and a tyrosine at amino acid position 198, or an amino acid position corresponding to position 198 as determined by alignment to, and using the amino acid numbering of, SEQ ID NO.1.

5. A nucleic acid molecule encoding an RSV F polypeptide, protein or protein complex according to claim 1.

6. A nucleic acid molecule encoding an RSV F polypeptide, protein or protein complex according to claim 2.

7. A nucleic acid molecule encoding an RSV F polypeptide, protein or protein complex according to claim 3.

8. A nucleic acid molecule encoding an RSV F polypeptide, protein or protein complex according to claim 4.

9. A composition comprising an RSV F polypeptide, protein or protein complex according to claim 1.

10. The composition of claim 9, further comprising an adjuvant.

11. A composition comprising an RSV F polypeptide, protein or protein complex according to claim 2.

12. The composition of claim 11, further comprising an adjuvant.

13. A composition comprising an RSV F polypeptide, protein or protein complex according to claim 3.

14. The composition of claim 13, further comprising an adjuvant.

15. A composition comprising an RSV F polypeptide, protein or protein complex according to claim 4.

16. The composition of claim 15, further comprising an adjuvant.

* * * * *

SEQUENCE LISTING

```
<160> NUMBER OF SEQ ID NOS: 47

<210> SEQ ID NO 1
<211> LENGTH: 568
<212> TYPE: PRT
<213> ORGANISM: Human respiratory syncytial virus

<400> SEQUENCE: 1

Met Glu Leu Leu Ile Leu Lys Ala Asn Ala Ile Thr Thr Ile Leu Thr
1               5                   10                  15
```

-continued

Ala Val Thr Phe Cys Phe Ala Ser Gly Gln Asn Ile Thr Glu Phe
            20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
            85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
            115                 120                 125

Leu Ser Lys Lys Arg Lys Arg Arg Phe Leu Gly Phe Leu Leu Gly Val
            130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
            165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
            195                 200                 205

Lys Gln Ser Cys Ser Ile Ser Asn Ile Glu Thr Val Ile Glu Phe Gln
210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
            245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
            275                 280                 285

Met Ser Ile Ile Lys Glu Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
            325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
            355                 360                 365

Thr Met Asn Ser Leu Thr Leu Pro Ser Glu Val Asn Leu Cys Asn Val
            370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp

```
                     435                 440                 445
Thr Val Ser Val Gly Asn Thr Leu Tyr Tyr Val Asn Lys Gln Glu Gly
            450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                    485                 490                 495

Glu Lys Ile Asn Gln Ser Leu Ala Phe Ile Arg Lys Ser Asp Glu Leu
                500                 505                 510

Leu Ser Ala Ile Gly Gly Tyr Ile Pro Glu Ala Pro Arg Asp Gly Gln
            515                 520                 525

Ala Tyr Val Arg Lys Asp Gly Glu Trp Val Leu Leu Ser Thr Phe Leu
        530                 535                 540

Gly Gly Leu Val Pro Arg Gly Ser His His His His His His Ser Ala
545                 550                 555                 560

Trp Ser His Pro Gln Phe Glu Lys
                565

<210> SEQ ID NO 2
<211> LENGTH: 574
<212> TYPE: PRT
<213> ORGANISM: Human respiratory syncytial virus

<400> SEQUENCE: 2

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240
```

-continued

```
Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Thr Gly Lys Ser Thr Thr Asn Ile Met Ile Thr
        515                 520                 525

Thr Ile Ile Ile Val Ile Ile Val Val Leu Leu Ser Leu Ile Ala Ile
    530                 535                 540

Gly Leu Leu Leu Tyr Cys Lys Ala Lys Asn Thr Pro Val Thr Leu Ser
545                 550                 555                 560

Lys Asp Gln Leu Ser Gly Ile Asn Asn Ile Ala Phe Ser Lys
                565                 570
```

<210> SEQ ID NO 3
<211> LENGTH: 568
<212> TYPE: PRT
<213> ORGANISM: Human respiratory syncytial virus

<400> SEQUENCE: 3

```
Met Glu Leu Leu Ile His Arg Ser Ser Ala Ile Phe Leu Thr Leu Ala
1               5                   10                  15

Ile Asn Ala Leu Tyr Leu Thr Ser Ser Gln Asn Ile Thr Glu Glu Phe
            20                  25                  30

Tyr Gln Ser Thr Cys Ser Ala Val Ser Arg Gly Tyr Phe Ser Ala Leu
        35                  40                  45
```

-continued

```
Arg Thr Gly Trp Tyr Thr Ser Val Ile Thr Ile Glu Leu Ser Asn Ile
    50                  55                  60

Thr Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110

Gln His Met Asn Tyr Thr Ile Asn Thr Thr Lys Asn Leu Asn Val Ser
        115                 120                 125

Ile Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asn Asn Gln Leu Leu Pro Ile Val Asn
        195                 200                 205

Gln Gln Ser Cys Arg Ile Phe Asn Ile Glu Thr Val Ile Glu Phe Gln
    210                 215                 220

Gln Lys Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
        355                 360                 365

Thr Met Asn Ser Leu Thr Leu Pro Ser Glu Val Ser Leu Cys Asn Thr
    370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Leu Glu Gly
    450                 455                 460
```

```
Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
            485                 490                 495

Glu Lys Ile Asn Gln Ser Leu Ala Phe Ile Arg Lys Ser Asp Glu Leu
        500                 505                 510

Leu Ser Ala Ile Gly Gly Tyr Ile Pro Glu Ala Pro Arg Asp Gly Gln
        515                 520                 525

Ala Tyr Val Arg Lys Asp Gly Glu Trp Val Leu Leu Ser Thr Phe Leu
    530                 535                 540

Gly Gly Leu Val Pro Arg Gly Ser His His His His His His Ser Ala
545                 550                 555                 560

Trp Ser His Pro Gln Phe Glu Lys
                565

<210> SEQ ID NO 4
<211> LENGTH: 574
<212> TYPE: PRT
<213> ORGANISM: Human respiratory syncytial virus

<400> SEQUENCE: 4

Met Gl

```
Leu Met Ser Ser Asn Val Gln Ile Val Arg Gln Ser Tyr Ser Ile
        275                 280                 285

Met Ser Ile Ile Lys Glu Glu Val Leu Ala Tyr Val Val Gln Leu Pro
    290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
        355                 360                 365

Thr Met Asn Ser Leu Thr Leu Pro Ser Glu Val Ser Leu Cys Asn Thr
    370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Leu Glu Gly
    450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Thr Gly Lys Ser Thr Thr Asn Ile Met Ile Thr
        515                 520                 525

Thr Ile Ile Ile Val Ile Ile Val Val Leu Leu Ser Leu Ile Ala Ile
    530                 535                 540

Gly Leu Leu Leu Tyr Cys Lys Ala Lys Asn Thr Pro Val Thr Leu Ser
545                 550                 555                 560

Lys Asp Gln Leu Ser Gly Ile Asn Asn Ile Ala Phe Ser Lys
                565                 570

<210> SEQ ID NO 5
<211> LENGTH: 568
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
```

```
            50                  55                  60
Lys Glu Asn Lys Cys Asn Gly Thr Asp Ala Lys Val Lys Leu Ile Lys
 65                  70                  75                  80

Gln Glu Leu Asp Lys Tyr Lys Asn Ala Val Thr Glu Leu Gln Leu Leu
                 85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
            115                 120                 125

Leu Ser Lys Lys Arg Lys Arg Arg Phe Leu Gly Phe Leu Leu Gly Val
        130                 135                 140

Gly Ser Ala Ile Ala Ser Gly Val Ala Val Cys Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Phe Lys Val
                180                 185                 190

Leu Asp Leu Lys Asn Tyr Ile Asp Lys Gln Leu Leu Pro Ile Leu Asn
        195                 200                 205

Lys Gln Ser Cys Ser Ile Ser Asn Ile Glu Thr Val Ile Glu Phe Gln
210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Cys Ile Ile Lys Glu Glu Val Leu Ala Tyr Val Val Gln Leu Pro
        290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
        450                 455                 460

Lys Ser Leu Tyr Val Lys Gly Glu Pro Ile Ile Asn Phe Tyr Asp Pro
465                 470                 475                 480
```

```
Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu Ser Ala Ile Gly Gly Tyr Ile Pro Glu Ala Pro Arg Asp Gly Gln
        515                 520                 525

Ala Tyr Val Arg Lys Asp Gly Glu Trp Val Leu Leu Ser Thr Phe Leu
    530                 535                 540

Gly Gly Leu Val Pro Arg Gly Ser His His His His His His Ser Ala
545                 550                 555                 560

Trp Ser His Pro Gln Phe Glu Lys
                565

<210> SEQ ID NO 6
<211> LENGTH: 574
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Cys Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Phe Lys Val
            180                 185                 190

Leu Asp Leu Lys Asn Tyr Ile Asp Lys Gln Leu Leu Pro Ile Leu Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
```

Leu Met Ser Asn Asn Val Gln Ile Val Arg Gln Gln Ser Tyr Ser Ile
            260                 265                 270

Met Cys Ile Ile Lys Glu Glu Val Leu Ala Tyr Val Val Gln Leu Pro
        275                 280                 285

Leu Tyr Gly Val Ile Asp Thr Pro Cys Trp Lys Leu His Thr Ser Pro
    290                 295                 300

Leu Cys Thr Thr Asn Thr Lys Glu Gly Ser Asn Ile Cys Leu Thr Arg
305                 310                 315                 320

Thr Asp Arg Gly Trp Tyr Cys Asp Asn Ala Gly Ser Val Ser Phe Phe
            325                 330                 335

Pro Gln Ala Glu Thr Cys Lys Val Gln Ser Asn Arg Val Phe Cys Asp
        340                 345                 350

Thr Met Asn Ser Leu Thr Leu Pro Ser Glu Val Asn Leu Cys Asn Val
    355                 360                 365

Asp Ile Phe Asn Pro Lys Tyr Asp Cys Lys Ile Met Thr Ser Lys Thr
370                 375                 380

Asp Val Ser Ser Ser Val Ile Thr Ser Leu Gly Ala Ile Val Ser Cys
            385                 390                 395                 400

Tyr Gly Lys Thr Lys Cys Thr Ala Ser Asn Lys Asn Arg Gly Ile Ile
        405                 410                 415

Lys Thr Phe Ser Asn Gly Cys Asp Tyr Val Ser Asn Lys Gly Val Asp
    420                 425                 430

Thr Val Ser Val Gly Asn Thr Leu Tyr Tyr Val Asn Lys Gln Glu Gly
435                 440                 445

Lys Ser Leu Tyr Val Lys Gly Glu Pro Ile Ile Asn Phe Tyr Asp Pro
            450                 455                 460

Leu Val Phe Pro Ser Asp Glu Phe Asp Ala Ser Ile Ser Gln Val Asn
465                 470                 475                 480

Glu Lys Ile Asn Gln Ser Leu Ala Phe Ile Arg Lys Ser Asp Glu Leu
        485                 490                 495

Leu His Asn Val Asn Thr Gly Lys Ser Thr Thr Asn Ile Met Ile Thr
    500                 505                 510

Thr Ile Ile Ile Val Ile Ile Val Val Leu Leu Ser Leu Ile Ala Ile
515                 520                 525

Gly Leu Leu Leu Tyr Cys Lys Ala Lys Asn Thr Pro Val Thr Leu Ser
            530                 535                 540

Lys Asp Gln Leu Ser Gly Ile Asn Asn Ile Ala Phe Ser Lys
545                 550                 555

<210> SEQ ID NO 7
<211> LENGTH: 568
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

```
Arg Thr Gly Trp Tyr Thr Ser Val Ile Thr Ile Glu Leu Ser Asn Ile
    50              55              60

Lys Glu Asn Lys Cys Asn Gly Thr Asp Ala Lys Val Lys Leu Ile Lys
65              70              75              80

Gln Glu Leu Asp Lys Tyr Lys Asn Ala Val Thr Glu Leu Gln Leu Leu
                85              90              95

Met Gln Ser Thr Pro Ala Thr Asn Asn Arg Ala Arg Arg Glu Leu Pro
            100             105             110

Arg Phe Met Asn Tyr Thr Leu Asn Asn Ala Lys Lys Thr Asn Val Thr
        115             120             125

Leu Ser Lys Lys Arg Lys Arg Arg Phe Leu Gly Phe Leu Leu Gly Val
    130             135             140

Gly Ser Ala Ile Ala Ser Gly Val Ala Val Ser Lys Val Leu His Leu
145             150             155             160

Glu Gly Glu Val Asn Lys Ile Lys Ser Ala Leu Leu Ser Thr Asn Lys
                165             170             175

Ala Val Val Ser Leu Ser Asn Gly Val Ser Val Leu Thr Phe Lys Val
            180             185             190

Leu Asp Leu Lys Asn Tyr Ile Asp Lys Gln Leu Leu Pro Ile Leu Asn
        195             200             205

Lys Gln Ser Cys Ser Ile Ser Asn Ile Glu Thr Val Ile Glu Phe Gln
    210             215             220

Gln Lys Asn Asn Arg Leu Leu Glu Ile Thr Arg Glu Phe Ser Val Asn
225             230             235             240

Ala Gly Val Thr Thr Pro Val Ser Thr Tyr Met Leu Thr Asn Ser Glu
                245             250             255

Leu Leu Ser Leu Ile Asn Asp Met Pro Ile Thr Asn Asp Gln Lys Lys
            260             265             270

Leu Met Ser Asn Asn Val Gln Ile Val Arg Gln Gln Ser Tyr Ser Ile
        275             280             285

Met Ser Ile Ile Lys Glu Glu Val Leu Ala Tyr Val Val Gln Leu Pro
    290             295             300

Leu Tyr Gly Val Ile Asp Thr Pro Cys Trp Lys Leu His Thr Ser Pro
305             310             315             320

Leu Cys Thr Thr Asn Thr Lys Glu Gly Ser Asn Ile Cys Leu Thr Arg
                325             330             335

Thr Asp Arg Gly Trp Tyr Cys Asp Asn Ala Gly Ser Val Ser Phe Phe
            340             345             350

Pro Gln Ala Glu Thr Cys Lys Val Gln Ser Asn Arg Val Phe Cys Asp
        355             360             365

Thr Met Asn Ser Leu Thr Leu Pro Ser Glu Val Asn Leu Cys Asn Val
    370             375             380

Asp Ile Phe Asn Pro Lys Tyr Asp Cys Lys Ile Met Thr Ser Lys Thr
385             390             395             400

Asp Val Ser Ser Ser Val Ile Thr Ser Leu Gly Ala Ile Val Ser Cys
                405             410             415

Tyr Gly Lys Thr Lys Cys Thr Ala Ser Asn Lys Asn Arg Gly Ile Ile
            420             425             430

Lys Thr Phe Ser Asn Gly Cys Asp Tyr Val Ser Asn Lys Gly Val Asp
        435             440             445

Thr Val Ser Val Gly Asn Thr Leu Tyr Val Asn Lys Gln Glu Gly
    450             455             460

Lys Ser Leu Tyr Val Lys Gly Glu Pro Ile Ile Asn Phe Tyr Asp Pro
```

```
                465                 470                 475                 480
Leu Val Phe Pro Ser Asp Glu Phe Asp Ala Ser Ile Ser Gln Val Asn
                    485                 490                 495

Glu Lys Ile Asn Gln Ser Leu Ala Phe Ile Arg Lys Ser Asp Glu Leu
                500                 505                 510

Leu Ser Ala Ile Gly Gly Tyr Ile Pro Glu Ala Pro Arg Asp Gly Gln
                515                 520                 525

Ala Tyr Val Arg Lys Asp Gly Glu Trp Val Leu Leu Ser Thr Phe Leu
            530                 535                 540

Gly Gly Leu Val Pro Arg Gly Ser His His His His His His Ser Ala
545                 550                 555                 560

Trp Ser His Pro Gln Phe Glu Lys
                565

<210> SEQ ID NO 8
<211> LENGTH: 574
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
        50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
                100                 105                 110

Arg Phe Met Asn Tyr Thr Leu Asn Asn Ala Lys Lys Thr Asn Val Thr
            115                 120                 125

Leu Ser Lys Lys Arg Lys Arg Arg Phe Leu Gly Phe Leu Leu Gly Val
        130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Phe Lys Val
                180                 185                 190

Leu Asp Leu Lys Asn Tyr Ile Asp Lys Gln Leu Leu Pro Ile Leu Asn
            195                 200                 205

Lys Gln Ser Cys Ser Ile Ser Asn Ile Glu Thr Val Ile Glu Phe Gln
        210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255
```

```
Leu Leu Ser Leu Ile Asn Asp Met Pro Ile Thr Asn Asp Gln Lys Lys
            260                 265                 270

Leu Met Ser Asn Asn Val Gln Ile Val Arg Gln Ser Tyr Ser Ile
        275                 280                 285

Met Ser Ile Ile Lys Glu Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Thr Gly Lys Ser Thr Thr Asn Ile Met Ile Thr
        515                 520                 525

Thr Ile Ile Ile Val Ile Ile Val Val Leu Leu Ser Leu Ile Ala Ile
530                 535                 540

Gly Leu Leu Leu Tyr Cys Lys Ala Lys Asn Thr Pro Val Thr Leu Ser
545                 550                 555                 560

Lys Asp Gln Leu Ser Gly Ile Asn Asn Ile Ala Phe Ser Lys
                565                 570

<210> SEQ ID NO 9
<211> LENGTH: 568
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45
```

```
Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Cys Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Cys Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460
```

-continued

```
Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu Ser Ala Ile Gly Gly Tyr Ile Pro Glu Ala Pro Arg Asp Gly Gln
            515                 520                 525

Ala Tyr Val Arg Lys Asp Gly Glu Trp Val Leu Leu Ser Thr Phe Leu
        530                 535                 540

Gly Gly Leu Val Pro Arg Gly Ser His His His His His His Ser Ala
545                 550                 555                 560

Trp Ser His Pro Gln Phe Glu Lys
                565

<210> SEQ ID NO 10
<211> LENGTH: 574
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Cys Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255
```

```
Leu Leu Ser Leu Ile Asn Asp Met Pro Ile Thr Asn Asp Gln Lys Lys
                260                 265                 270

Leu Met Ser Asn Asn Val Gln Ile Val Arg Gln Ser Tyr Ser Ile
            275                 280                 285

Met Cys Ile Ile Lys Glu Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
        450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Thr Gly Lys Ser Thr Thr Asn Ile Met Ile Thr
        515                 520                 525

Thr Ile Ile Ile Val Ile Ile Val Val Leu Leu Ser Leu Ile Ala Ile
530                 535                 540

Gly Leu Leu Leu Tyr Cys Lys Ala Lys Asn Thr Pro Val Thr Leu Ser
545                 550                 555                 560

Lys Asp Gln Leu Ser Gly Ile Asn Asn Ile Ala Phe Ser Lys
                565                 570

<210> SEQ ID NO 11
<211> LENGTH: 568
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
```

```
               35                  40                  45
Arg Thr Gly Trp Tyr Thr Ser Val Ile Thr Ile Glu Leu Ser Asn Ile
 50                  55                  60

Lys Glu Asn Lys Cys Asn Gly Thr Asp Ala Lys Val Lys Leu Ile Lys
 65                  70                  75                  80

Gln Glu Leu Asp Lys Tyr Lys Asn Ala Val Thr Glu Leu Gln Leu Leu
                     85                  90                  95

Met Gln Ser Thr Pro Ala Thr Asn Asn Arg Ala Arg Arg Glu Leu Pro
                100                 105                 110

Arg Phe Met Asn Tyr Thr Leu Asn Asn Ala Lys Lys Thr Asn Val Thr
            115                 120                 125

Leu Ser Lys Lys Arg Lys Arg Arg Phe Leu Gly Phe Leu Leu Gly Val
        130                 135                 140

Gly Ser Tyr Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                    165                 170                 175

Ala Val Val Ser Leu Ser Asn Gly Val Ser Val Leu Thr Ser Lys Val
                180                 185                 190

Leu Asp Leu Lys Asn Tyr Ile Asp Lys Gln Leu Leu Pro Ile Val Asn
            195                 200                 205

Lys Gln Ser Cys Ser Ile Ser Asn Ile Glu Thr Val Ile Glu Phe Gln
        210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
                260                 265                 270

Leu Met Ser Asn Asn Val Gln Ile Val Arg Gln Gln Ser Tyr Ser Ile
            275                 280                 285

Met Ser Ile Ile Lys Glu Glu Val Leu Ala Tyr Val Val Gln Leu Pro
        290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
                340                 345                 350

Pro Gln Ala Glu Thr Cys Lys Val Gln Ser Asn Arg Val Phe Cys Asp
            355                 360                 365

Thr Met Asn Ser Leu Thr Leu Pro Ser Glu Val Asn Leu Cys Asn Val
        370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
                420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Gln Glu Gly
        450                 455                 460
```

```
Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu Ser Ala Ile Gly Gly Tyr Ile Pro Glu Ala Pro Arg Asp Gly Gln
            515                 520                 525

Ala Tyr Val Arg Lys Asp Gly Glu Trp Val Leu Leu Ser Thr Phe Leu
            530                 535                 540

Gly Gly Leu Val Pro Arg Gly Ser His His His His His His Ser Ala
545                 550                 555                 560

Trp Ser His Pro Gln Phe Glu Lys
                565
```

<210> SEQ ID NO 12
<211> LENGTH: 568
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Tyr Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
```

245                 250                 255
Leu Leu Ser Leu Ile Asn Asp Met Pro Ile Thr Asn Asp Gln Lys Lys
                260                 265                 270
Leu Met Ser Asn Asn Val Gln Ile Val Arg Gln Gln Ser Tyr Ser Ile
            275                 280                 285
Met Ser Ile Ile Lys Glu Glu Val Leu Ala Tyr Val Val Gln Leu Pro
        290                 295                 300
Leu Tyr Gly Val Ile Asp Thr Pro Cys Trp Lys Leu His Thr Ser Pro
305                 310                 315                 320
Leu Cys Thr Thr Asn Thr Lys Glu Gly Ser Asn Ile Cys Leu Thr Arg
                325                 330                 335
Thr Asp Arg Gly Trp Tyr Cys Asp Asn Ala Gly Ser Val Ser Phe Phe
                340                 345                 350
Pro Gln Ala Glu Thr Cys Lys Val Gln Ser Asn Arg Val Phe Cys Asp
            355                 360                 365
Thr Met Asn Ser Leu Thr Leu Pro Ser Glu Val Asn Leu Cys Asn Val
        370                 375                 380
Asp Ile Phe Asn Pro Lys Tyr Asp Cys Lys Ile Met Thr Ser Lys Thr
385                 390                 395                 400
Asp Val Ser Ser Ser Val Ile Thr Ser Leu Gly Ala Ile Val Ser Cys
                405                 410                 415
Tyr Gly Lys Thr Lys Cys Thr Ala Ser Asn Lys Asn Arg Gly Ile Ile
                420                 425                 430
Lys Thr Phe Ser Asn Gly Cys Asp Tyr Val Ser Asn Lys Gly Val Asp
            435                 440                 445
Thr Val Ser Val Gly Asn Thr Leu Tyr Tyr Val Asn Lys Gln Glu Gly
        450                 455                 460
Lys Ser Leu Tyr Val Lys Gly Glu Pro Ile Ile Asn Phe Tyr Asp Pro
465                 470                 475                 480
Leu Val Phe Pro Ser Asp Glu Phe Asp Ala Ser Ile Ser Gln Val Asn
                485                 490                 495
Glu Lys Ile Asn Gln Ser Leu Ala Phe Ile Arg Lys Ser Asp Glu Leu
                500                 505                 510
Leu Ser Ala Ile Gly Gly Tyr Ile Pro Glu Ala Pro Arg Asp Gly Gln
            515                 520                 525
Ala Tyr Val Arg Lys Asp Gly Glu Trp Val Leu Leu Ser Thr Phe Leu
        530                 535                 540
Gly Gly Leu Val Pro Arg Gly Ser His His His His His His Ser Ala
545                 550                 555                 560
Trp Ser His Pro Gln Phe Glu Lys
                565

<210> SEQ ID NO 13
<211> LENGTH: 568
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met Glu Leu Leu Ile Leu Lys Ala Asn Ala Ile Thr Thr Ile Leu Thr
1               5                   10                  15
Ala Val Thr Phe Cys Phe Ala Ser Gly Gln Asn Ile Thr Glu Glu Phe
            20                  25                  30

-continued

```
Tyr Gln Ser Thr Cys Ser Ala Val Ser Lys Gly Tyr Leu Ser Ala Leu
         35                  40                  45

Arg Thr Gly Trp Tyr Thr Ser Val Ile Thr Ile Glu Leu Ser Asn Ile
 50                  55                  60

Lys Glu Asn Lys Cys Asn Gly Thr Asp Ala Lys Val Lys Leu Ile Lys
 65                  70                  75                  80

Gln Glu Leu Asp Lys Tyr Lys Asn Ala Val Thr Glu Leu Gln Leu Leu
                 85                  90                  95

Met Gln Ser Thr Pro Ala Thr Asn Asn Arg Ala Arg Arg Glu Leu Pro
             100                 105                 110

Arg Phe Met Asn Tyr Thr Leu Asn Asn Ala Lys Lys Thr Asn Val Thr
         115                 120                 125

Leu Ser Lys Lys Arg Lys Arg Arg Phe Leu Gly Phe Leu Leu Gly Val
130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                 165                 170                 175

Ala Val Val Ser Leu Ser Asn Gly Val Ser Val Leu Thr Ser Lys Val
             180                 185                 190

Leu Asp Leu Lys Asn Tyr Ile Asp Lys Gln Leu Leu Pro Ile Val Asn
         195                 200                 205

Lys Gln Ser Cys Ser Ile Ser Asn Ile Glu Thr Val Ile Tyr Phe Gln
210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                 245                 250                 255

Leu Leu Ser Leu Ile Asn Asp Met Pro Ile Thr Asn Asp Gln Lys Lys
             260                 265                 270

Leu Met Ser Asn Asn Val Gln Ile Val Arg Gln Gln Ser Tyr Ser Ile
         275                 280                 285

Met Ser Ile Ile Lys Glu Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                 325                 330                 335

Thr Asp Arg Gly Trp Tyr Cys Asp Asn Ala Gly Ser Val Ser Phe Phe
             340                 345                 350

Pro Gln Ala Glu Thr Cys Lys Val Gln Ser Asn Arg Val Phe Cys Asp
         355                 360                 365

Thr Met Asn Ser Leu Thr Leu Pro Ser Glu Val Asn Leu Cys Asn Val
370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                 405                 410                 415

Tyr Gly Lys Thr Lys Cys Thr Ala Ser Asn Lys Asn Arg Gly Ile Ile
             420                 425                 430

Lys Thr Phe Ser Asn Gly Cys Asp Tyr Val Ser Asn Lys Gly Val Asp
         435                 440                 445

Thr Val Ser Val Gly Asn Thr Leu Tyr Tyr Val Asn Lys Gln Glu Gly
```

```
              450                 455                 460
Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
                500                 505                 510

Leu Ser Ala Ile Gly Gly Tyr Ile Pro Glu Ala Pro Arg Asp Gly Gln
                515                 520                 525

Ala Tyr Val Arg Lys Asp Gly Glu Trp Val Leu Leu Ser Thr Phe Leu
                530                 535                 540

Gly Gly Leu Val Pro Arg Gly Ser His His His His His His Ser Ala
545                 550                 555                 560

Trp Ser His Pro Gln Phe Glu Lys
                565

<210> SEQ ID NO 14
<211> LENGTH: 568
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Tyr Gln
210                 215                 220

Gln Lys Asn Asn Arg Leu Leu Glu Ile Thr Arg Glu Phe Ser Val Asn
225                 230                 235                 240
```

```
Ala Gly Val Thr Thr Pro Val Ser Thr Tyr Met Leu Thr Asn Ser Glu
            245                 250                 255

Leu Leu Ser Leu Ile Asn Asp Met Pro Ile Thr Asn Asp Gln Lys Lys
        260                 265                 270

Leu Met Ser Asn Asn Val Gln Ile Val Arg Gln Gln Ser Tyr Ser Ile
    275                 280                 285

Met Ser Ile Ile Lys Glu Glu Val Leu Ala Tyr Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu Ser Ala Ile Gly Gly Tyr Ile Pro Glu Ala Pro Arg Asp Gly Gln
        515                 520                 525

Ala Tyr Val Arg Lys Asp Gly Glu Trp Val Leu Leu Ser Thr Phe Leu
    530                 535                 540

Gly Gly Leu Val Pro Arg Gly Ser His His His His His His Ser Ala
545                 550                 555                 560

Trp Ser His Pro Gln Phe Glu Lys
                565

<210> SEQ ID NO 15
<211> LENGTH: 568
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30
```

```
Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
50                  55                  60

Lys Glu Asn Lys Cys Asn Gly Thr Asp Ala Lys Val Lys Leu Ile Lys
65              70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Tyr Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445
```

Thr Val Ser Val Gly Asn Thr Leu Tyr Tyr Val Asn Lys Gln Glu Gly
450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
            485                 490                 495

Glu Lys Ile Asn Gln Ser Leu Ala Phe Ile Arg Lys Ser Asp Glu Leu
        500                 505                 510

Leu Ser Ala Ile Gly Gly Tyr Ile Pro Glu Ala Pro Arg Asp Gly Gln
            515                 520                 525

Ala Tyr Val Arg Lys Asp Gly Glu Trp Val Leu Leu Ser Thr Phe Leu
530                 535                 540

Gly Gly Leu Val Pro Arg Gly Ser His His His His His His Ser Ala
545                 550                 555                 560

Trp Ser His Pro Gln Phe Glu Lys
                565

<210> SEQ ID NO 16
<211> LENGTH: 568
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 16

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
            245                 250                 255

Leu Leu Ser Leu Ile Asn Asp Met Pro Ile Thr Asn Asp Gln Lys Lys
        260                 265                 270

Leu Met Ser Asn Asn Val Gln Ile Val Arg Gln Ser Tyr Ser Ile
        275                 280                 285

Met Ser Ile Ile Lys Glu Val Leu Ala Tyr Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
                340                 345                 350

Pro Gln Ala Glu Thr Cys Lys Val Gln Ser Asn Arg Val Phe Cys Asp
                355                 360                 365

Thr Met Asn Ser Leu Thr Leu Pro Ser Glu Val Asn Leu Cys Asn Val
        370                 375                 380

Asp Ile Phe Asn Pro Lys Tyr Asp Cys Lys Ile Met Thr Ser Lys Thr
385                 390                 395                 400

Asp Val Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
                420                 425                 430

Lys Thr Phe Ser Asn Gly Cys Asp Tyr Val Ser Asn Lys Gly Val Asp
                435                 440                 445

Thr Val Ser Val Gly Asn Thr Leu Tyr Tyr Val Asn Lys Gln Glu Gly
        450                 455                 460

Lys Ser Leu Tyr Tyr Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
                500                 505                 510

Leu Ser Ala Ile Gly Gly Tyr Ile Pro Glu Ala Pro Arg Asp Gly Gln
                515                 520                 525

Ala Tyr Val Arg Lys Asp Gly Glu Trp Val Leu Leu Ser Thr Phe Leu
        530                 535                 540

Gly Gly Leu Val Pro Arg Gly Ser His His His His His His Ser Ala
545                 550                 555                 560

Trp Ser His Pro Gln Phe Glu Lys
                565

<210> SEQ ID NO 17
<211> LENGTH: 568
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe

```
                20                  25                  30
Tyr Gln Ser Thr Cys Ser Ala Val Ser Lys Gly Tyr Leu Ser Ala Leu
                35                  40                  45
Arg Thr Gly Trp Tyr Thr Ser Val Ile Thr Ile Glu Leu Ser Asn Ile
 50                  55                  60
Lys Glu Asn Lys Cys Asn Gly Thr Asp Ala Lys Val Tyr Leu Ile Lys
 65                  70                  75                  80
Gln Glu Leu Asp Lys Tyr Lys Asn Ala Val Thr Glu Leu Gln Leu Leu
                85                  90                  95
Met Gln Ser Thr Pro Ala Thr Asn Asn Arg Ala Arg Arg Glu Leu Pro
                100                 105                 110
Arg Phe Met Asn Tyr Thr Leu Asn Asn Ala Lys Lys Thr Asn Val Thr
                115                 120                 125
Leu Ser Lys Lys Arg Lys Arg Arg Phe Leu Gly Phe Leu Leu Gly Val
                130                 135                 140
Gly Ser Ala Ile Ala Ser Gly Val Ala Val Ser Lys Val Leu His Leu
145                 150                 155                 160
Glu Gly Glu Val Asn Lys Ile Lys Ser Ala Leu Leu Ser Thr Asn Lys
                165                 170                 175
Ala Val Val Ser Leu Ser Asn Gly Val Ser Val Leu Thr Ser Lys Val
                180                 185                 190
Leu Asp Leu Lys Asn Tyr Ile Asp Lys Gln Leu Leu Pro Ile Val Asn
                195                 200                 205
Lys Gln Ser Cys Ser Ile Ser Asn Ile Glu Thr Val Ile Tyr Phe Gln
                210                 215                 220
Gln Lys Asn Asn Arg Leu Leu Glu Ile Thr Arg Glu Phe Ser Val Asn
225                 230                 235                 240
Ala Gly Val Thr Thr Pro Val Ser Thr Tyr Met Leu Thr Asn Ser Glu
                245                 250                 255
Leu Leu Ser Leu Ile Asn Asp Met Pro Ile Thr Asn Asp Gln Lys Lys
                260                 265                 270
Leu Met Ser Asn Asn Val Gln Ile Val Arg Gln Gln Ser Tyr Ser Ile
                275                 280                 285
Met Ser Ile Ile Lys Glu Glu Val Leu Ala Tyr Val Val Gln Leu Pro
                290                 295                 300
Leu Tyr Gly Val Ile Asp Thr Pro Cys Trp Lys Leu His Thr Ser Pro
305                 310                 315                 320
Leu Cys Thr Thr Asn Thr Lys Glu Gly Ser Asn Ile Cys Leu Thr Arg
                325                 330                 335
Thr Asp Arg Gly Trp Tyr Cys Asp Asn Ala Gly Ser Val Ser Phe Phe
                340                 345                 350
Pro Gln Ala Glu Thr Cys Lys Val Gln Ser Asn Arg Val Phe Cys Asp
                355                 360                 365
Thr Met Asn Ser Leu Thr Leu Pro Ser Glu Val Asn Leu Cys Asn Val
                370                 375                 380
Asp Ile Phe Asn Pro Lys Tyr Asp Cys Lys Ile Met Thr Ser Lys Thr
385                 390                 395                 400
Asp Val Ser Ser Ser Val Ile Thr Ser Leu Gly Ala Ile Val Ser Cys
                405                 410                 415
Tyr Gly Lys Thr Lys Cys Thr Ala Ser Asn Lys Asn Arg Gly Ile Ile
                420                 425                 430
Lys Thr Phe Ser Asn Gly Cys Asp Tyr Val Ser Asn Lys Gly Val Asp
                435                 440                 445
```

Thr Val Ser Val Gly Asn Thr Leu Tyr Tyr Val Asn Lys Gln Glu Gly
        450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu Ser Ala Ile Gly Gly Tyr Ile Pro Glu Ala Pro Arg Asp Gly Gln
        515                 520                 525

Ala Tyr Val Arg Lys Asp Gly Glu Trp Val Leu Leu Ser Thr Phe Leu
    530                 535                 540

Gly Gly Leu Val Pro Arg Gly Ser His His His His His His Ser Ala
545                 550                 555                 560

Trp Ser His Pro Gln Phe Glu Lys
                565

<210> SEQ ID NO 18
<211> LENGTH: 568
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Tyr Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn

```
              225                 230                 235                 240
Ala Gly Val Thr Thr Pro Val Ser Thr Tyr Met Leu Thr Asn Tyr Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
                340                 345                 350

Pro Gln Ala Glu Thr Cys Lys Val Gln Ser Asn Arg Val Phe Cys Asp
                355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
                420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Gln Glu Gly
        450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
                500                 505                 510

Leu Ser Ala Ile Gly Gly Tyr Ile Pro Glu Ala Pro Arg Asp Gly Gln
            515                 520                 525

Ala Tyr Val Arg Lys Asp Gly Glu Trp Val Leu Leu Ser Thr Phe Leu
        530                 535                 540

Gly Gly Leu Val Pro Arg Gly Ser His His His His His His Ser Ala
545                 550                 555                 560

Trp Ser His Pro Gln Phe Glu Lys
                565

<210> SEQ ID NO 19
<211> LENGTH: 568
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Met Glu Leu Leu Ile Leu Lys Ala Asn Ala Ile Thr Thr Ile Leu Thr
1               5                   10                  15
```

-continued

```
Ala Val Thr Phe Cys Phe Ala Ser Gln Asn Ile Thr Glu Phe
            20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
        50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Tyr Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
            115                 120                 125

Leu Ser Lys Lys Arg Lys Arg Arg Phe Leu Gly Phe Leu Leu Gly Val
        130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
            245                 250                 255

Leu Leu Ser Leu Ile Asn Asp Met Pro Ile Thr Asn Asp Gln Lys Lys
        260                 265                 270

Leu Met Ser Asn Asn Val Gln Ile Val Arg Gln Gln Ser Tyr Ser Ile
    275                 280                 285

Met Ser Ile Ile Lys Glu Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
```

```
                 435                 440                 445
Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu Ser Ala Ile Gly Gly Tyr Ile Pro Glu Ala Pro Arg Asp Gly Gln
        515                 520                 525

Ala Tyr Val Arg Lys Asp Gly Glu Trp Val Leu Leu Ser Thr Phe Leu
    530                 535                 540

Gly Gly Leu Val Pro Arg Gly Ser His His His His His His Ser Ala
545                 550                 555                 560

Trp Ser His Pro Gln Phe Glu Lys
                565

<210> SEQ ID NO 20
<211> LENGTH: 568
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Tyr Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220
```

```
Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
            245                 250                 255

Leu Leu Ser Leu Ile Asn Asp Met Pro Ile Thr Asn Asp Gln Lys Lys
        260                 265                 270

Leu Met Ser Asn Asn Val Gln Ile Val Arg Gln Gln Ser Tyr Ser Ile
    275                 280                 285

Met Ser Ile Ile Lys Glu Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
            325                 330                 335

Thr Asp Arg Gly Trp Tyr Cys Asp Asn Ala Gly Ser Val Ser Phe Phe
        340                 345                 350

Pro Gln Ala Glu Thr Cys Lys Val Gln Ser Asn Arg Val Phe Cys Asp
    355                 360                 365

Thr Met Asn Ser Leu Thr Leu Pro Ser Glu Val Asn Leu Cys Asn Val
370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
            405                 410                 415

Tyr Gly Lys Thr Lys Cys Thr Ala Ser Asn Tyr Asn Arg Gly Ile Ile
        420                 425                 430

Lys Thr Phe Ser Asn Gly Cys Asp Tyr Val Ser Asn Lys Gly Val Asp
    435                 440                 445

Thr Val Ser Val Gly Asn Thr Leu Tyr Tyr Val Asn Lys Gln Glu Gly
450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
            485                 490                 495

Glu Lys Ile Asn Gln Ser Leu Ala Phe Ile Arg Lys Ser Asp Glu Leu
        500                 505                 510

Leu Ser Ala Ile Gly Gly Tyr Ile Pro Glu Ala Pro Arg Asp Gly Gln
    515                 520                 525

Ala Tyr Val Arg Lys Asp Gly Glu Trp Val Leu Leu Ser Thr Phe Leu
530                 535                 540

Gly Gly Leu Val Pro Arg Gly Ser His His His His His His Ser Ala
545                 550                 555                 560

Trp Ser His Pro Gln Phe Glu Lys
                565

<210> SEQ ID NO 21
<211> LENGTH: 568
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Met Glu Leu Leu Ile Leu Lys Ala Asn Ala Ile Thr Thr Ile Leu Thr
1               5                   10                  15
```

```
Ala Val Thr Phe Cys Phe Ala Ser Gly Gln Asn Ile Thr Glu Glu Phe
         20                  25                  30

Tyr Gln Ser Thr Cys Ser Ala Val Ser Lys Gly Tyr Leu Ser Ala Leu
             35                  40                  45

Arg Thr Gly Trp Tyr Thr Ser Val Ile Thr Ile Glu Leu Ser Asn Ile
 50                  55                  60

Lys Glu Asn Lys Cys Asn Gly Thr Asp Ala Lys Val Lys Leu Ile Lys
 65                  70                  75                  80

Gln Glu Leu Asp Lys Tyr Lys Asn Ala Val Thr Glu Leu Gln Leu Leu
                 85                  90                  95

Met Gln Ser Thr Pro Ala Thr Asn Asn Arg Ala Arg Glu Leu Pro
             100                 105                 110

Arg Phe Met Asn Tyr Thr Leu Asn Asn Ala Lys Lys Thr Asn Val Thr
             115                 120                 125

Leu Ser Lys Lys Arg Lys Arg Arg Phe Leu Gly Phe Leu Leu Gly Val
     130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                 165                 170                 175

Ala Val Val Ser Leu Ser Asn Gly Val Ser Tyr Leu Thr Ser Lys Val
             180                 185                 190

Leu Asp Leu Lys Asn Tyr Ile Asp Lys Gln Leu Leu Pro Ile Val Asn
     195                 200                 205

Lys Gln Ser Cys Ser Ile Ser Asn Ile Glu Thr Val Ile Glu Phe Gln
     210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
             245                 250                 255

Leu Leu Ser Leu Ile Asn Asp Met Pro Ile Thr Asn Asp Gln Lys Lys
             260                 265                 270

Leu Met Ser Asn Asn Val Gln Ile Val Arg Gln Gln Ser Tyr Ser Ile
     275                 280                 285

Met Ser Ile Ile Lys Glu Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
             325                 330                 335

Thr Asp Arg Gly Trp Tyr Cys Asp Asn Ala Gly Ser Val Ser Phe Phe
             340                 345                 350

Pro Gln Ala Glu Thr Cys Lys Val Gln Ser Asn Arg Val Phe Cys Asp
     355                 360                 365

Thr Met Asn Ser Leu Thr Leu Pro Ser Glu Val Asn Leu Cys Asn Val
     370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
             405                 410                 415

Tyr Gly Lys Thr Lys Cys Thr Ala Ser Asn Tyr Asn Arg Gly Ile Ile
             420                 425                 430
```

-continued

```
Lys Thr Phe Ser Asn Gly Cys Asp Tyr Val Ser Asn Lys Gly Val Asp
            435                 440                 445

Thr Val Ser Val Gly Asn Thr Leu Tyr Val Asn Lys Gln Glu Gly
450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
            485                 490                 495

Glu Lys Ile Asn Gln Ser Leu Ala Phe Ile Arg Lys Ser Asp Glu Leu
            500                 505                 510

Leu Ser Ala Ile Gly Gly Tyr Ile Pro Glu Ala Pro Arg Asp Gly Gln
            515                 520                 525

Ala Tyr Val Arg Lys Asp Gly Glu Trp Val Leu Leu Ser Thr Phe Leu
530                 535                 540

Gly Gly Leu Val Pro Arg Gly Ser His His His His His His Ser Ala
545                 550                 555                 560

Trp Ser His Pro Gln Phe Glu Lys
            565
```

<210> SEQ ID NO 22
<211> LENGTH: 568
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Tyr Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220
```

```
Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
            245                 250                 255

Leu Leu Ser Leu Ile Asn Asp Met Pro Ile Thr Asn Asp Gln Lys Lys
        260                 265                 270

Leu Met Ser Asn Asn Val Gln Ile Val Arg Gln Gln Ser Tyr Ser Ile
    275                 280                 285

Met Ser Ile Ile Lys Glu Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Tyr Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Val Asn Lys Gln Glu Gly
450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu Ser Ala Ile Gly Gly Tyr Ile Pro Glu Ala Pro Arg Asp Gly Gln
        515                 520                 525

Ala Tyr Val Arg Lys Asp Gly Glu Trp Val Leu Leu Ser Thr Phe Leu
    530                 535                 540

Gly Gly Leu Val Pro Arg Gly Ser His His His His His His Ser Ala
545                 550                 555                 560

Trp Ser His Pro Gln Phe Glu Lys
                565

<210> SEQ ID NO 23
<211> LENGTH: 568
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Met Glu Leu Leu Ile Leu Lys Ala Asn Ala Ile Thr Thr Ile Leu Thr
```

```
1               5                   10                  15
Ala Val Thr Phe Cys Phe Ala Ser Gly Gln Asn Ile Thr Glu Glu Phe
            20                  25                  30
Tyr Gln Ser Thr Cys Ser Ala Val Ser Lys Gly Tyr Leu Ser Ala Leu
            35                  40                  45
Arg Thr Gly Trp Tyr Thr Ser Val Ile Thr Ile Glu Leu Ser Asn Ile
 50                  55                  60
Lys Glu Asn Lys Cys Asn Gly Thr Asp Ala Lys Val Lys Leu Ile Lys
 65                  70                  75                  80
Gln Glu Leu Asp Lys Tyr Lys Asn Ala Val Thr Glu Leu Gln Leu Leu
            85                  90                  95
Met Gln Ser Thr Pro Ala Thr Asn Asn Arg Ala Arg Arg Glu Leu Pro
            100                 105                 110
Arg Phe Met Asn Tyr Thr Leu Asn Asn Ala Lys Lys Thr Asn Val Thr
            115                 120                 125
Leu Ser Lys Lys Arg Lys Arg Arg Phe Leu Gly Phe Leu Leu Gly Val
 130                 135                 140
Gly Ser Tyr Ile Ala Ser Gly Val Ala Val Cys Lys Val Leu His Leu
 145                 150                 155                 160
Glu Gly Glu Val Asn Lys Ile Lys Ser Ala Leu Leu Ser Thr Asn Lys
            165                 170                 175
Ala Val Val Ser Leu Ser Asn Gly Val Ser Val Leu Thr Phe Lys Val
            180                 185                 190
Leu Asp Leu Lys Asn Tyr Ile Asp Lys Gln Leu Leu Pro Ile Leu Asn
            195                 200                 205
Lys Gln Ser Cys Ser Ile Ser Asn Ile Glu Thr Val Ile Glu Phe Gln
 210                 215                 220
Gln Lys Asn Asn Arg Leu Leu Glu Ile Thr Arg Glu Phe Ser Val Asn
 225                 230                 235                 240
Ala Gly Val Thr Thr Pro Val Ser Thr Tyr Met Leu Thr Asn Ser Glu
            245                 250                 255
Leu Leu Ser Leu Ile Asn Asp Met Pro Ile Thr Asn Asp Gln Lys Lys
            260                 265                 270
Leu Met Ser Asn Asn Val Gln Ile Val Arg Gln Gln Ser Tyr Ser Ile
            275                 280                 285
Met Cys Ile Ile Lys Glu Glu Val Leu Ala Tyr Val Val Gln Leu Pro
            290                 295                 300
Leu Tyr Gly Val Ile Asp Thr Pro Cys Trp Lys Leu His Thr Ser Pro
 305                 310                 315                 320
Leu Cys Thr Thr Asn Thr Lys Glu Gly Ser Asn Ile Cys Leu Thr Arg
            325                 330                 335
Thr Asp Arg Gly Trp Tyr Cys Asp Asn Ala Gly Ser Val Ser Phe Phe
            340                 345                 350
Pro Gln Ala Glu Thr Cys Lys Val Gln Ser Asn Arg Val Phe Cys Asp
            355                 360                 365
Thr Met Asn Ser Leu Thr Leu Pro Ser Glu Val Asn Leu Cys Asn Val
            370                 375                 380
Asp Ile Phe Asn Pro Lys Tyr Asp Cys Lys Ile Met Thr Ser Lys Thr
 385                 390                 395                 400
Asp Val Ser Ser Ser Val Ile Thr Ser Leu Gly Ala Ile Val Ser Cys
            405                 410                 415
Tyr Gly Lys Thr Lys Cys Thr Ala Ser Asn Lys Asn Arg Gly Ile Ile
            420                 425                 430
```

-continued

```
Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
                500                 505                 510

Leu Ser Ala Ile Gly Gly Tyr Ile Pro Glu Ala Pro Arg Asp Gly Gln
            515                 520                 525

Ala Tyr Val Arg Lys Asp Gly Glu Trp Val Leu Leu Ser Thr Phe Leu
        530                 535                 540

Gly Gly Leu Val Pro Arg Gly Ser His His His His His His Ser Ala
545                 550                 555                 560

Trp Ser His Pro Gln Phe Glu Lys
                565
```

```
<210> SEQ ID NO 24
<211> LENGTH: 568
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Cys Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Phe Lys Val
            180                 185                 190

Leu Asp Leu Lys Asn Tyr Ile Asp Lys Gln Leu Leu Pro Ile Leu Asn
        195                 200                 205

Lys Gln Ser Cys Ser Ile Ser Asn Ile Glu Thr Tyr Ile Glu Phe Gln
```

210                 215                 220
Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
            245                 250                 255

Leu Leu Ser Leu Ile Asn Asp Met Pro Ile Thr Asn Asp Gln Lys Lys
            260                 265                 270

Leu Met Ser Asn Val Gln Ile Val Arg Gln Ser Tyr Ser Ile
            275                 280                 285

Met Cys Ile Ile Lys Glu Val Leu Ala Tyr Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
            325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
            355                 360                 365

Thr Met Asn Ser Leu Thr Leu Pro Ser Glu Val Asn Leu Cys Asn Val
370                 375                 380

Asp Ile Phe Asn Pro Lys Tyr Asp Cys Lys Ile Met Thr Ser Lys Thr
385                 390                 395                 400

Asp Val Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Gln Glu Gly
450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
            485                 490                 495

Glu Lys Ile Asn Gln Ser Leu Ala Phe Ile Arg Lys Ser Asp Glu Leu
            500                 505                 510

Leu Ser Ala Ile Gly Gly Tyr Ile Pro Glu Ala Pro Arg Asp Gly Gln
            515                 520                 525

Ala Tyr Val Arg Lys Asp Gly Glu Trp Val Leu Leu Ser Thr Phe Leu
530                 535                 540

Gly Gly Leu Val Pro Arg Gly Ser His His His His His His Ser Ala
545                 550                 555                 560

Trp Ser His Pro Gln Phe Glu Lys
            565

<210> SEQ ID NO 25
<211> LENGTH: 568
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
                35                  40                  45

Arg Thr Gly Trp Tyr Thr Ser Val Ile Thr Ile Glu Leu Ser Asn Ile
            50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
                100                 105                 110

Arg Phe Met Asn Tyr Thr Leu Asn Asn Ala Lys Lys Thr Asn Val Thr
            115                 120                 125

Leu Ser Lys Lys Arg Lys Arg Arg Phe Leu Gly Phe Leu Leu Gly Val
        130                 135                 140

Gly Ser Ala Ile Ala Ser Gly Val Ala Val Cys Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Phe Lys Val
            180                 185                 190

Leu Asp Leu Lys Asn Tyr Ile Asp Lys Gln Leu Leu Pro Ile Leu Asn
        195                 200                 205

Lys Gln Ser Cys Ser Ile Ser Asn Ile Glu Thr Val Ile Tyr Phe Gln
210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
            245                 250                 255

Leu Leu Ser Leu Ile Asn Asp Met Pro Ile Thr Asn Asp Gln Lys Lys
        260                 265                 270

Leu Met Ser Asn Asn Val Gln Ile Val Arg Gln Gln Ser Tyr Ser Ile
        275                 280                 285

Met Cys Ile Ile Lys Glu Glu Val Leu Ala Tyr Val Val Gln Leu Pro
        290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
            325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
            355                 360                 365

Thr Met Asn Ser Leu Thr Leu Pro Ser Glu Val Asn Leu Cys Asn Val
            370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
```

```
                420                 425                 430
Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Gln Glu Gly
        450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu Ser Ala Ile Gly Gly Tyr Ile Pro Glu Ala Pro Arg Asp Gly Gln
        515                 520                 525

Ala Tyr Val Arg Lys Asp Gly Glu Trp Val Leu Leu Ser Thr Phe Leu
    530                 535                 540

Gly Gly Leu Val Pro Arg Gly Ser His His His His His His Ser Ala
545                 550                 555                 560

Trp Ser His Pro Gln Phe Glu Lys
                565

<210> SEQ ID NO 26
<211> LENGTH: 568
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Cys Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Phe Lys Val
            180                 185                 190

Leu Asp Leu Lys Asn Tyr Ile Asp Lys Gln Leu Leu Pro Ile Leu Asn
        195                 200                 205
```

Lys Gln Ser Cys Ser Ile Ser Asn Ile Glu Thr Val Ile Glu Tyr Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Cys Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu Ser Ala Ile Gly Gly Tyr Ile Pro Glu Ala Pro Arg Asp Gly Gln
        515                 520                 525

Ala Tyr Val Arg Lys Asp Gly Glu Trp Val Leu Leu Ser Thr Phe Leu
    530                 535                 540

Gly Gly Leu Val Pro Arg Gly Ser His His His His His His Ser Ala
545                 550                 555                 560

Trp Ser His Pro Gln Phe Glu Lys
                565

<210> SEQ ID NO 27
<211> LENGTH: 568
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 27

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
            85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Cys Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Phe Lys Val
            180                 185                 190

Leu Asp Leu Lys Asn Tyr Ile Asp Lys Gln Leu Leu Pro Ile Leu Asn
        195                 200                 205

Lys Gln Ser Cys Ser Ile Ser Asn Ile Glu Thr Val Ile Glu Phe Gln
    210                 215                 220

Gln Tyr Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
            245                 250                 255

Leu Leu Ser Leu Ile Asn Asp Met Pro Ile Thr Asn Asp Gln Lys Lys
        260                 265                 270

Leu Met Ser Asn Asn Val Gln Ile Val Arg Gln Gln Ser Tyr Ser Ile
    275                 280                 285

Met Cys Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
            325                 330                 335

Thr Asp Arg Gly Trp Tyr Cys Asp Asn Ala Gly Ser Val Ser Phe Phe
        340                 345                 350

Pro Gln Ala Glu Thr Cys Lys Val Gln Ser Asn Arg Val Phe Cys Asp
    355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
            405                 410                 415
```

```
Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu Ser Ala Ile Gly Gly Tyr Ile Pro Glu Ala Pro Arg Asp Gly Gln
        515                 520                 525

Ala Tyr Val Arg Lys Asp Gly Glu Trp Val Leu Leu Ser Thr Phe Leu
    530                 535                 540

Gly Gly Leu Val Pro Arg Gly Ser His His His His His His Ser Ala
545                 550                 555                 560

Trp Ser His Pro Gln Phe Glu Lys
                565
```

<210> SEQ ID NO 28
<211> LENGTH: 568
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Cys Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Phe Lys Val
            180                 185                 190

Leu Asp Leu Lys Asn Tyr Ile Asp Lys Gln Leu Leu Pro Ile Leu Asn
        195                 200                 205
```

-continued

Lys Gln Ser Cys Ser Ile Ser Asn Ile Glu Thr Val Ile Glu Phe Gln
            210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
            245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Ser Tyr Ser Ile
            275                 280                 285

Met Cys Ile Ile Lys Glu Val Leu Ala Tyr Val Val Gln Leu Pro
            290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
            325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
            355                 360                 365

Thr Met Asn Ser Leu Thr Leu Pro Ser Glu Val Asn Leu Cys Asn Val
370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Gln Glu Gly
            450                 455                 460

Lys Ser Leu Tyr Tyr Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
            485                 490                 495

Glu Lys Ile Asn Gln Ser Leu Ala Phe Ile Arg Lys Ser Asp Glu Leu
            500                 505                 510

Leu Ser Ala Ile Gly Gly Tyr Ile Pro Glu Ala Pro Arg Asp Gly Gln
            515                 520                 525

Ala Tyr Val Arg Lys Asp Gly Glu Trp Val Leu Leu Ser Thr Phe Leu
            530                 535                 540

Gly Gly Leu Val Pro Arg Gly Ser His His His His His His Ser Ala
545                 550                 555                 560

Trp Ser His Pro Gln Phe Glu Lys
                565

<210> SEQ ID NO 29
<211> LENGTH: 568
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 29

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Tyr Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415
```

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Val Asn Lys Gln Glu Gly
            450                 455                 460

Lys Ser Leu Tyr Tyr Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu Ser Ala Ile Gly Gly Tyr Ile Pro Glu Ala Pro Arg Asp Gly Gln
            515                 520                 525

Ala Tyr Val Arg Lys Asp Gly Glu Trp Val Leu Leu Ser Thr Phe Leu
            530                 535                 540

Gly Gly Leu Val Pro Arg Gly Ser His His His His His His Ser Ala
545                 550                 555                 560

Trp Ser His Pro Gln Phe Glu Lys
                565

<210> SEQ ID NO 30
<211> LENGTH: 568
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
            50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
            115                 120                 125

Leu Ser Lys Lys Arg Lys Arg Arg Phe Leu Gly Phe Leu Leu Gly Val
            130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn

```
                195                 200                 205
Lys Gln Ser Cys Ser Ile Ser Asn Ile Glu Thr Val Ile Glu Phe Gln
210                 215                 220

Gln Tyr Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Tyr Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu Ser Ala Ile Gly Gly Tyr Ile Pro Glu Ala Pro Arg Asp Gly Gln
        515                 520                 525

Ala Tyr Val Arg Lys Asp Gly Glu Trp Val Leu Leu Ser Thr Phe Leu
    530                 535                 540

Gly Gly Leu Val Pro Arg Gly Ser His His His His His His Ser Ala
545                 550                 555                 560

Trp Ser His Pro Gln Phe Glu Lys
                565

<210> SEQ ID NO 31
<211> LENGTH: 568
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 31

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
130                 135                 140

Gly Ser Ala Ile Ala Ser Gly Val Ala Val Cys Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Phe Lys Val
            180                 185                 190

Leu Asp Leu Lys Asn Tyr Ile Asp Lys Gln Leu Leu Pro Ile Leu Asn
        195                 200                 205

Lys Gln Ser Cys Ser Ile Ser Asn Ile Glu Thr Val Ile Tyr Phe Gln
210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Cys Ile Ile Lys Glu Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys

```
                        405                 410                 415
Tyr Gly Lys Thr Lys Cys Thr Ala Ser Asn Lys Asn Arg Gly Ile Ile
                420                 425                 430

Lys Thr Phe Ser Asn Gly Cys Asp Tyr Val Ser Asn Lys Gly Val Asp
                435                 440                 445

Thr Val Ser Val Gly Asn Thr Leu Tyr Tyr Val Asn Lys Gln Glu Gly
            450                 455                 460

Lys Ser Leu Tyr Tyr Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu Ser Ala Ile Gly Gly Tyr Ile Pro Glu Ala Pro Arg Asp Gly Gln
            515                 520                 525

Ala Tyr Val Arg Lys Asp Gly Glu Trp Val Leu Leu Ser Thr Phe Leu
            530                 535                 540

Gly Gly Leu Val Pro Arg Gly Ser His His His His His His Ser Ala
545                 550                 555                 560

Trp Ser His Pro Gln Phe Glu Lys
                565

<210> SEQ ID NO 32
<211> LENGTH: 568
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
        50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Cys Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Phe Lys Val
            180                 185                 190
```

```
Leu Asp Leu Lys Asn Tyr Ile Asp Lys Gln Leu Leu Pro Ile Leu Asn
            195                 200                 205
Lys Gln Ser Cys Ser Ile Ser Asn Ile Glu Thr Val Ile Glu Phe Gln
        210                 215                 220
Gln Tyr Asn Asn Arg Leu Leu Glu Ile Thr Arg Glu Phe Ser Val Asn
225                 230                 235                 240
Ala Gly Val Thr Thr Pro Val Ser Thr Tyr Met Leu Thr Asn Ser Glu
                245                 250                 255
Leu Leu Ser Leu Ile Asn Asp Met Pro Ile Thr Asn Asp Gln Lys Lys
            260                 265                 270
Leu Met Ser Asn Asn Val Gln Ile Val Arg Gln Gln Ser Tyr Ser Ile
        275                 280                 285
Met Cys Ile Ile Lys Glu Glu Val Leu Ala Tyr Val Val Gln Leu Pro
    290                 295                 300
Leu Tyr Gly Val Ile Asp Thr Pro Cys Trp Lys Leu His Thr Ser Pro
305                 310                 315                 320
Leu Cys Thr Thr Asn Thr Lys Glu Gly Ser Asn Ile Cys Leu Thr Arg
                325                 330                 335
Thr Asp Arg Gly Trp Tyr Cys Asp Asn Ala Gly Ser Val Ser Phe Phe
            340                 345                 350
Pro Gln Ala Glu Thr Cys Lys Val Gln Ser Asn Arg Val Phe Cys Asp
        355                 360                 365
Thr Met Asn Ser Leu Thr Leu Pro Ser Glu Val Asn Leu Cys Asn Val
    370                 375                 380
Asp Ile Phe Asn Pro Lys Tyr Asp Cys Lys Ile Met Thr Ser Lys Thr
385                 390                 395                 400
Asp Val Ser Ser Ser Val Ile Thr Ser Leu Gly Ala Ile Val Ser Cys
                405                 410                 415
Tyr Gly Lys Thr Lys Cys Thr Ala Ser Asn Lys Asn Arg Gly Ile Ile
            420                 425                 430
Lys Thr Phe Ser Asn Gly Cys Asp Tyr Val Ser Asn Lys Gly Val Asp
        435                 440                 445
Thr Val Ser Val Gly Asn Thr Leu Tyr Tyr Val Asn Lys Gln Glu Gly
    450                 455                 460
Lys Ser Leu Tyr Tyr Lys Gly Glu Pro Ile Ile Asn Phe Tyr Asp Pro
465                 470                 475                 480
Leu Val Phe Pro Ser Asp Glu Phe Asp Ala Ser Ile Ser Gln Val Asn
                485                 490                 495
Glu Lys Ile Asn Gln Ser Leu Ala Phe Ile Arg Lys Ser Asp Glu Leu
            500                 505                 510
Leu Ser Ala Ile Gly Gly Tyr Ile Pro Glu Ala Pro Arg Asp Gly Gln
        515                 520                 525
Ala Tyr Val Arg Lys Asp Gly Glu Trp Val Leu Leu Ser Thr Phe Leu
    530                 535                 540
Gly Gly Leu Val Pro Arg Gly Ser His His His His His His Ser Ala
545                 550                 555                 560
Trp Ser His Pro Gln Phe Glu Lys
                565

<210> SEQ ID NO 33
<211> LENGTH: 1725
<212> TYPE: DNA
<213> ORGANISM: Human respiratory syncytial virus

<400> SEQUENCE: 33
```
atggagttgc taatcctcaa agcaaatgca attaccacaa tcctcactgc agtcacattt 60
tgttttgctt ctggtcaaaa catcactgaa gaattttatc aatcaacatg cagtgcagtt 120
agcaaaggct atcttagtgc tctgagaact ggttggtata ccagtgttat aactatagaa 180
ttaagtaata tcaagaaaaa taagtgtaat ggaacagatg ctaaggtaaa attgataaaa 240
caagaattag ataaatataa aaatgctgta acagaattgc agttgctcat gcaaagcaca 300
ccagcaacaa acaatcgagc cagaagagaa ctaccaaggt ttatgaatta tacactcaac 360
aatgccaaaa aaaccaatgt aacattaagc aagaaaagga aaagaagatt tcttggtttt 420
ttgttaggtg ttggatctgc aatcgccagt ggcgttgctg tatctaaggt cctgcaccta 480
gaaggggaag tgaacaagat caaaagtgct ctactatcca caaacaaggc tgtagtcagc 540
ttatcaaatg gagtcagtgt cttaaccagc aaagtgttag acctcaaaaa ctatatagat 600
aaacaattgt tacctattgt gaacaagcaa agctgcagca tatcaaatat agaaactgtg 660
atagagttcc aacaaaagaa caacagacta ctagagatta ccagggaatt tagtgttaat 720
gcaggtgtaa ctacacctgt aagcacttac atgttaacta atagtgaatt attgtcatta 780
atcaatgata tgcctataac aaatgatcag aaaaagttaa tgtccaacaa tgttcaaata 840
gttagacagc aaagttactc tatcatgtcc ataataaaag aggaagtctt agcatatgta 900
gtacaattac cactatatgg tgttatagat acaccctgtt ggaaactaca cacatcccct 960
ctatgtacaa ccaacacaaa agaagggtcc aacatctgtt taacaagaac tgacagagga 1020
tggtactgtg acaatgcagg atcagtatct ttcttcccac aagctgaaac atgtaaagtt 1080
caatcaaatc gagtattttg tgacacaatg aacagtttaa cattaccaag tgaagtaaat 1140
ctctgcaatg ttgacatatt caaccccaaa tatgattgta aaattatgac ttcaaaaaca 1200
gatgtaagca gctccgttat cacatctcta ggagccattg tgtcatgcta tggcaaaact 1260
aaatgtacag catccaataa aaatcgtgga atcataaaga cattttctaa cgggtgcgat 1320
tatgtatcaa ataaaggggt ggacactgtg tctgtaggta acacattata ttatgtaaat 1380
aagcaagaag gtaaaagtct ctatgtaaaa ggtgaaccaa taataaattt ctatgaccca 1440
ttagtattcc cctctgatga atttgatgca tcaatatctc aagtcaacga gaagattaac 1500
cagagcctag catttattcg taaatccgat gaattattac ataatgtaaa tgccggtaaa 1560
tccaccacaa atatcatgat aactactata attatagtga ttatagtaat attgttatca 1620
ttaattgctg ttggactgct cttatactgt aaggccagaa gcacaccagt cacactaagc 1680
aaagatcaac tgagtggtat aaataatatt gcatttagta actaa 1725

<210> SEQ ID NO 34
<211> LENGTH: 1725
<212> TYPE: DNA
<213> ORGANISM: Human respiratory syncytial virus

<400> SEQUENCE: 34
atggagttgc tgatccacag gtcaagtgca atcttcctaa ctcttgctat taatgcattg 60
tacctcacct caagtcagaa cataactgag gagttttacc aatcgacatg tagtgcagtt 120
agcagaggtt attttagtgc tttaagaaca ggttggtata ccagtgtcat aacaatagaa 180
ttaagtaata taacagaaac caaatgcaat ggaactgaca ctaaagtaaa acttataaaa 240
caagaattag ataagtataa gaatgcagta acagaattac agctacttat gcaaaacacg 300
ccagctgcca acaaccgggc cagaagagaa gcaccacagc acatgaacta cacaatcaat 360

| | |
|---|---|
| accactaaaa acctaaatgt atcaataagc aagaagagga aacgaagatt tctgggcttc | 420 |
| ttgttaggtg taggatctgc aatagcaagt ggtatagctg tatccaaagt tctacacctt | 480 |
| gaaggagaag tgaacaaaat caaaaatgct tgttgtcta caaacaaagc tgtagtcagt | 540 |
| ctatcaaatg gggtcagtgt tttaaccagc aaagtgttag atctcaagaa ttacataaat | 600 |
| aaccaattat tacccatagt aaatcaacag agctgtcgca tcttcaacat tgaaacagtt | 660 |
| atagaattcc aacagaagaa tagcagattg ttggaaatca ccagagaatt tagtgtcaat | 720 |
| gcaggtgtaa caacaccttt aagcacttac atgttaacaa acagtgagtt actatcattg | 780 |
| atcaatgata tgcctataac aaatgatcag aaaaaattaa tgtcaagcaa tgttcagata | 840 |
| gtaaggcaac aaagttattc tatcatgtct ataataaagg aagaagtcct tgcatatgtt | 900 |
| gtacagctac ctatctatgg tgtaatagat acaccttgct ggaaattaca cacatcacct | 960 |
| ctatgcacca ccaacatcaa agaaggatca aatatttgtt taacaaggac tgatagagga | 1020 |
| tggtattgtg ataatgcagg atcagtatcc ttcttcccac aggctgacac ttgcaaagta | 1080 |
| cagtccaatc gagtattttg tgacactatg aacagtttga cattaccaag tgaagtcagc | 1140 |
| ctttgtaaca ctgacatatt caattccaag tatgactgca aaattatgac atcaaaaaca | 1200 |
| gacataagca gctcagtaat tacttctctt ggagctatag tgtcatgtta tggtaaaact | 1260 |
| aaatgcactg catccaataa aaatcgtggg attataaaga cattttctaa tggttgtgac | 1320 |
| tatgtgtcaa acaaggagt agatactgtg tcagtgggca cactttata ctatgtaaac | 1380 |
| aagctggaag gcaagaacct ttatgtaaaa ggggaaccta taataatta ctatgatcct | 1440 |
| ctagtgtttc cttctgatga gtttgatgca tcaatatctc aagtcaatga aaaaatcaat | 1500 |
| caaagtttag ctttttattcg taaatctgat gaattactac ataatgtaaa tactggcaaa | 1560 |
| tctactacaa atattatgat aactacaatt attatagtaa tcattgtagt attgttatca | 1620 |
| ttaatagcta ttggtttact gttgtattgc aaagccaaaa acacaccagt tacactaagc | 1680 |
| aaagaccaac taagtggaat caataatatt gcattcagca aatag | 1725 |

<210> SEQ ID NO 35
<211> LENGTH: 1725
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 35

| | |
|---|---|
| atggagctgc tcatcctgaa ggccaacgcc atcaccacca tcctcaccgc cgtgaccttc | 60 |
| tgcttcgcca gcggccagaa tatcaccgag gagttctacc agagcacctg cagcgccgtg | 120 |
| agcaagggct acctgagcgc cctgagaacc ggctggtaca ccagcgtgat caccatcgag | 180 |
| ctgagcaaca tcaagaagaa caagtgcaac ggcaccgacg ccaaggtgaa gctcatcaag | 240 |
| caggagctgg acaagtacaa gaacgccgtg accgagctgc agctgctcat gcagagcacc | 300 |
| caggccacca acaacagggc cagaagggag ctgccccggt tcatgaacta caccctgaac | 360 |
| aacgccaaga aaaccaacgt gaccctgagc aagaagcgga gcggagatt cctgggcttc | 420 |
| ctgctgggcg tgggcagcgc catcgccagc ggagtggccg tgtccaaggt gctgcacctg | 480 |
| gagggcgagg tgaacaagat caagagcgcc ctgctgagca ccaacaaggc cgtggtgagc | 540 |
| ctgagcaacg gcgtgagcgt gctcaccagc aaggtgctgg atctgaagaa ctacatcgac | 600 |
| aagcagctgc tgcccatcgt gaacaagcag agctgcagca tcagcaacat cgagaccgtg | 660 |

```
atcgagttcc agcagaagaa caaccggctg ctggagatca ccagggagtt cagcgtgaac    720
gccggcgtga ccaccccgt gagcacctac atgctcacca acagcgagct gctgagcctc    780
atcaacgaca tgcccatcac caacgaccag aagaagctca tgagcaacaa cgtgcagatc    840
gtgcggcagc agagctactc catcatgagc atcatcaagg aggaggtgct ggcctacgtg    900
gtgcagctgc ccctgtacgg cgtgatcgat accccttgct ggaagctgca caccagcccc    960
ctgtgcacca ccaacaccaa ggagggcagc aacatctgcc tcaccaggac cgatagaggc   1020
tggtactgcg acaacgccgg cagcgtgtca ttctttccac aggccgagac ctgcaaggtg   1080
cagagcaacc gggtgttctg cgacaccatg aacagcctca ccctgcccag cgaagtgaac   1140
ctgtgcaacg tggacatctt caaccccaag tacgactgca agatcatgac cagcaagacc   1200
gacgtgagca gcagcgtgat taccagcctg ggcgccatcg tgagctgcta cggcaagacc   1260
aagtgcaccg ccagcaacaa gaaccggggg atcatcaaga ccttcagcaa cggctgcgac   1320
tacgtgagca acaagggcgt ggataccgtg agcgtgggca caccctgta ctacgtgaat    1380
aagcaggagg gcaagagcct gtacgtgaag ggcgagccca tcatcaactt ctacgacccc   1440
ctggtgttcc ctagcgacga gttcgatgcc agcatcagcc aggtgaacga gaagatcaac   1500
cagagcctgg ccttcatcag gaagagcgac gagctgctgc acaatgtgaa tgccggcaag   1560
agcaccacca atatcatgat caccacaatc atcatcgtga tcattgtgat cctgctgtcc   1620
ctcatcgccg tgggcctgct gctgtactgc aaggccagaa gcacccctgt gaccctgtcc   1680
aaggatcagc tgagcggcat caacaatatc gccttctcca actga                   1725
```

<210> SEQ ID NO 36
<211> LENGTH: 1725
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 36

```
atggaactgc tgatcctgaa ggccaacgcc atcaccacca tcctgaccgc cgtgaccttc     60
tgcttcgcct ccggccagaa catcaccgag gaattctacc agtctacctg ctccgccgtg    120
tccaagggct acctgtctgc tctgagaacc ggctggtaca cctccgtgat caccatcgag    180
ctgtccaaca tcagaaaaaa caagtgcaac ggcaccgacg ccaaagtgaa gctgatcaag    240
caggaactgg acaagtacaa gaatgccgtg accgaactgc agctgctgat gcagtctacc    300
caggccacca caaccggggc cagacgcgag ctgcccagat tcatgaacta caccctgaac    360
aacgccaaaa agaccaacgt gaccctgtcc aagaagcgga gcggcggtt cctgggcttt    420
ctgctgggag tgggctccgc tatcgcttct ggcgtggccg tgtctaaggt gctgcacctg    480
gaaggcgaag tgaacaagat caagtccgcc ctgctgagca ccaacaaggc cgtggtgtcc    540
ctgagcaacg gcgtgtccgt gctgaccctc aaggtgctgg atctgaagaa ctacatcgac    600
aaacagctgc tgcccatcgt gaacaagcag tcctgctcca tctccaacat cgagacagtg    660
atcgagttcc agcagaagaa caaccggctg ctggaaatca cccgcgagtt ctccgtgaat    720
gccggcgtga ccacccccgt gtccacctac atgctgacca actccgagct gctgtctctg    780
atcaacgaca tgcccatcac caacgaccag aaaaagctga tgtccaacaa cgtgcagatc    840
gtgcggcagc agtcctacag catcatgtcc atcatcaaag aagaggtgct ggcctacgtg    900
gtgcagctgc ctctgtacgg cgtgatcgac accccctgct ggaagctgca caccagccct    960
```

```
ctgtgcacca ccaacaccaa agagggcagc aacatctgcc tgacccggac cgacagaggc    1020
tggtactgtg acaacgctgg ctccgtctca ttctttccac aagccgagac atgcaaggtg    1080
cagtccaacc gggtgttctg cgacaccatg aactccctga ccctgccctc tgaagtgaac    1140
ctgtgcaacg tggacatctt caaccctaag tacgactgca agatcatgac cagcaagacc    1200
gacgtgtcca gctctgtgat cacctccctg ggcgccatcg tgtcctgcta cggcaagacc    1260
aagtgcaccg cctccaacaa gaaccggggc atcatcaaga ccttctccaa cggctgcgac    1320
tatgtgtcta acaagggcgt ggacaccgtg tctgtgggca caccctgta ctacgtgaac    1380 aaacaggaag gcaagtccct gtacgtgaag ggcgagccta tcatcaactt ctacgacccc    1440
ctggtgttcc cagcgacga gttcgacgcc tccatcagcc aagtgaacga agatcaac      1500 cagtccctgg ccttcatccg gaagtccgat gagctgctgc acaatgtgaa cgccggcaag    1560
tccaccacca atatcatgat caccacaatc atcatcgtga ttatcgtgat cctgctgagc    1620
ctgatcgccg tgggcctgct gctgtactgc aaggccagat ccaccctgt gacactgagc     1680 aaggaccagc tgtccggcat caacaatatc gccttcagca actga                    1725
```

<210> SEQ ID NO 37
<211> LENGTH: 1725
<212> TYPE: DNA
<213> ORGANISM: Artificial Sequence
<220> FEATURE:
<223> OTHER INFORMATION: Description of Artificial Sequence: Synthetic
       polynucleotide

<400> SEQUENCE: 37

```
atggaactgc tgatcctgaa ggctaacgct atcaccacca tcctgaccgc tgtgaccttc     60
tgcttcgctt ccggccagaa catcaccgag gaattctacc agtctacctg ctccgctgtg    120
tccaagggtt acctgtccgc tctgcgtacc ggctggtaca cctccgtgat caccatcgag    180
ctgtccaaca tcaagaagaa caagtgcaac ggcaccgacg ctaaagtgaa gctgatcaag    240
caagagctgg acaagtacaa gaacgctgtc accgaactgc agctgctgat gcagtccacc    300
caggctacca caaccgtgc tcgtcgcgag ctgcccgtt tcatgaacta caccctgaac     360
aacgccaaga agaccaacgt caccctgtcc aagaagcgca agcgccgttt cctgggtttc    420
ctgctgggtg tcggttccgc tatcgcctcc ggtgtcgctg tctctaaggt gctgcacctc    480
gagggcgaag tgaacaagat caagtccgcc ctgctgtcca ccaacaaggc tgtggtgtcc    540
ctgtctaacg gtgtctccgt gctgaccctc caaggtcctgg acctgaagaa ctacatcgac    600
aagcaactgc tgcccatcgt gaacaagcag tcctgctcca ctccaacat cgagactgtg     660 atcgagttcc agcaaaagaa caaccgcctg ctcgagatca cccgcgagtt ctccgtgaac    720
gctggtgtca ccaccccgt gtccacctac atgctgacca ctccgagct gctgtccctg     780 atcaacgaca tgcccatcac caacgaccaa aagaagctga tgtccaacaa cgtgcagatc    840
gtgcgtcagc agtcctactc tatcatgagc atcatcaagg aagaggtgct ggcttacgtg    900
gtgcagctgc cctgtacgg tgtcatcgac accccctgct ggaagctgca caccctcccca    960 ctgtgcacca ccaacaccaa ggaaggttcc aacatctgcc tgacccgtac cgaccgtggc    1020
tggtactgcg acaacgctgg ttccgttca ttcttcccac aagccgagac ttgcaaggtg    1080
cagtccaacc gtgtgttctg cgacaccatg aactccctga ccctgccctc cgaagtcaac    1140
ctgtgcaacg tggacatctt caaccctaag tacgactgca agatcatgac cagcaagacc    1200
gacgtgtcct cctctgtcat cacctccctg ggtgctatcg tgtcctgcta cggcaagacc    1260
```

```
aagtgcaccg cttccaacaa gaaccgcggt atcatcaaga ccttctccaa cggttgcgac    1320
tacgtcagca acaagggcgt ggacaccgtg tccgtgggca cacccctgta ctacgtcaac    1380
aagcaagagg gcaagtccct gtacgtgaag ggcgagccca tcatcaactt ctacgacccc    1440
ctggtgttcc catccgacga gttcgacgct tccatctccc aagtgaacga gaagatcaac    1500
cagtccctgg ctttcatccg caagtccgac gagctgctcc acaacgtcaa cgctggcaag    1560
tccaccacta acatcatgat cactaccatc atcatcgtga tcatcgtcat cctgctgagc    1620
ctgatcgctg tgggcctgct gctgtactgc aaggctcgtt ccaccctgt gactctgtcc    1680 aaggaccagc tgtccggtat caacaacatc gccttcagca actaa                    1725
```

<210> SEQ ID NO 38
<211> LENGTH: 1725
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 38

```
atggaactgc tgatcctgaa ggccaacgcc atcaccacca tcctgaccgc cgtgaccttc      60
tgcttcgcca gcggccagaa catcaccgag gaattctacc agagcacctg tagcgccgtg     120
tccaagggct acctgagcgc cctgagaacc ggctggtaca ccagcgtgat caccatcgag     180
ctgagcaaca tcaagaaaaa caagtgcaac ggcaccgacg ccaaagtgaa gctgatcaag     240
caggaactgg acaagtacaa gaacgccgtg acagaactgc agctgctgat gcagagcacc     300
caggccacca acaacagagc cagacgcgag ctgcccagat tcatgaacta caccctgaac     360
aacgccaaaa agaccaacgt gaccctgagc aagaagagga gcgcagatt cctgggcttc     420 ctgctgggcg tgggcagcgc tattgcttct ggcgtggccg tgtctaaggt gctgcacctg     480
gaaggcgaag tgaacaagat caagtccgcc ctgctgagca ccaacaaggc cgtggtgtct     540
ctgagcaacg gcgtgtccgt gctgaccagc aaggtgctgg atctgaagaa ctacatcgac     600
aaacagctgc tgcccatcgt gaacaagcag agctgcagca tcagcaacat cgagacagtg     660
atcgagttcc agcagaagaa caaccggctg ctggaaatca cccgcgagtt cagcgtgaac     720
gctggcgtga ccaccccgt gtccacctac atgctgacca acagcgagct gctgagcctg     780
atcaacgaca tgcccatcac caacgaccag aaaaagctga tgagcaacaa cgtgcagatc     840
gtgcggcagc agagctactc catcatgagc atcatcaaag agaggtgct ggcctacgtg     900 gtgcagctgc ctctgtacgg cgtgatcgac accccctgct ggaagctgca caccagccct     960
ctgtgcacca ccaacaccaa gaggggctcc aacatctgcc tgaccagaac cgacagaggc    1020
tggtactgcg acaacgccgg ctccgtctca ttctttccac aagccgagac atgcaaggtg    1080
cagagcaaca gagtgttctg cgacaccatg aacagcctga cctgccctc tgaagtgaac    1140 ctgtgcaacg tggacatctt caaccctaag tacgactgca agatcatgac ctccaagacc    1200
gacgtgtcca gctccgtgat cacaagcctg ggcgccatcg tgtcctgcta cggcaagacc    1260
aagtgcaccg ccagcaacaa gaacagggga atcatcaaga ccttcagcaa cggctgcgac    1320
tacgtgtcca acaagggggt ggacaccgtg tctgtgggca cacccctgta ctacgtgaac    1380
aaacaggaag gcaagagcct gtacgtgaag ggcgagccca tcatcaactt ctacgacccc    1440
ctggtgttcc ccagcgacga gttcgacgcc agcatctccc aagtgaacga gaagatcaac    1500
cagagcctgg cctttcatcag aaagtccgat gagctgctgc acaatgtgaa cgccggcaag    1560
```

```
agcaccacaa acatcatgat caccactatc atcatcgtga tcattgtgat cctgctgtcc    1620
ctgatcgccg tgggcctgct gctgtactgc aaggccagat ccaccccctgt gaccctgtcc    1680 aaggaccagc tgagcggcat caacaatatc gccttctcca actga                     1725
```

<210> SEQ ID NO 39
<211> LENGTH: 1725
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39

```
atggaactgc tgatccacag aagcagcgcc atcttcctga ccctggccat caacgccctg    60
tacctgacca gcagccagaa catcaccgag gaattctacc agagcacctg tagcgccgtg    120
tcccggggct actttagcgc cctgagaacc ggctggtaca ccagcgtgat caccatcgag    180
ctgagcaata tcaccgagac aaagtgcaac ggcaccgaca ccaaagtgaa gctgatcaag    240
caggaactgg acaagtacaa gaacgccgtg accgaactgc agctgctgat gcagaatacc    300
cctgccgcca caaccgggc cagaagagaa gcccccagc acatgaacta caccatcaac    360
accaccaaga acctgaacgt gtccatcagc aagaagcgga gcggcggtt cctgggcttt    420 ctgctgggag tgggaagcgc cattgccagc ggaatcgccg tgtctaaggt gctgcacctg    480
gaaggcgaag tgaacaagat caagaatgcc ctgctgagca ccaacaaggc cgtggtgtcc    540
ctgagcaacg gcgtgtccgt gctgacctcc aaggtgctgg atctgaagaa ctacatcaac    600
aaccagctgc tgcccatcgt gaaccagcag agctgccgga tcttcaacat cgagacagtg    660
atcgagttcc agcagaagaa cagcaggctg ctggaaatca cccgcgagtt cagcgtgaac    720
gctggcgtga ccacacccct gagcacctac atgctgacca cagcgagct gctgtccctg    780 atcaatgaca tgcccatcac caacgaccag aaaaagctga tgagcagcaa cgtgcagatc    840
gtgcggcagc agtcctacag catcatgagc atcatcaaag aagaggtgct ggcctacgtg    900
gtgcagctgc ctatctacgg cgtgatcgac accccctgct ggaagctgca caccagccct    960
ctgtgcacca ccaacatcaa agagggcagc aacatctgcc tgaccagaac cgaccggggc    1020
tggtactgcg ataatgccgg ctccgtctca ttctttccac aagccgatac ctgcaaggtg    1080
cagagcaacc gggtgttctg cgacaccatg aacagcctga ccctgccagc gaagtgtcc    1140 ctgtgtaaca ccgacatctt caactctaag tacgactgca agatcatgac cagcaagacc    1200
gacatcagct cctccgtgat cacaagcctg ggcgccatcg tgtcctgcta cggcaagacc    1260
aagtgcaccg ccagcaacaa gaaccgggga tcatcaaga ccttcagcaa cggctgcgac    1320
tacgtgtcca acaagggggt ggacaccgtg tctgtgggca cacccgtgta ctacgtgaac    1380
aagctggaag gaagaatct gtacgtgaag ggcgagccca tcatcaacta ctacgacccc    1440
ctggtgttcc ccagcgacga gttcgatgcc agcatcagcc aagtgaacga gaagatcaac    1500
cagagcctgg ccttcatcag aaagtccgat gagctgctgc acaatgtgaa caccggcaag    1560
tccaccacaa atatcatgat caccaccatc attatcgtga tcatcgtggt gctgctgagc    1620
ctgatcgcca tcggcctgct gctgtactgc aaggccaaga acacccccgt gaccctgtcc    1680
aaggatcagc tgagcggcat caacaatatc gccttctcca gtga                    1725
```

<210> SEQ ID NO 40
<211> LENGTH: 1725
<212> TYPE: DNA

<213> ORGANISM: Artificial Sequence
<220> FEATURE:
<223> OTHER INFORMATION: Description of Artificial Sequence: Synthetic
      polynucleotide

<400> SEQUENCE: 40

```
atggaactgc tgatccaccg gtcctccgcc atcttcctga ccctggccat caacgccctg      60
tacctgacct cctcccagaa catcaccgag gaattctacc agtctacctg ctccgccgtg     120
tcccggggct acttctctgc tctgagaacc ggctggtaca cctccgtgat caccatcgag     180
ctgtccaata tcaccgagac aaagtgcaac ggcaccgaca ccaaagtgaa gctgatcaag     240
caggaactgg acaagtacaa gaacgccgtg accgaactgc agctgctgat gcagaatacc     300
cctgccgcca caaccgggc cagaagagaa gcccccagc acatgaacta ccaccatcaac     360 accaccaaga acctgaacgt gtccatctcc aagaagcgga agcggcggtt cctgggcttt     420
ctgctgggag tgggctccgc tatcgcctcc ggaatcgccg tgtctaaggt gctgcacctg     480
gaaggcgaag tgaacaagat caagaatgcc ctgctgtcca ccaacaaggc cgtggtgtcc     540
ctgtccaacg gcgtgtccgt gctgacctcc aaggtgctgg atctgaagaa ctacatcaac     600
aaccagctgc tgcccatcgt gaaccagcag tcctgccgga tcttcaacat cgagacagtg     660
atcgagttcc agcagaagaa ctcccggctg ctggaaatca cccgcgagtt ctctgtgaat     720
gccggcgtga ccaccccct gtccacctac atgctgacca actccgagct gctgtccctg     780
atcaacgaca tgcccatcac caacgaccag aaaaagctga tgtcctccaa cgtgcagatc     840
gtgcggcagc agagctactc catcatgtcc attatcaaag aagaggtgct ggcctacgtg     900
gtgcagctgc ctatctacgg cgtgatcgac accccctgct ggaagctgca caccagccct     960
ctgtgcacca ccaacatcaa agagggctcc aacatctgcc tgaccagaac cgaccggggc    1020
tggtactgtg acaacgctgg ctccgtctca ttctttccac aagccgatac ctgcaaggtg    1080
cagtccaacc gggtgttctg cgacaccatg aattctctga ccctgcctc cgaagtgtct    1140 ctgtgtaaca ccgacatctt caactctaag tacgactgca agatcatgac cagcaagacc    1200
gatatctcca gctctgtgat cacctccctg ggcgccatcg tgtcctgcta cggcaagacc    1260
aagtgcaccg cctccaacaa gaaccggggc atcatcaaga cctctccaa cggctgcgac    1320 tacgtgtcca acaaggggt ggacaccgtg tctgtgggca cacccctgta ctacgtgaac    1380
aagctggaag gaagaatct gtacgtgaag ggcgagccca tcatcaacta ctacgacccc    1440
ctggtgttcc ccagcgacga gttcgacgcc tccatcagcc aagtgaacga gaagatcaac    1500
cagtccctgg ccttcatccg gaagtccgat gagctgctgc acaatgtgaa caccggcaag    1560
tccaccacaa atatcatgat caccaccatc attatcgtga tcatcgtggt gctgctgagc    1620
ctgatcgcca tcggcctgct gctgtactgc aaggccaaga acacccccgt gaccctgagc    1680
aaggaccagc tgtccggcat caacaatatc gccttcagca gtga                     1725
```

<210> SEQ ID NO 41
<211> LENGTH: 1725
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41

```
atggaactgc tgatccaccg ttcctccgct atcttcctga ccctggctat caacgctctg      60
tacctgacct cctcccagaa catcaccgag gaattctacc agtctacctg ctccgctgtg     120
```

-continued

```
tcccgtggtt acttctccgc tctgcgtacc ggctggtaca cctccgtgat caccatcgag      180
ctgtccaaca tcactgagac taagtgcaac ggcaccgaca ccaaagtgaa gctgatcaag      240
caagagctgg acaagtacaa gaacgctgtg accgaactgc agctgctgat gcagaacacc      300
cccgctgcta caaccgtgc tcgtcgcgaa gctccccagc acatgaacta caccatcaac       360
accaccaaga acctgaacgt gtccatctcc aagaagcgca agcgccgttt cctgggtttc      420
ctgctgggtg tcggttccgc tatcgcttcc ggtatcgctg tctccaaggt gctgcacctc      480
gagggcgaag tgaacaagat caagaacgcc ctgctgtcca ccaacaaggc tgtggtgtcc      540
ctgtccaacg tgtctccgt gctgacctcc aaggtcctcg acctgaagaa ctacatcaac       600
aaccagctgc tgcccatcgt gaaccagcag tcctgccgta tcttcaacat cgagactgtg      660
atcgagttcc agcagaagaa ctcccgtctg ctcgagatca cccgcgagtt ctccgtgaac      720
gctggtgtca ccacccccct gtccacctac atgctgacca actccgagct gctgtccctg      780
atcaacgaca tgcccatcac caacgaccaa agaagctga tgtcctccaa cgtgcagatc       840
gtgcgtcagc agtcttactc catcatgtcc atcatcaagg aagaggtgct ggcttacgtg      900
gtgcagctgc ctatctacgg tgtcatcgac accccctgct ggaagctgca cacctccccca    960 ctgtgcacca ccaacatcaa ggaaggttcc aacatctgcc tgacccgtac cgaccgtggc     1020
tggtactgcg acaacgctgg ttccgtttca ttcttcccac aagccgacac ttgcaaggtg    1080
cagtccaacc gtgtgttctg cgacaccatg aactccctga ctctgccctc cgaggtgtcc    1140
ctctgcaaca ccgacatctt caactctaag tacgactgca agatcatgac ctctaagact    1200
gacatctcct ccagcgtcat cacctccctg ggtgctatcg tgtcctgcta cggcaagacc    1260
aagtgcaccg cttccaacaa gaaccgcggt atcatcaaga ccttctccaa cggttgcgac    1320
tacgtgtcca caagggcgt ggacaccgtg tccgtgggca cacccctgta ctacgtgaac     1380
aagctcgagg gcaagaacct ctacgtgaag ggcgagccta tcatcaacta ctacgacccc    1440
ctggtgttcc catccgacga gttcgacgct tccatctccc aagtgaacga aagatcaac     1500 cagtccctgg ctttcatccg caagtccgac gagctgctcc acaacgtgaa caccggcaag    1560
tccactacta catcatgat caccactatc atcatcgtga tcatcgtcgt gctgctgagc     1620
ctgatcgcta tcggcctgct gctgtactgc aaggctaaga acactcccgt gaccctgtct    1680
aaggaccagc tgtccggtat caacaacatc gccttcagca agtaa                    1725
```

<210> SEQ ID NO 42
<211> LENGTH: 1725
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 42

```
atggaactgc tgatccacag aagcagcgcc atcttcctga ccctggccat caacgccctg       60
tacctgacca gcagccagaa catcaccgag gaattctacc agagcacctg tagcgccgtg      120
tccagaggct acttcagcgc cctgagaacc ggctggtaca ccagcgtgat caccatcgag      180
ctgagcaaca tcacagagac aaagtgcaac ggcaccgaca ccaaagtgaa gctgatcaag      240
caggaactgg acaagtacaa gaacgccgtg accgaactgc agctgctgat gcagaacacc      300
cctgccgcca caacagagc cagaagagaa gccccccagc acatgaacta caccatcaac      360
accaccaaga acctgaacgt gtccatcagc aagaagagga agagaagatt cctgggcttc     420
```

```
ctgctgggcg tgggcagcgc tatcgcttct ggaatcgccg tgtctaaggt gctgcacctg      480
gaaggcgaag tgaacaagat caagaacgct ctgctgagca ccaacaaggc cgtggtgtcc      540
ctgagcaacg gcgtgtccgt gctgacctcc aaggtgctgg atctgaagaa ctacatcaac      600
aaccagctgc tgcccatcgt gaaccagcag agctgcagaa tcttcaacat cgagacagtg      660
atcgagttcc agcagaagaa cagcaggctg ctggaaatca cccgcgagtt cagcgtgaac      720
gctggcgtga ccacacccct gagcacctac atgctgacca cagcgagct gctgtctctg       780 atcaacgaca tgcccatcac caacgaccag aaaaagctga tgagcagcaa cgtgcagatc      840
gtgcggcagc agtcctacag catcatgagc atcatcaaag aagaggtgct ggcctacgtg      900
gtgcagctgc ctatctacgg cgtgatcgac acccctgct ggaagctgca caccagccct       960
ctgtgcacca ccaacatcaa agagggcagc aacatctgcc tgaccagaac cgacagaggc     1020
tggtactgcg acaacgccgg ctccgtctca ttctttccac aagccgacac atgcaaggtg     1080
cagagcaaca gagtgttctg cgacaccatg aacagcctga cactgcccag cgaagtgtcc     1140
ctgtgtaaca ccgacatctt caactctaag tacgactgca agatcatgac cagcaagacc     1200
gacatcagct cctccgtgat cacaagcctg ggcgccatcg tgtcctgcta cggcaagacc     1260
aagtgcaccg ccagcaacaa gaacagggga atcatcaaga ccttcagcaa cggctgcgac     1320
tacgtgtcca caaggggggt ggacaccgtg tctgtgggca caccctgta ctacgtgaac      1380 aagctggaag gaagaatct gtacgtgaag ggcgagccca tcatcaacta ctacgacccc     1440
ctggtgttcc ccagcgacga gttcgacgcc agcatcagcc aagtgaacga gaagatcaac     1500
cagagcctgg ccttcatcag aaagtccgat gagctgctgc acaatgtgaa caccggcaag     1560
tccacaacaa acatcatgat caccaccatc attatcgtga tcatcgtggt gctgctgagc     1620
ctgatcgcca tcggcctgct gctgtactgc aaggccaaga cacacccgt gaccctgtcc      1680 aaggaccagc tgagcggcat caacaatatc gccttctcca agtga                    1725
```

<210> SEQ ID NO 43
<211> LENGTH: 1707
<212> TYPE: DNA
<213> ORGANISM: Artificial Sequence
<220> FEATURE:
<223> OTHER INFORMATION: Description of Artificial Sequence: Synthetic
       polynucleotide

<400> SEQUENCE: 43

```
atggaactgc tgatcctgaa ggccaacgcc atcaccacca tcctgaccgc cgtgaccttc       60
tgcttcgcca gcggccagaa catcaccgag gaattctacc agagcacctg cagcgccgtg      120
agcaagggct acctgagcgc cctgcgacc ggctggtaca ccagcgtgat caccatcgag       180
ctgtccaaca tcaagaaaaa caagtgcaac ggcaccgacg ccaaagtgaa gctgatcaag      240
caggaactgg acaagtacaa gaacgccgtg accgagctgc agctgctgat gcagagcacc      300
cccgccacca caacagagc cagaagagag ctgccccgt tcatgaacta cacccctgaac       360 aacgccaaga aaaccaacgt gaccctgagc aagaagagaa agagaagatt cctgggcttc      420
ctgctgggcg tgggcagcgc cattgccagc ggcgtggccg tgtgcaaagt gctgcacctg      480
gaaggcgaag tgaacaagat caagtccgcc ctgctgtcca ccaacaaggc cgtggtgtcc      540
ctgagcaacg gcgtgagcgt gctgacctcc aaggtgctgg atctgaagaa ctacatcgac      600
aagcagctgc tgcccatcct gaacaagcag agctgcagca tcagcaacat cgagacagtg      660
atcgagttcc agcagaagaa caaccggctg ctggaaatca cccgggagtt cagcgtgaac      720
```

```
gccggagtga ccaccccgt gtccacctac atgctgacca acagcgagct gctgtccctg      780
atcaatgaca tgcccatcac caacgaccag aaaaagctga tgagcaacaa cgtgcagatc      840
gtgcggcagc agagctactc catcatgtgc atcatcaaag aagaggtgct ggcctacgtg      900
gtgcagctgc ccctgtacgg cgtgatcgac accccctgct ggaagctgca caccagcccc      960
ctgtgcacaa ccaacaccaa agagggcagc aacatctgcc tgacccggac cgaccggggc     1020
tggtactgcg acaacgccgg cagcgtgtcc ttctttccac aggccgagac atgcaaggtg     1080
cagagcaacc gggtgttctg cgacaccatg aacagcctga ccctgcccct cgaagtgaac     1140
ctgtgcaacg tggacatctt caaccccaag tacgactgca agatcatgac ctccaagacc     1200
gacgtgtcca gctccgtgat cacctccctg ggcgccatcg tgtcctgcta cggcaagacc     1260
aagtgcaccg ccagcaacaa gaacagaggc atcatcaaga ccttcagcaa cggctgcgac     1320
tacgtgtcca ataagggcgt ggacaccgtg tccgtgggca cacactgta ctacgtgaat     1380 aagcaggaag gcaagagcct gtacgtgaag ggcgagccca tcatcaactt ctacgacccc     1440
ctggtgttcc ccagcgacga gttcgacgcc agcatcagcc aggtgaacga aagatcaac     1500 cagagcctgg ccttcatcag aaagagcgac gaactgctgt ccgccatcgg cggctacatc     1560
cccgaggccc ccagagatgg ccaggcctac gtgcggaagg acggcgagtg ggtgctgctg     1620
tctacatttc tgggcggcct ggtgcctaga ggctctcacc accaccatca ccacagcgcc     1680
tggtcccacc cccagttcga gaagtga                                         1707

<210> SEQ ID NO 44
<211> LENGTH: 1707
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44
atggaactgc tgatcctgaa ggccaacgcc atcaccacca tcctgaccgc cgtgaccttc       60
tgcttcgcca gcggccagaa catcaccgag gaattctacc agagcacctg cagcgccgtg      120
agcaagggct acctgagcgc cctgcggacc ggctggtaca ccagcgtgat caccatcgag      180
ctgtccaaca tcaaagaaaa caagtgcaac ggcaccgacg ccaaagtgaa gctgatcaag      240
caggaactgg acaagtacaa gaacgccgtg accgagctgc agctgctgat gcagagcacc      300
cccgccacca acaacagagc cagaagagag ctgccccggt tcatgaacta caccctgaac      360
aacgccaaga aaccaacgt gaccctgagc aagaagagaa agaagatt cctgggcttc       420 ctgctgggcg tgggcagcgc cattgccagc ggcgtggccg tgtgcaaagt gctgcacctg      480
gaaggcgaag tgaacaagat caagtccgcc ctgctgtcca ccaacaaggc cgtggtgtcc      540
ctgagcaacg gcgtgagcgt gctgaccagc aaggtgctgg atctgaagaa ctacatcgac      600
aagcagctgc tgcccatcgt gaacaagcag agctgcagca tcagcaacat cgagacagtg      660
atcgagttcc agcagaagaa caaccggctg ctggaaatca cccgggagtt cagcgtgaac      720
gccggagtga ccaccccgt gtccacctac atgctgacca acagcgagct gctgtccctg       780
atcaatgaca tgcccatcac caacgaccag aaaaagctga tgagcaacaa cgtgcagatc      840
gtgcggcagc agagctactc catcatgtgc atcatcaaag aagaggtgct ggcctacgtg      900
gtgcagctgc ccctgtacgg cgtgatcgac accccctgct ggaagctgca caccagcccc      960
ctgtgcacaa ccaacaccaa agagggcagc aacatctgcc tgacccggac cgaccggggc     1020
```

```
tggtactgcg acaacgccgg cagcgtgtcc ttctttccac aggccgagac atgcaaggtg    1080
cagagcaacc gggtgttctg cgacaccatg aacagcctga ccctgccctc cgaagtgaac    1140
ctgtgcaacg tggacatctt caaccccaag tacgactgca agatcatgac ctccaagacc    1200
gacgtgtcca gctccgtgat cacctccctg ggcgccatcg tgtcctgcta cggcaagacc    1260
aagtgcaccg ccagcaacaa gaacagaggc atcatcaaga ccttcagcaa cggctgcgac    1320
tacgtgtcca ataagggcgt ggacaccgtg tccgtgggca acacactgta ctacgtgaat    1380
aagcaggaag gcaagagcct gtacgtgaag ggcgagccca tcatcaactt ctacgacccc    1440
ctggtgttcc ccagcgacga gttcgacgcc agcatcagcc aggtgaacga gaagatcaac    1500
cagagcctgg ccttcatcag aaagagcgac gaactgctgt ccgccatcgg cggctacatc    1560
cccgaggccc ccagagatgg ccaggcctac gtgcggaagg acggcgagtg ggtgctgctg    1620
tctacatttc tgggcggcct ggtgcctaga ggctctcacc accaccatca ccacagcgcc    1680
tggtcccacc cccagttcga gaagtga                                       1707

<210> SEQ ID NO 45
<211> LENGTH: 1707
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 45
atggaactgc tgatcctgaa ggccaacgcc atcaccacca tcctgaccgc cgtgaccttc      60
tgcttcgcca gcggccagaa catcaccgag gaattctacc agagcacctg cagcgccgtg    120
agcaagggct acctgagcgc cctgcggacc ggctggtaca ccagcgtgat caccatcgag    180
ctgtccaaca tcaaagaaaa caagtgcaac ggcaccgacg ccaaagtgaa gctgatcaag    240
caggaactgg acaagtacaa gaacgccgtg accgagctgc agctgctgat gcagagcacc    300
cccgccacca caacagagc cagaagagag ctgccccggt tcatgaacta cacc ctgaac    360 aacgccaaga aaccaacgt gaccctgagc aagaagagaa agaagattc ctgggcttc       420 ctgctgggcg tgggcagcgc cattgccagc ggcgtggccg tgtccaaagt gctgcacctg    480
gaaggcgaag tgaacaagat caagtccgcc ctgctgtcca ccaacaaggc cgtggtgtcc    540
ctgagcaacg gcgtgagcgt gctgaccttc aaggtgctgg atctgaagaa ctacatcgac    600
aagcagctgc tgcccatcct gaacaagcag agctgcagca tcagcaacat cgagacagtg    660
atcgagttcc agcagaagaa caaccggctg ctggaaatca cccgggagtt cagcgtgaac    720
gccggagtga ccaccccccgt gtccacctac atgctgacca cagcgagct gctgtccctg    780 atcaatgaca tgcccatcac caacgaccag aaaaagctga tgagcaacaa cgtgcagatc    840
gtgcggcagc agagctactc catcatgagc atcatcaaag aagaggtgct ggcctacgtg    900
gtgcagctgc ccctgtacgg cgtgatcgac accccctgct ggaagctgca caccagcccc    960
ctgtgcacaa ccaacaccaa gagggcagc aacatctgcc tgacccggac cgaccggggc   1020
tggtactgcg acaacgccgg cagcgtgtcc ttctttccac aggccgagac atgcaaggtg    1080
cagagcaacc gggtgttctg cgacaccatg aacagcctga ccctgccctc cgaagtgaac    1140
ctgtgcaacg tggacatctt caaccccaag tacgactgca agatcatgac ctccaagacc    1200
gacgtgtcca gctccgtgat cacctccctg ggcgccatcg tgtcctgcta cggcaagacc    1260
aagtgcaccg ccagcaacaa gaacagaggc atcatcaaga ccttcagcaa cggctgcgac    1320
```

```
tacgtgtcca ataagggcgt ggacaccgtg tccgtgggca acacactgta ctacgtgaat   1380
aagcaggaag gcaagagcct gtacgtgaag ggcgagccca tcatcaactt ctacgacccc   1440
ctggtgttcc ccagcgacga gttcgacgcc agcatcagcc aggtgaacga gaagatcaac   1500
cagagcctgg ccttcatcag aaagagcgac gaactgctgt ccgccatcgg cggctacatc   1560
cccgaggccc ccagagatgg ccaggcctac gtgcggaagg acggcgagtg ggtgctgctg   1620
tctacatttc tgggcggcct ggtgcctaga ggctctcacc accaccatca ccacagcgcc   1680
tggtcccacc cccagttcga gaagtga                                      1707

<210> SEQ ID NO 46
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 46

His His His His His His
1               5

<210> SEQ ID NO 47
<211> LENGTH: 488
<212> TYPE: PRT
<213> ORGANISM: Human respiratory syncytial virus

<400> SEQUENCE: 47

Gln Asn Ile Thr Glu Glu Phe Tyr Gln Ser Thr

-continued

```
Tyr Met Leu Thr Asn Ser Glu Leu Leu Ser Leu Ile Asn Asp Met Pro
225                 230                 235                 240

Ile Thr Asn Asp Gln Lys Lys Leu Met Ser Asn Asn Val Gln Ile Val
                245                 250                 255

Arg Gln Gln Ser Tyr Ser Ile Met Ser Ile Ile Lys Glu Glu Val Leu
                260                 265                 270

Ala Tyr Val Val Gln Leu Pro Leu Tyr Gly Val Ile Asp Thr Pro Cys
            275                 280                 285

Trp Lys Leu His Thr Ser Pro Leu Cys Thr Thr Asn Thr Lys Glu Gly
        290                 295                 300

Ser Asn Ile Cys Leu Thr Arg Thr Asp Arg Gly Trp Tyr Cys Asp Asn
305                 310                 315                 320

Ala Gly Ser Val Ser Phe Phe Pro Gln Ala Glu Thr Cys Lys Val Gln
                325                 330                 335

Ser Asn Arg Val Phe Cys Asp Thr Met Asn Ser Leu Thr Leu Pro Ser
                340                 345                 350

Glu Val Asn Leu Cys Asn Val Asp Ile Phe Asn Pro Lys Tyr Asp Cys
            355                 360                 365

Lys Ile Met Thr Ser Lys Thr Asp Val Ser Ser Ser Val Ile Thr Ser
        370                 375                 380

Leu Gly Ala Ile Val Ser Cys Tyr Gly Lys Thr Lys Cys Thr Ala Ser
385                 390                 395                 400

Asn Lys Asn Arg Gly Ile Ile Lys Thr Phe Ser Asn Gly Cys Asp Tyr
                405                 410                 415

Val Ser Asn Lys Gly Val Asp Thr Val Ser Val Gly Asn Thr Leu Tyr
                420                 425                 430

Tyr Val Asn Lys Gln Glu Gly Lys Ser Leu Tyr Val Lys Gly Glu Pro
                435                 440                 445

Ile Ile Asn Phe Tyr Asp Pro Leu Val Phe Pro Ser Asp Glu Phe Asp
            450                 455                 460

Ala Ser Ile Ser Gln Val Asn Glu Lys Ile Asn Gln Ser Leu Ala Phe
465                 470                 475                 480

Ile Arg Lys Ser Asp Glu Leu Leu
                485
```